(12) United States Patent
Dublanchet et al.

(10) Patent No.: US 9,089,500 B2
(45) Date of Patent: Jul. 28, 2015

(54) COSMETIC TREATMENT PROCESSES AND KIT

(75) Inventors: Anne-Claude Dublanchet, Antony (FR); Christian Blaise, Saint Mande (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/130,597

(22) PCT Filed: Jul. 9, 2012

(86) PCT No.: PCT/FR2012/051613
§ 371 (c)(1),
(2), (4) Date: Feb. 20, 2014

(87) PCT Pub. No.: WO2013/004982
PCT Pub. Date: Jan. 10, 2013

(65) Prior Publication Data
US 2014/0155352 A1    Jun. 5, 2014

Related U.S. Application Data

(60) Provisional application No. 61/594,166, filed on Feb. 2, 2012.

(30) Foreign Application Priority Data

Jul. 7, 2011    (FR) ...................................... 11 56151

(51) Int. Cl.
| | | |
|---|---|---|
| *A61K 31/513* | (2006.01) | |
| *C07D 239/20* | (2006.01) | |
| *A61K 8/58* | (2006.01) | |
| *A61K 8/49* | (2006.01) | |
| *A61Q 5/00* | (2006.01) | |
| *A61Q 5/12* | (2006.01) | |
| *A61Q 3/00* | (2006.01) | |
| *A61Q 19/00* | (2006.01) | |

(52) U.S. Cl.
CPC ............... *A61K 8/585* (2013.01); *A61K 8/4926* (2013.01); *A61K 8/4953* (2013.01); *A61Q 3/00* (2013.01); *A61Q 5/00* (2013.01); *A61Q 5/12* (2013.01); *A61Q 19/00* (2013.01); *A61K 2800/884* (2013.01)

(58) Field of Classification Search
CPC ........................... A61K 31/513; C07D 239/20
USPC ........... 544/242, 298, 316; 514/256, 269, 272
See application file for complete search history.

(56) References Cited

U.S. PATENT DOCUMENTS

| | | | |
|---|---|---|---|
| 7,863,478 | B2 | 1/2011 | Carola et al. |
| 8,575,341 | B2 * | 11/2013 | Mougin et al. ................ 544/296 |
| 8,603,446 | B2 * | 12/2013 | Mougin et al. ............... 424/70.1 |

FOREIGN PATENT DOCUMENTS

| | | |
|---|---|---|
| DE | 102004039281 A1 | 2/2006 |
| EP | 2140858 A1 | 1/2010 |
| EP | 2 189 151 A1 | 5/2010 |
| FR | 2760359 A1 | 9/1998 |
| FR | 2954941 A1 | 7/2011 |
| WO | WO-2011080494 A2 | 7/2011 |

* cited by examiner

Primary Examiner — Golam M M Shameem
(74) Attorney, Agent, or Firm — Novak Druce Connolly Bove + Quigg LLP

(57) ABSTRACT

The present invention relates to a cosmetic process for treating keratin materials, which can give them, especially in a long-lasting and reversible manner, interesting cosmetic properties; this process comprising the application to said materials:
in a first stage, of a cosmetic composition comprising at least one graftable species, comprising at least one unit of formula (Ia):
and in a second stage, of a cosmetic composition comprising at least one cosmetic active agent bearing at least one unit of formula (Ia):

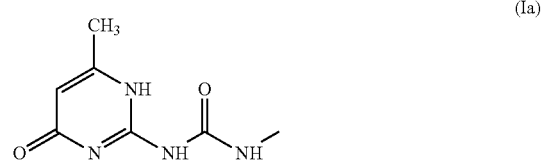

(Ia)

The invention also relates to a kit comprising said compositions.

9 Claims, No Drawings

COSMETIC TREATMENT PROCESSES AND KIT

CROSS REFERENCE TO RELATED APPLICATIONS

This application is a National Phase filing under 35 U.S.C. §371 of PCT/FR2012/051613 filed on Jul. 9, 2012; and this application claims priority to Application No. 1156151 filed in France on Jul. 7, 2011; and this application claims the benefit of U.S. Provisional Application No. 61/594,166 filed on Feb. 2, 2012; the entire contents of all are hereby incorporated by reference.

The present invention relates to a cosmetic process for treating keratin materials, which can give them, especially in a long-lasting and reversible manner, interesting cosmetic properties.

In the field of haircare, it is constantly sought to dye or permanent-wave the hair, without damaging it; it is also sought to improve the properties of keratin materials, especially of dyed or permanent-waved hair, and also to combat the damage suffered, such as external attack by pollution and ultraviolet radiation or chemical attack such as that caused by oxidizing, reducing or alkaline treatments, dyeing or permanent-waving.

Among the types of damage suffered by the hair, mention may be made especially of the loss of sheen, the increased hydrophilic nature, the loss or detachment of some of the scales, and difficulties in disentangling.

To improve the properties of the hair, it is known practice to use compositions containing cosmetic active agents in order to provide said keratin materials with all the beneficial effects associated with these cosmetic active agents. This is also transposable to other keratin materials such as the nails, the eyelashes and the skin. However, the remanence and efficacy of these active agents are currently insufficient, since they may especially be readily removed on shampooing; moreover, the associations between treating care and dye compositions are not always easy, or infinitely variable.

In the field of skincare, it is always sought to provide extreme staying power to makeup, or to certain active agents such as sunscreens. The deposit on the skin must be able to withstand external attack, for instance pollution or UV rays, or attack associated with use over a long period, such as heat, bathing or perspiration. Moreover, it is also sought to combine this long staying power with makeup removal that is easy and controlled by the consumer.

The aim of the present invention is to propose a cosmetic process for treating keratin materials, which can give them, in a long-lasting and preferably reversible manner, cosmetic properties, including color.

One subject of the present invention is thus a cosmetic process for treating keratin materials, comprising the application to said materials:
- in a first stage, of a cosmetic composition comprising at least one graftable species, comprising at least one unit of formula (Ia) as defined below:
- and in a second stage, of a cosmetic composition comprising at least one cosmetic active agent bearing at least one unit of formula (Ia).

Another subject of the invention is a cosmetic process for treating keratin materials, comprising the application to said materials of a cosmetic composition comprising, as a mixture, at least one graftable species, comprising at least one unit of formula (Ia) as defined below and at least one cosmetic active agent bearing at least one unit of formula (Ia).

It has in point of fact been found that products comprising species capable of mutually forming physical interactions, especially products comprising units of formula (Ia), can give keratin materials remanent cosmetic qualities, including color. These products are especially characterized by the presence of at least one species that is capable of giving 3 and preferably 4 hydrogen bonds.

Without being bound by the present explanation, it may be thought that the ureidopyrimidone species of formula (Ia) are capable of generating a crosslinked network by physical associations between molecules/polymers. Since the crosslinking is a physical crosslinking, it is possible for the effect to be remanent while at the same time allowing the products to be removed during makeup removal. The removal of the deposit may consist especially in rinsing with a cleansing composition applied at room temperature or at a temperature above 25° C., or in using a makeup remover, a shampoo, or in using any known hydrogen bond breaker.

Many compounds that incorporate ureidopyrimidone units (unit of formula (Ia)) have been described in the literature and studied for their self-assembly property by fundamental research laboratories.

In the cosmetic field, mention may be made of WO 02/098, 377, which describes, in a general manner, compounds bearing ureidopyrimidone units for cosmetic applications to the skin and the hair. Mention may also be made of WO 2003/032,929 which describes the preparation of supramolecular polymers and the use thereof in hair applications. Mention may also be made of WO 2004/016,598, which describes the preparation of supramolecular polymers and their use in varied applications including cosmetic applications; or alternatively WO 2005/042,641, which describes the preparation of supramolecular polymers, especially of polyurethane type, and their use in varied applications including cosmetic applications.

The present invention allows the reversible and long-lasting anchoring of a cosmetic active agent at the surface of a keratin material, especially the hair, the eyelashes, the nails or the skin, using a double-action system which may be referred to as a supramolecular "anchored base (referred to hereinbelow as a basecoat)–topcoat". This anchoring may be obtained by functionalization of the surface of the keratin material with supramolecular units capable of creating associations with active agents that are also functionalized with supramolecular units.

This supramolecular "basecoat-topcoat" system may consist especially in:
- in a first stage, functionalizing by covalent chemical grafting, at the surface of the keratin material (for example hair or skin), of a graftable species bearing one or more supramolecular units, said units being capable of associating via at least 3 hydrogen bonds with another supramolecular unit; this unit being the ureidopyrimidone unit;
- in a second stage, depositing on the keratin material thus functionalized varied cosmetic active agents (for example a dye, fatty chain, hydrophilic unit, silicone or UV-screening agent) covalently bonded to at least one supramolecular unit, capable of associating via at least 3 hydrogen bonds with the above supramolecular units, these units being ureidopyrimidone units.

These two actions may be performed simultaneously by applying a topcoat+basecoat mixture to the keratin materials; or sequentially by first applying the basecoat and then the topcoat.

The active agents finally present on the keratin materials, after the process has been performed, may have the advantage of withstanding attack such as that caused by shampooing, disentangling or pollution, and of being able to be removed via the action of a specific stimulus for destroying the supramolecular interactions (for example heat or an alcoholic solvent). After removal of the active agent, the supramolecular functions are still present and a new cosmetic active agent may then be recombined without the need to functionalize the keratin substrate again.

Another advantage of the present invention lies in the possibility of combining different cosmetic active agents together, provided that they are functionalized with an ad hoc supramolecular unit.

By means of the present invention, it may be envisaged in the field of haircare to improve the properties of the hair, to combat damage suffered, to moisturize, care for and reinforce or even repair keratin materials, and to give them long-lasting softness, color and sheen so that the effect remains perceptible after shampooing at least once.

The expression "strengthening of keratin materials" especially means an improvement in the mechanical properties which may be reflected by:
- an increase in their rigidity, which gives them greater strength and body; or
- a decrease in their deformation, in particular under wet conditions, which allows the hair, for example, to readily return to its initial shape once dried, and is reflected by an improvement in the dynamics of the hair; or
- better resistance to tensile mechanical forces which are applied thereto, for example during combing, and which can lead to breaking of the hair;
- a decrease in its porosity or in its swelling in water. Indeed, it is known that hair damaged by oxidizing, reducing or alkaline treatments is more porous than undamaged hair, which is reflected by faster diffusion of water further into the core and has the effect of increasing the diameter of the hair in a wet environment (The Science of Hair Care, p. 416, 2nd edition, ed. C. Bouillon, J. Wilkinson, 2005).

By means of the present invention, it may also be envisaged in the field of makeup to provide, for example, long-lasting and if possible reversible color. It may also be envisaged for the consumer to envisage combining different effects, for example a color change, or to combine the color with another cosmetic care treatment, for instance antisun protection.

The cosmetic treatment process according to the invention thus consists in applying to keratin materials, for example to natural hair or hair treated with a cosmetic treatment:
- in a first stage, at least one graftable species comprising at least one unit (Ia) which is capable of associating via at least 3 hydrogen bonds with another unit (Ia) (basecoat);
- in a second stage, at least one cosmetic active agent, especially for haircare, covalently bonded to a unit (Ia) which is capable of associating via at least 3 hydrogen bonds with the units (Ia) of the graftable species deposited on the keratin materials in the preceding step (topcoat).

This second step may be renewed as many times as desired, the "topcoats" possibly being moved and exchanged with "topcoats" bearing other cosmetic active agents under the action of one or more stimuli that are capable of breaking the hydrogen bonds (for example thermal, or action of a solvent).

In order to "move" the cosmetic active agent and to cancel its effect, a topcoat free of cosmetic active agent may be used. It will preferably consist of an "active agent" free of cosmetic effect covalently bonded to at least one unit capable of associating via at least 3 hydrogen bonds with the unit of the basecoat.

The chemical unit capable of associating via at least 3 hydrogen bonds, whether this is in the basecoat or in the topcoat, comprises at least one unit of formula (Ia) (also known as ureidopyrimidone).

The Graftable Species

The graftable species comprising at least one unit of formula (Ia), which may be used in the cosmetic composition forming the basecoat, is preferably chosen from the compounds of formula (II), and salts and solvates thereof:

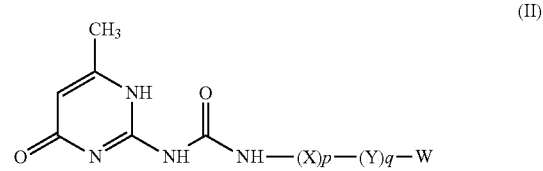

(II)

in which:
X represents a linear or branched, saturated or unsaturated, divalent C1-C30 hydrocarbon-based chain, optionally interrupted with and/or bearing, at one or both of its ends, one or more divalent groups chosen from —N(R)—, —N$^+$(R)(R')—, —O—, —S—, —C(O)—, —SO$_2$—, and an aromatic or non-aromatic, saturated or unsaturated, fused or non-fused divalent C3-C7 (hetero) cyclic radical, optionally comprising one or more identical or different heteroatoms chosen from N, S and O, optionally substituted with OH or NR"R'";

with R and R', which may be identical or different, chosen from a hydrogen, a linear or branched, saturated or unsaturated C1-C4 alkyl radical, optionally substituted with OH and/or NR"R'", with R" and R'", which may be identical or different, chosen from H and a linear or branched, saturated or unsaturated C1-C4 alkyl radical;

p is equal to 0 or 1;
q is equal to 0 or 1;
Y represents a linear, branched and/or cyclic, saturated or unsaturated divalent C1-C18 hydrocarbon-based chain, optionally substituted with OH and/or NR"R'", W represents a unit for grafting onto keratin materials and may especially represent:
(i) a thiol,
(ii) a protected thiol of formula —S—Pr with Pr representing:
a) a protecting group such as a saturated or unsaturated, fused or non-fused, aromatic or non-aromatic C5-C6 heterocycle, optionally comprising N, O, S and/or P heteroatoms;
b) an sp$^2$ carbon protecting group and especially a group of formula —C(O)R1 with R1 representing an alkyl especially of C1-C12, an O-alkyl especially of C1-C12, an aromatic ring or heterocycle; or a group of formula —C(NR'1)NHR'2 with R'1 and R'2, which may be identical or different, chosen from a hydrogen, a linear or branched, saturated or unsaturated C1-C4 alkyl radical, optionally substituted with OH, and salts thereof (for example chloride, bromide); such a preferred group is the isothiouronium group of formula —S—C(NH)NH$_2$,
c) an sp$^3$ carbon protecting group and especially a group of formula —CX$_3$, with X, which may be identical or different, representing O-alkyl, S-alkyl or H, with alkyl especially of C1-C12;
d) a metal protecting group, especially a group of formula -Met-X$_n$ or -Met(M$_m$)—X$_n$, with "Met" representing a metal chosen from Mg, Ca, Sr, Ba, La, Ti, Zr, V, Cr, Mo, W, Mn, Fe, Co, Rh, Ni, Pd, Pt, Cu, Ag, Au, Zn, In Sn and Bi; X representing O-alkyl, N-alkyl or S-alkyl with alkyl especially being C1-C12; M representing O, N or S; and n and m being integers such that (1+2m+n) is equal to the valency of the metal Met;

e) a substituted sulfur atom protecting group, f) a photosensitive protecting group such as nitrobenzyl or benzylsulfonyl aromatic groups;

(iii) a nucleofugal group; mention may be made especially of the following groups: Cl, Br, F, —OSO3M, —OSO2 alkyl*, —OSO2CF3, —OSO2 aryl, —OSO2N(alkyl*)2, —OR1, SR2, —SOR2, —SO2R2, —S+R2R3, —SCN, —SCOOR2, —NR2R3, N+R2R3R4,

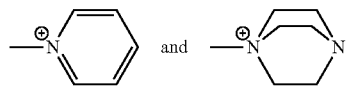

M representing a hydrogen atom, an alkali metal or alkaline-earth metal or an ammonium residue, R1 represents a C1-C4 alkyl radical, a substituted or unsubstituted phenyl radical, the radical $PO_3H_2$ and salts thereof, or the acetyl radical, R2, R3 and R4, which may be identical or different, represent a C1-C4 alkyl radical or a substituted or unsubstituted phenyl radical, the alkyl* group denoting a C1-C4 radical optionally substituted with an OH group; the aryl group denoting a phenyl group, optionally substituted with one or more linear or branched C1-C4 alkyl radicals, with one or more halogen atoms chosen from Cl, Br, I and F, or with one or more methoxy, nitro or —$CF_3$ groups, (iv) a group containing one or more activated carbons or activated bonds; mention may be made especially of the following groups:

epoxide, aziridine, vinyl and activated vinyls, derived from the following compounds: acrylonitrile, acrylic and methacrylic esters, acrylamides and methacrylamides, crotonic acid and ester, cinnamic acid and ester, styrene and derivatives thereof, butadiene, vinyl ethers, vinyl ketone, maleic esters, maleimides and halomaleimides, vinyl sulfones or precursors thereof, β-halo or β-sulfatoethyl sulfones, cyclic carbonates, oxazine, oxazoline, oxazinium, oxazolinium, imidazolium or thiazolidinium, carboxylic acid halides (especially the —CO—Cl group) or sulfonic acid halides (especially the —$SO_2$—Cl group), esters, carbamates (especially the group —CO—O—CO—R'), anhydrides, isothiocyanates and isocyanates, lactones, thiolactone;

azalactones of structure:

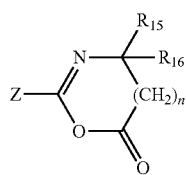

in which:

Z represents the residue of an active compound,

R15 and R16, which may be identical or different, represent a hydrogen atom, a C1-C12 alkyl, C3-C12 cycloalkyl, C5-C12 aryl or C6-C26 arenyl radical comprising from 0 to 3 heteroatoms chosen from S, N and O, or alternatively R15 and R16 together form a carbocycle containing from 4 to 12 atoms and n is an integer between 0 and 3, etc.

the halide functions of an unsaturated ring, the ring possibly being a carbocycle or a heterocycle of formula —RX, R being an unsaturated carbocyclic radical or an unsaturated heterocyclic radical, optionally substituted with a halogen atom such as Cl or Br and X denoting I, Br or Cl. Examples that may be mentioned include chlorotriazine, chloropyrimidine, chloroquinoxaline, chlorobenzotriazole, dichloro-triazine, dichloroquinoxaline and dichloropyrimidine functions.

the functions of formula —$SO_2X$, in which X denotes F, Cl (sulfonyl ides); —$OSO_3R'$, in which R' denotes H or an alkyl radical; —$SO_2R''$ in which R'' denotes H, an alkyl or aryl radical; —$N^+(R''')_3$ in which R''' denotes an alkyl or aryl radical; —$OPO(OR'''')_2$ in which R'''' denotes H or an alkyl radical;

(v) a group containing one or more siloxanes, such as:

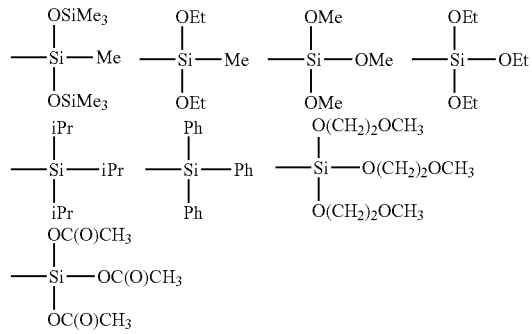

A preliminary step of activation of the hair may prove to be necessary in certain cases. The step of activation of the hair is especially a step of physical, chemical or physical and chemical activation.

The physical activation of the hair may consist in subjecting the hair to heat, electromagnetic waves, electric fields, acoustic waves or plasmas.

The chemical activation of the hair may be reducing or non-reducing.

The creation of the covalent bond between the graftable species and the activated hair may be obtained after a nucleophilic, electrophilic or radical substitution reaction, an addition reaction to carbon-carbon or carbon-heteroatom double bonds or triple bonds, or a ring-opening reaction.

The reaction between the graftable species and the activated hair may take place spontaneously. This reaction may also be performed via activation with a reducing agent, temperature, pH, a coreagent or a chemical catalyst, and preferably with a reducing agent.

As agents for reducing hair keratin, the following may be mentioned, without this list being limiting:

thiols such as thioglycolic acid, thiolactic acid, 3-mercaptopropionic acid, thiomalic acid, 2,3-dimercaptosuccinic acid, cysteine, N-glycyl-L-cysteine, L-cysteinylglycine and also esters and salts thereof, thioglycerol, cysteamine and C1-C4 acyl derivatives thereof, N-mesylcysteamine, N-acetylcysteine, N-mercaptoalkylamides of sugars such as N-(mercapto-2-ethyl)gluconamide, pantetheine, the N-(mercaptoalkyl)-ω-hydroxyalkylamides described in patent application EP-A-354 835, the N-mono- or N,N-dialkylmercapto-4-butyramides described in patent application EP-A-368 763, the aminomercaptoalkyl amides described in patent application EP-A-432 000, the derivatives of N-(mercaptoalkyl)succinamic acid and N-(mercaptoalkyl)succinimides described in patent application EP-A-465 342, the alkylamino mercaptoalkyl amides described in patent application EP-A-514,282, the azeotropic mixture of 2-hydroxypropyl thioglycolate and of (2-hydroxy-1-methyl)ethyl thioglycolate described in patent application FR-A-2,679,448, mercaptoalkylamino amides described in patent application FR-A-2,692,481, and the N-mercaptoalkylalkanediamides described in patent application EP-A-653 202;

hydrides such as sodium borohydride or potassium borohydride;

alkali metal or alkaline-earth metal sulfites or bisulfites;

phosphorus derivatives such as phosphines or phosphites;

hyperbranched polymers and dendrimers bearing thiol end functions, such as those of formula:

in which:
Y represents an oxygen atom or an NH group,
A represents a linear, branched or cyclic, saturated or unsaturated C1-C12 alkanediyl group;
this alkanediyl group may be optionally interrupted with one or more heteroatoms, such as O or N;
this alkanediyl group may be optionally substituted with a function as follows:
  amino: —$NH_2$, optionally in the form of a mineral or organic acid salt,
  acylamino: —NH—COR, in which R represents a linear, branched or cyclic, saturated or unsaturated C1-C10 alkyl group,
  carboxylic acid,
  C1-C10 ester;

X represents a nucleophilic group.

According to a particularly preferred embodiment of the process according to the invention, a phosphine or a phosphine salt of a mineral or organic acid is used as reducing agent.

Among the phosphines that lead to particularly advantageous results regarding the formation of reactive sites at the surface of the keratin fibers of the hair, mention may be made of those of formula:

In which R1, R2 and R3, which are identical, represent —(CH2)n-CH3; —(CH2)m-CRR—OR; —(CH2)n-COOR; —(CH2)n-CONRR' or —(CH2)n-NRR' with n=1 to 3; m=0 to 3; and R and R', which may be identical or different, represent a hydrogen atom or a linear or branched C1-C4 alkyl radical and the salts of said compounds.

Among the phosphine salts, mention may be made especially of hydrochlorides, hydrobromides, sulfates, citrates, oxalates and acetates.

Among the phosphines that are particularly preferred, mention may be made especially of tris(2-carboxyethyl) phosphine or tris(hydroxymethyl)phosphine which especially have the advantage of being odourless and water-soluble, but also stable with respect to oxygen.

Advantageously, W represents a thiol or a protected thiol as described previously.

Preferably, W represents an isothiouronium group of formula —S—C(NH)$NH_2$, especially in the form of salts, for example chloride (obtained by addition of hydrochloric acid).

Hair mainly consists of protein (from 65% to 95%). The other constituents are mainly water, lipids and melanin pigments. The protein consists of natural amino acids, some of which bear nucleophilic side chains capable of reacting with the graftable species described previously.

The main amino acids bearing nucleophilic groups and which are present in the hair are listed in the table below, along with examples of bonds formed with examples of graftable species described previously.

| Name | Structure | Reactive function of the hair | Example of reactive function of the graftable species | Bond formed |
|---|---|---|---|---|
| Cysteine | 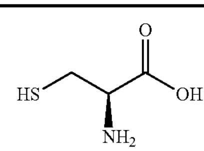 | RSH or RS— | R'—SH, R'—SC(NH)NH2, HCl | RSSR' |

-continued

| Name | Structure | Reactive function of the hair | Example of reactive function of the graftable species | Bond formed |
|---|---|---|---|---|
| Lysine | H2N–...–C(O)OH with NH2 | RNH2 | R'C(O)Cl, R'C(O)OC(O)R' R'OSO2CH3 epoxide | RNHC(O)R' RNHR' |
| Serine | HO–...–C(O)OH with NH2 | ROH or RO— | epoxide | R–O–CH2–CH(OH)–R' |
| Threonine | HO–...–C(O)OH with NH2 | | Br–CH2CH2–R' | R–O–CH2CH2–R' |
| Tyrosine | HO–Ar–...–C(O)OH with NH2 | ArOH or ArO— | RSO2Cl | ArOSO2R' |

Advantageously, the grafting species reacts with the hair cysteine or cystine (disulfide form). Thus, the covalent bond formed by the grafting is advantageously a disulfide bond.

Among the compounds capable of activating the hair in a non-reducing manner, mention may be made of oxidizing agents, acids and bases.

Oxidizing agents that may be mentioned, in a non-limiting manner, include hydrogen peroxide, bromates and persalts.

Acids that may be mentioned, in a non-limiting manner, include hydrochloric acid, citric acid and tartaric acid.

Bases that may be mentioned, in a non-limiting manner, include sodium hydroxide, ammonia and alkanolamines.

Among the compounds of formula (II) that are particularly preferred, mention may be made of the following compounds:

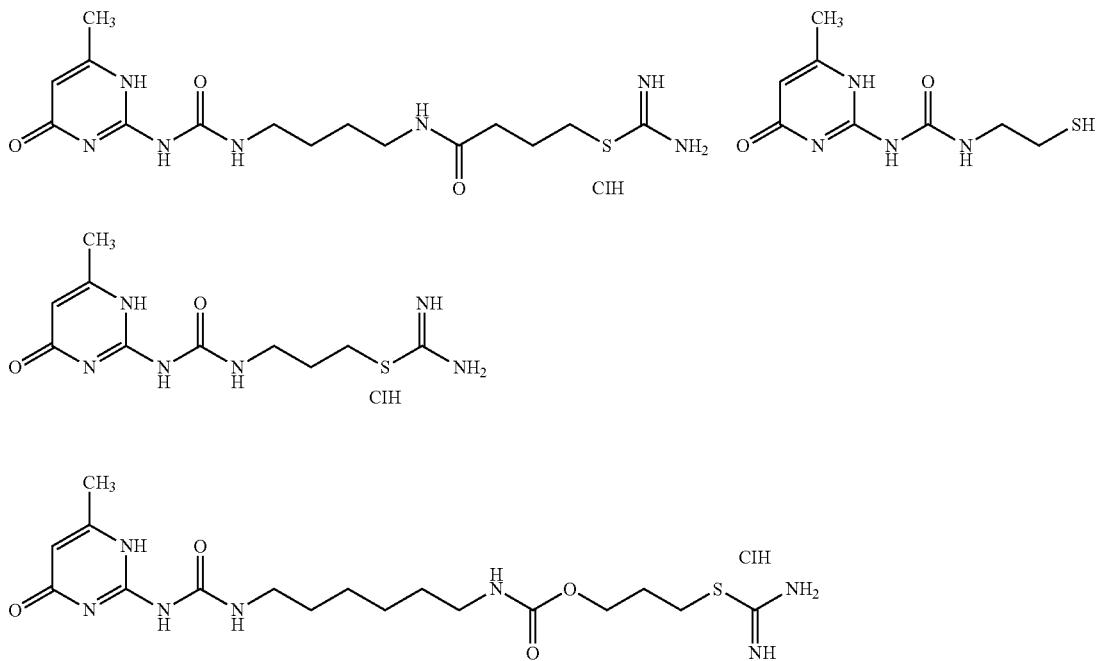

-continued
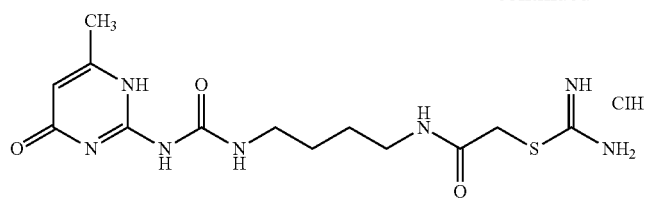
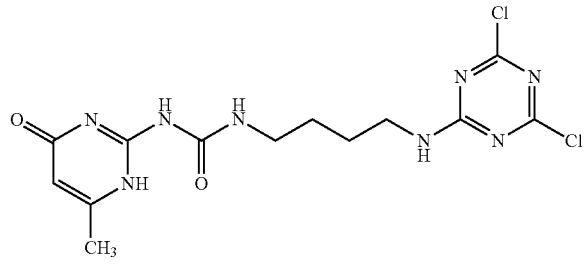
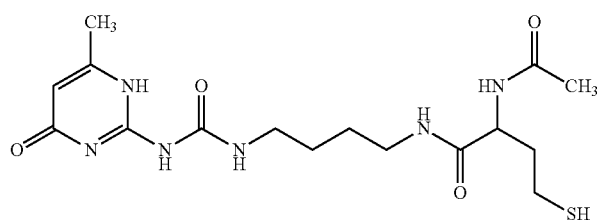
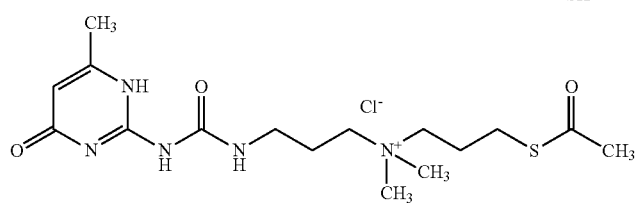
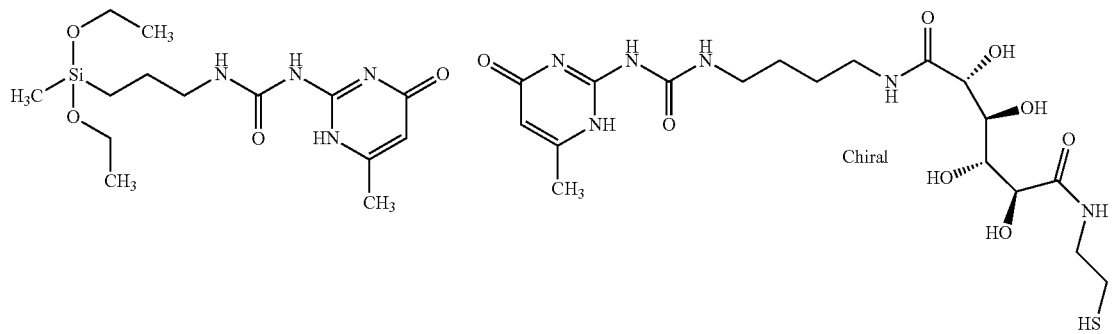
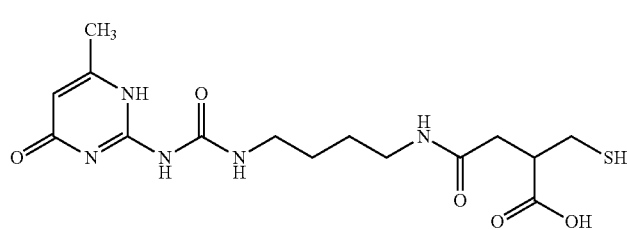
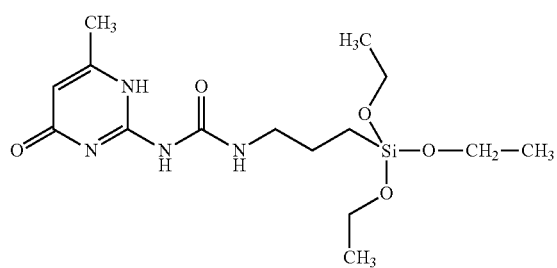

-continued

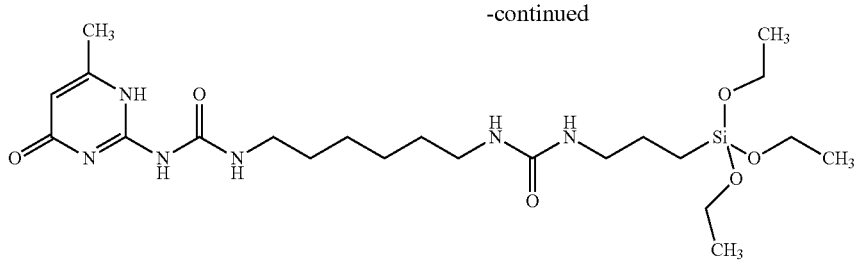

The compounds bearing an isothiouronium group described previously are preferred.
In particular, the compound of formula:

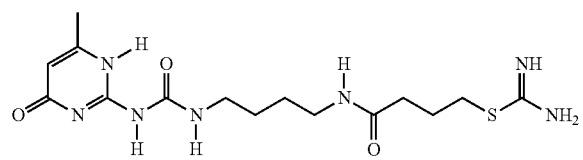 [SMILES: Cc1cc(=O)nc(NC(=O)NCCCCNC(=O)CCCSC(=N)N)[nH]1]

especially in hydrochloride salt form (HCl).

Thiol-protecting groups are particularly described in WO 00/40210.

Preferably, the graftable species may be included in an amount of from 0.1% to 10% by weight and especially 0.5% to 5% by weight in the composition comprising it (especially the basecoat).

Cosmetic Active Agents

The cosmetic active agents bearing at least one unit of formula (Ia) that may be used in the cosmetic composition according to the invention (topcoat) are defined below.

In the present invention, the term "cosmetic active agent" means any compound, polymer or molecule that is capable of giving a cosmetic effect, including color, to keratin materials.

In particular, these cosmetic active agents may be chosen from the following compounds, alone or as a mixture:
 cosmetic active agents for caring for keratin fibers; especially those of formula (III),
 dyeing active agents, especially direct dyes and fluorescent dyes;
 polymeric hydrophilic chains;
 silicone chains;
 fatty substances, especially "supramolecular" oils and waxes;
 UV-screening agents,
 hyaluronic acid,
 capsules;

it being understood that these cosmetic active agents bear at least one unit of formula (Ia).

1/The cosmetic active agents for caring for keratin fibers preferably correspond to formula (III), and also the salts, addition salts, isomers, solvates, especially hydrates, and tautomeric forms thereof:

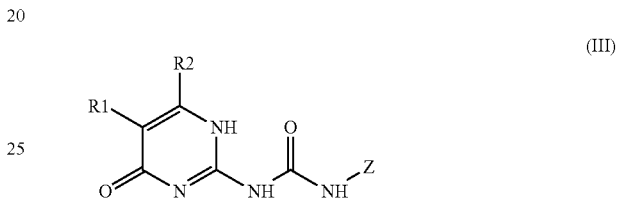

(III)

in which R1=H and R2=methyl.

Z represents a monovalent radical chosen from:
(i) a linear or branched C9 to C32 and especially C9-C22 (saturated) alkyl radical;
(ii) a linear or branched C9 to C32 and especially C9-C22 (unsaturated) alkene radical;
said radicals possibly being substituted with 1 to 8, especially 2 to 6 or even 3 to 5 groups chosen from —OH, —OR, —SO$_3$H, —SO$_3$R, —SO$_2$NRR', —COOH, —NRR' and —N$^+$RR'R", with R, R' and R"=H or C1-C6 alkyl, especially methyl; and/or said radicals possibly comprising 1 to 8, especially 2 to 6 or even 3 to 5 divalent groups chosen, alone or as a mixture, from —NH— (or =NH), —O—, —C(O)—, —C(=NH)—, —N$^+$(CH$_3$)$_2$-An$^-$ (An$^-$: anion); or alternatively —N=(trivalent).

Advantageously,
Z represents a monovalent radical chosen from:
(i) a linear or branched C9 to C32, especially C9-C22 and in particular C12-C22 (saturated) alkyl radical;
(ii) a linear or branched C9 to C32, especially C9-C22 and in particular C12-C22 (unsaturated) alkene radical.

Among the compounds of formula (III) that are particularly preferred, mention may be made of the following compounds:

(compound P)

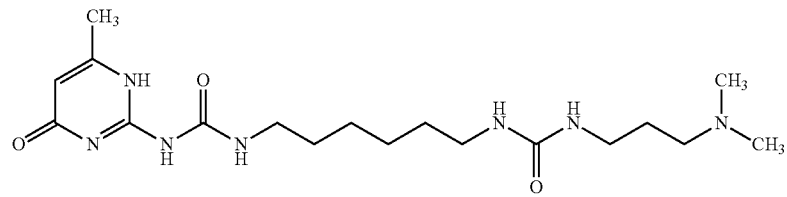

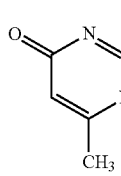

(compound Q)

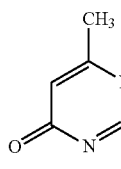

(compound R)

Use is preferably made of compound Q.

2/ the dyeing active agents may be chosen especially from direct dyes and fluorescent dyes, it being understood that these dyeing active agents bear at least one unit of formula (Ia).

In particular, the dyeing active agent may be of formula (I'a): (DYE)n(SAU)m in which:
(DYE) represents any chromophore with a maximum absorption of between 300 nm and 1200 nm, covalently bonded to (SAU),
(SAU) represents a donor/acceptor radical which can form at least three hydrogen bonds, and which is capable of self-associating under suitable conditions,
n and m are integers greater than or equal to 1;
and also the addition salts and solvates thereof.

When n is greater than 1, the (DYE) radicals may be identical or different. When m is greater than 1, the (SAU) radicals may be identical or different. The dyeing active agents of formula (I'a) are described, for example, in patent applications EP 1 310 533 and EP 1 486 539.

As chromophores that may be used in the present invention, mention may be made of radicals derived from the following dyes: acridines; acridones; anthranthrones; anthrapyrimidines; anthraquinones; azines; azos, azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanins (azacarbocyanin, diazacarbocyanin, diazahemicyanin, hemicyanin or tetraazacarbocyanin); diazines; diketopyrrolopyrroles; dioxazines; diphenylamines; diphenylmethanes; dithiazines; flavonoids such as flavanthrones and flavones; fluorindines; formazans; hydrazones, in particular arylhydrazones; hydroxy ketones; indamines; indanthrones; indigoids and pseudo-indigoids; indophenols; indoanilines; isoindolines; isoindolinones; isoviolanthrones; lactones; methines; naphthalimides; naphthanilides; naphtholactams; naphthoquinones; nitro, especially nitro(hetero) aromatics; oxadiazoles; oxazines; perilones; perinones; perylenes; phenazines; phenothiazines; phthalocyanin; polyenes/carotenoids; porphyrins; pyranthrones; pyrazolanthrones; pyrazolones; pyrimidinoanthrones; pyronines; quinacridones; quinolines; quinophthalones; squaranes; stilbenes; tetrazoliums; thiazines; thioindigo; thiopyronines; triarylmethanes; xanthenes.

Among the nitro chromophores that may be used according to the invention, mention may be made, in a non-limiting manner, of the radicals derived from the following dyes:

1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-βγ-dihydroxypropyloxy-3-methylamino-4-nitrobenzene
1-β-hydroxyethylamino-4-β,γ-dihydroxypropyloxy-2-nitrobenzene
1-βγ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo chromophores, mention may also be made of the following compounds, described in the Color Index International 3rd edition:
Disperse Red 17
Acid Yellow 9
Acid Black 1
Basic Red 22
Basic Red 76
Basic Yellow 57
Basic Brown 16

Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone chromophores, mention may be made of radicals derived from the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
and also the following compounds:
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine chromophores, those listed in the Color Index International are suitable for use, for example the radicals derived from the following dyes:
Basic Blue 17
Basic Red 2.

Among the triarylmethane chromophores that may be used according to the invention, mention may be made, besides those listed in the Color Index, of the radicals derived from the following dyes:
Basic Green 1
Acid Blue 9
Basic Violet 3
Basic Violet 14
Basic Blue 7
Acid Violet 49
Basic Blue 26
Acid Blue 7

Among the indoamine chromophores that may be used according to the invention, mention may be made of the radicals derived from the following dyes:
2-β-hydroxyethlyamino-5-[bis(β-4'-hydroxyethyl)amino]anilino-1,4-benzoquinone
2-β-hydroxyethylamino-5-(2'-methoxy-4'-amino)anilino-1,4-benzoquinone
  3-N-(2'-chloro-4'-hydroxy)phenylacetylamino-6-methoxy-1,4-benzoquinone imine
  3-N-(3'-chloro-4'-methylamino)phenylureido-6-methyl-1,4-benzoquinone imine
  3-[4'-N-(ethyl,carbamylmethyl)amino]phenylureido-6-methyl-1,4-benzoquinone imine.

Mention may also be made of the chromophores described in documents U.S. Pat. No. 5,888,252, EP 1,133,975, WO 03/029,359, EP 860,636, WO 95/01772, WO 95/15144 and EP 714,954. Mention may also be made of those described in the encyclopedia "The chemistry of synthetic dye" by K. Venkataraman, 1952, Academic press vol. 1 to 7, in Kirk Othmer's encyclopedia "Chemical technology", in the chapter "Dyes and dye intermediates", 1993, Wiley and Sons, and in various chapters of "Ullmann's encyclopedia of Industrial chemistry" 7th edition, Wiley and Sons.

The preferred chromophores are those which absorb light between 380 nm and 850 nm.

In another embodiment, the dyeing active agent may be of formula (IIb):
(FLUO)n(SAU)m in which:
(FLUO) represents any fluorescent chromophore, covalently bonded to (SAU),
(SAU), m and n having the meaning given above for (I'a),
and also the addition salts and solvates thereof.

When n is greater than 1, the (FLUO) radicals may be identical or different. When m is greater than 1, the (SAU) radicals may be identical or different.

According to the present invention, the term "fluorescent chromophore" means a radical derived from a fluorescent compound. A fluorescent compound is a compound that is capable of absorbing UV or visible radiation at a wavelength $\lambda_{abs}$ of between 250 and 800 nm and capable of re-emitting in the visible range at an emission wavelength $\lambda_{em}$ of between 400 and 800 nm.

Preferably, fluorescent compounds are dyes that are capable of absorbing in the visible range $\lambda_{abs}$ between 400 and 800 nm and of re-emitting in the visible range $\lambda_{em}$ between 400 and 800 nm. More preferentially, fluorescent dyes are dyes that are capable of absorbing at a $\lambda_{abs}$ of between 420 nm and 550 nm and of re-emitting in the visible range at a $\lambda_{em}$ of between 470 and 600 nm.

As fluorescent chromophores that may be used in the present invention, mention may be made of radicals derived from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}bores (BODIPY®), diketopyrrolopyrroles, fluorindines, (poly)methines (especially cyanins and styryls/hemicyanins), naphthalimides, naphthanilides, naphthylamine (such as dansyls), oxadiazoles, oxazines, perilones, perinones, perylenes, polyenes/carotenoids, squaranes, stilbenes, xanthenes.

Mention may also be made of the fluorescent dyes described in documents EP 1,133,975, WO 03/029,359, EP 860,636, WO 95/01772, WO 95/15144 and EP 714,954 and those listed in the encyclopedia "The chemistry of synthetic dye" by K. Venkataraman, 1952, Academic press, vol. 1-7", in Kirk Othmer's encyclopedia "Chemical Technology", in the chapter "Dyes and dye intermediates", 1993, Wiley and sons, and in various chapters of the encyclopedia "Ullmann's Encyclopedia of Industrial Chemistry" 7th ed., Wiley and Sons, in The Handbook—A Guide to Fluorescent Probes and Labeling Technologies, 10th ed. Molecular Probes/Invitrogen; Oregon 2005 circulated on the Internet or in the preceding printed editions.

Dyeing active agents that may also be mentioned include those described in patent application EP 2 083 791.

The radical (SAU) comprises at least one unit of structure (Ia) as defined previously (ureidopyrimidone).

The radicals (SAU) and (DYE) or (FLUO) may comprise one or more linker arms L as a function of the values of n and/or m, such as:
  optionally substituted linear or branched alkylene radicals;
  optionally substituted cycloalkylene radicals;
  optionally substituted arylene radicals;

saturated or unsaturated heterocyclic radicals;

amino radicals (—NH— or —NR—) or alternatively —O—, —SO—, —SO$_2$— or —C(O)—;

and also combinations thereof of the same category and/or of different categories, leading especially to cycloalkylenealkylene, biscycloalkylene, biscycloalkylenealkylene, arylenealkylene, bisphenylenealkylenes, oxyalkylene and aminoalkylene radicals. These radicals may optionally be substituted, especially with one or more C1-C12 alkyl groups, optionally comprising heteroatoms chosen from O, N, S, F and P, and combinations thereof.

Among the optionally substituted alkylene radicals, examples that may be mentioned include C1-C30 alkylene radicals, for example methylene, ethylene, butylene, especially 1,4-butylene, and 1,6-hexylene, and C3-C10 branched alkylene radicals such as 1,4-(4-methylpentylene), 1,6-(2,2,4-trimethylhexylene), 1,5-(5-methylhexylene), 1,6-(6-methylheptylene), 1,5-(2,2,5-trimethylhexylene), 1,7-(3,7-dimethyloctylene), 2,2-(dimethylpropylene) and 1,6-(2,4,4-trimethylhexylene) radicals.

Among the optionally substituted cycloalkylene radicals, mention may be made of cyclopentylene and cyclohexylene radicals, optionally substituted especially with alkyl groups.

Among the cycloalkylenealkylenes, an example that may be mentioned is the isophorone radical.

Among the optionally substituted biscycloalkylenealkylene radicals, examples that may be mentioned include the radicals of formula:

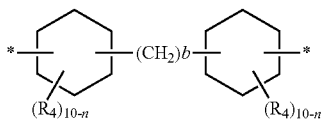

in which b is an integer from 0 to 3 (when b=0, the 2 rings are linked together via a covalent bond), n is an integer from 0 to 4; and R4, which may be identical or different, represents H or a C1-C12 alkyl radical, especially a methyl radical; mention may be made especially of 4,4'-methylenebiscyclohexylene.

Among the optionally substituted arylene radicals, examples that may be mentioned include the phenylene radical, tolylene radicals, especially 2,4- and 2,6-tolylene radicals, and naphthylene radicals, especially 2,4-naphthylene or 2,6-naphthylene.

Among the optionally substituted arylenealkylene radicals, examples that may be mentioned include phenylenealkylene radicals such as the benzylene radical:

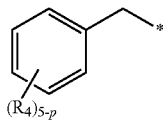

in which p is an integer from 0 to 5.

Among the optionally substituted bisphenylenealkylene radicals, examples that may be mentioned include the radicals of formula (I):

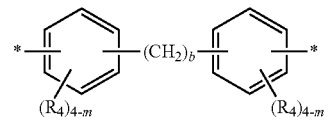

in which b is an integer from 0 to 3 (when b=0, the two rings are linked together via a covalent bond), and m is an integer from 0 to 4; such as the bis-phenylene radical and the 4,4'-methylenebisphenylene radical, and the radicals of formula (II):

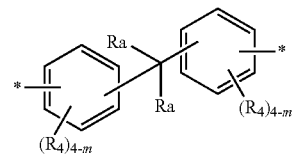

in which m is an integer from 0 to 4, and the radicals Ra, which may be identical or different, represent H or a C1-C4 alkyl radical, preferably a methyl radical.

Among the optionally substituted oxyalkylene radicals, examples that may be mentioned include the alkylene oxide radicals of formula —O—(R'O)y- in which R', which may be identical or different, represents a linear or branched C2-C4 alkylene radical, especially ethylene or propylene; and y is an integer from 1 to 500, preferably from 1 to 200 and more preferably from 5 to 100.

Examples of linker arms that may be mentioned include methylene, ethylene, linear or branched propylene, linear or branched butylene, linear or branched pentylene and linear or branched hexylene radicals, which are optionally substituted and/or interrupted as indicated above.

As examples of saturated or unsaturated, aromatic or non-aromatic rings or heterocycles, interrupting the alkyl radical of the linker arm, mention may be made of phenylene or naphthylene, phenanthrylene, triazinyl, pyrimidinyl, pyridyl, pyridazinyl, quinoxalinyl and cyclohexyl radicals.

Examples of linker arms that may be mentioned include the following radicals:

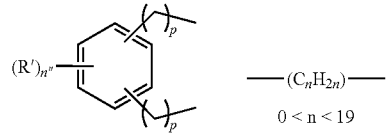

p = 0 or 1
n" = integer of between 0 and 4

——(C$_n$H$_{2n}$)$_2$—X

0 < n < 10
X = NH, NR4, O, S, SO, SO$_2$

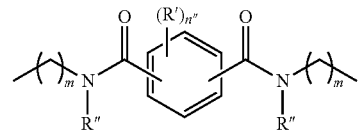

m = integer or between 0 and 6
n" = integer of between 0 and 4

-continued

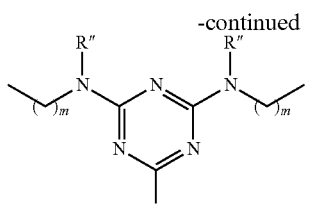

m = integer or between 0 and 6
Z = OH, NR$_8$R$_9$

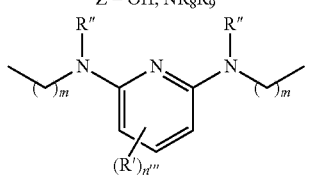

m = integer or between 0 and 6
n''' = integer of between 0 and 3 in which formulae:
(i) R' represents:
an optionally substituted C1-C16 alkyl radical, optionally interrupted with one or more heteroatoms or with one or more groups comprising at least one heteroatom, preferably chosen from oxygen, nitrogen and sulfur, such as CO or SO$_2$, or combinations thereof;
a hydroxyl group,
a C1-C4 alkoxy group,
a C2-C4 (poly)hydroxyalkoxy group,
an alkoxycarbonyl group (RO—CO—) in which R represents a C1-C4 alkyl radical;
an alkylcarbonyloxy radical (RCO—O—) in which R represents a C1-C4 alkyl radical;
an alkylcarbonyl radical (R—CO—) in which R represents a C1-C4 alkyl radical;
an amino group;
an amino group substituted with one or two identical or different C1-C4 alkyl radicals, optionally bearing at least one hydroxyl group; the two alkyl radicals possibly forming, with the nitrogen atom to which they are attached, a heterocycle containing 1 to 3 heteroatoms, preferably 1 to 2 heteroatoms, chosen from N, O and S, preferably N, which is 5- to 7-membered, saturated or unsaturated, aromatic or non-aromatic, and optionally substituted;
an alkylcarbonylamino group (RCO—NR'—) in which the radical R represents a C1-C4 alkyl radical and the radical R' represents a hydrogen atom or a C1-C4 alkyl radical;
an aminocarbonyl group ((R)$_2$N—CO—) in which the radicals R, independently of each other, represent a hydrogen atom or a C1-C4 alkyl radical;
a ureido group (N(R)$_2$—CO—NR'—) in which the radicals R and R', independently of each other, represent a hydrogen atom or a C1-C4 alkyl radical;
an aminosulfonyl group ((R)$_2$N—SO2-) in which the radicals R, independently of each other, represent a hydrogen atom or a C1-C4 alkyl radical;
an alkylsulfonylamino group (RSO2-NR'—) in which the radicals R and R', independently of each other, represent a hydrogen atom or a C1-C4 alkyl radical;
an alkylthio group (RS—) in which the radical R represents a C1-C4 alkyl radical;
an alkylsulfinyl group (R—SO—) in which R represents a C1-C4 alkyl radical;
an alkylsulfonyl group (R—SO2-) in which R represents a C1-C4 alkyl radical;
a nitro group;
a cyano group;
a halogen atom, preferably chlorine or fluorine;
(ii) R'', which are identical, represent a hydrogen atom or a C1-C4 alkyl radical;
(iii) R8 and R9 represent, independently of each other, a hydrogen atom or a C1-C8 alkyl radical optionally substituted with one or more identical or different radicals chosen from hydroxyl, C1-C2 alkoxy, C2-C4 (poly)hydroxyalkoxy, amino, C1-C2 (di)alkylamino and optionally substituted aryl.

Preferably, (DYE) and (SAU) comprise one to three linker arms.

The acid-addition salts may be the salts of addition to an organic or mineral acid such as hydrochloric acid, hydrobromic acid, sulfuric acid or (alkyl- or phenyl-)sulfonic acids such as p-toluenesulfonic acid or methylsulfonic acid, or the salts of carboxylic acids, for instance acetates, lactates, benzoates, salicylates and citrates. The solvates may be hydrates.

The dyeing active agents that may be used may especially correspond to one of the following formulae:

Formula 1

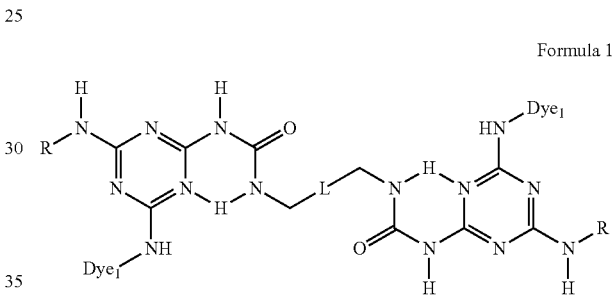

in which:
The groups Dye1 and Dye2 are as defined for (DYE), and R represents a hydrogen atom, a substituted or unsubstituted alkyl group, a substituted or unsubstituted aryl group, a substituted or unsubstituted aralkyl group, a substituted or unsubstituted acyl group, a substituted or unsubstituted sulfonyl group, a substituted or unsubstituted phosphoryl group or a heterocyclic group, and L represents a linker arm as defined previously.

Formula 2

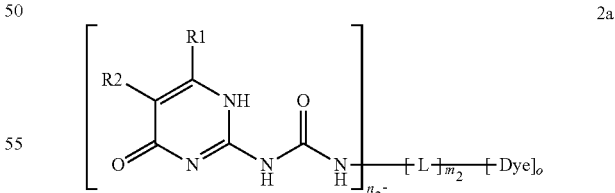

2a

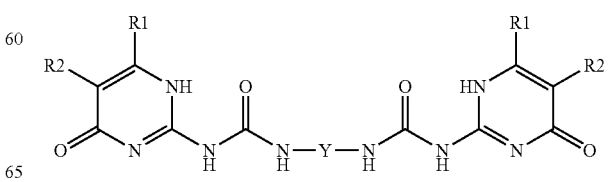

2b in which:
L represents a linker arm;
Dye is as defined previously;
n2 and o, which may be identical or different, are greater than or equal to 1; m2 may be greater than or equal to 0;
R1=H and R2=methyl;
Y represents a divalent DYE group.
Mention may in particular be made of the dyeing active agents below:
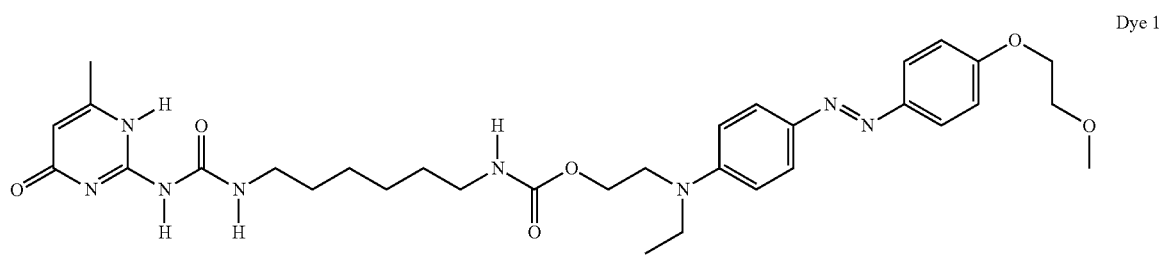
Dye 1
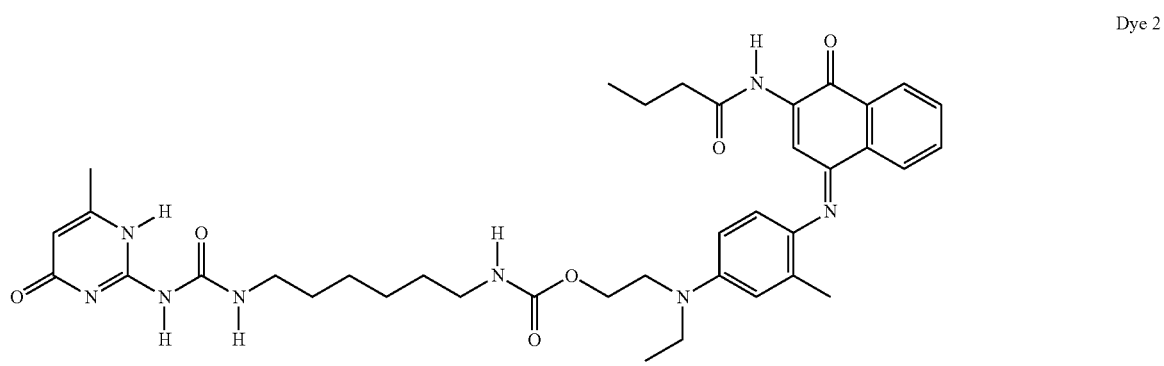
Dye 2
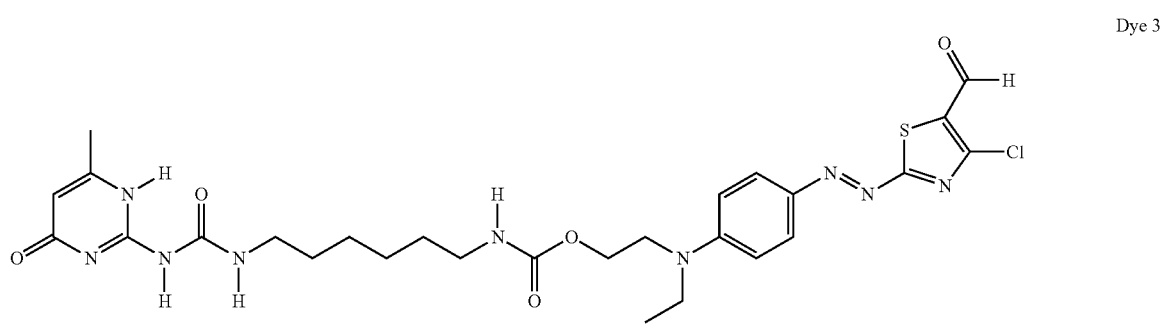
Dye 3
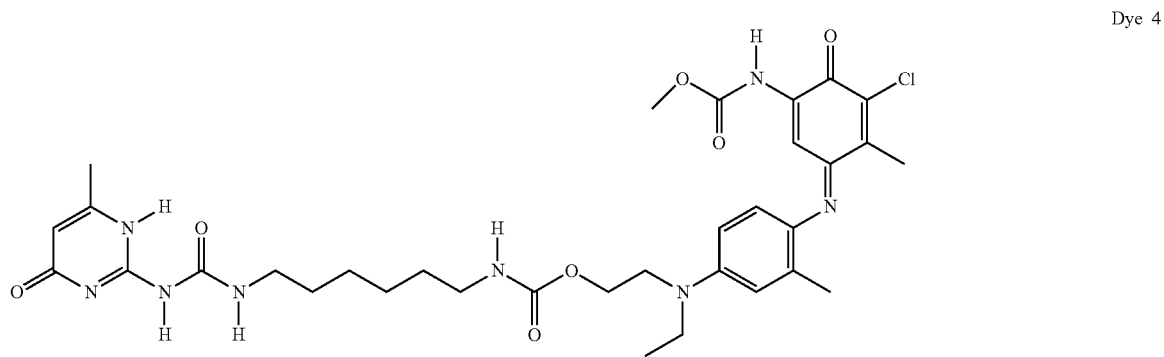
Dye 4

-continued
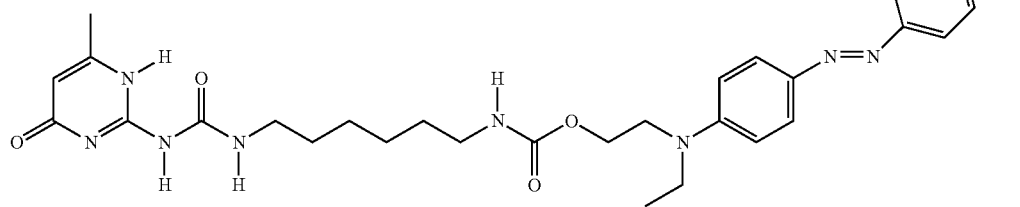
Dye 5
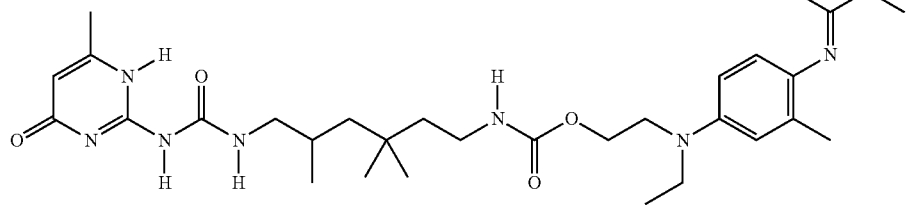
Dye 6
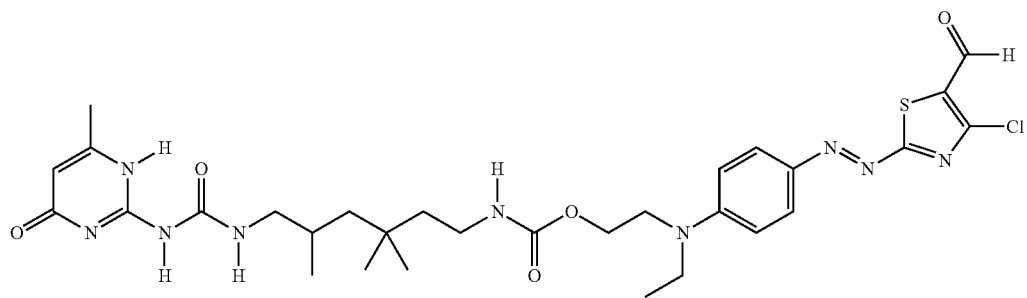
Dye 7
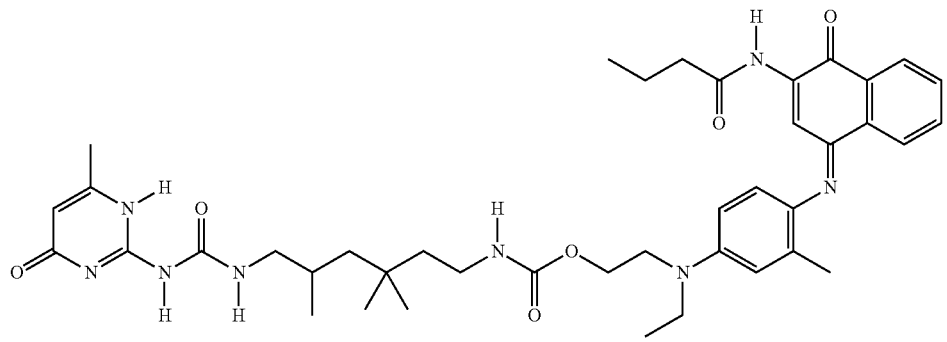
Dye 8
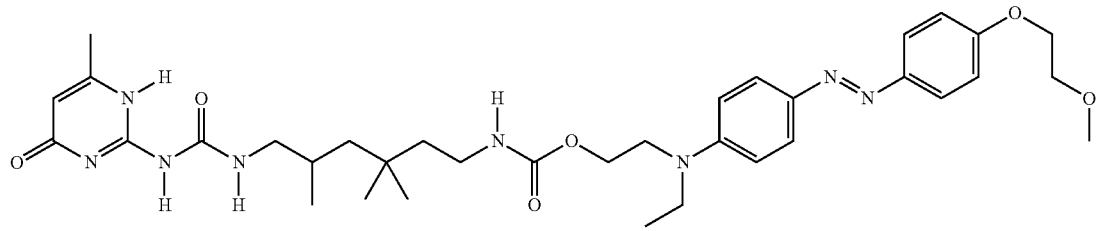
Dye 9

Dye 10
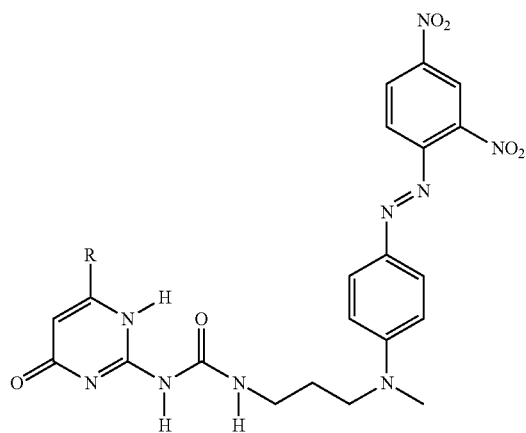
Dye 12
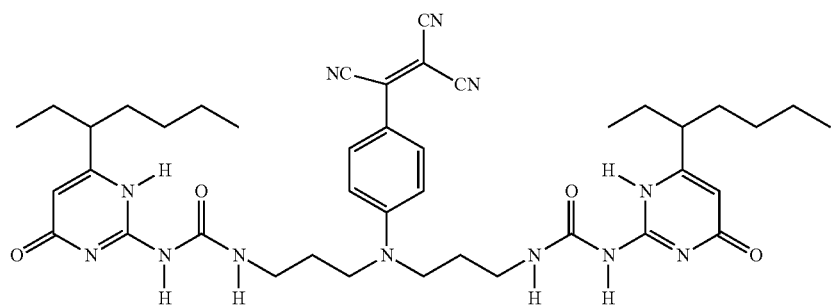
Dye 13
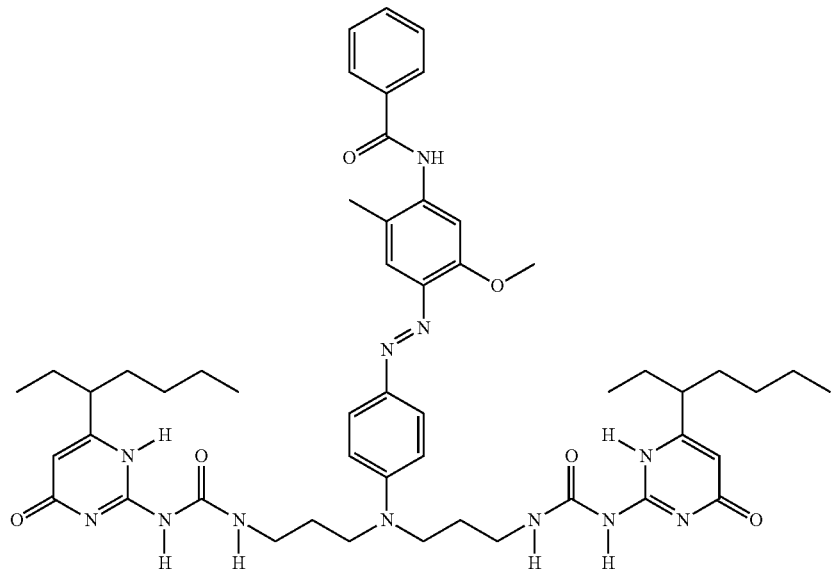

-continued
Dye 14
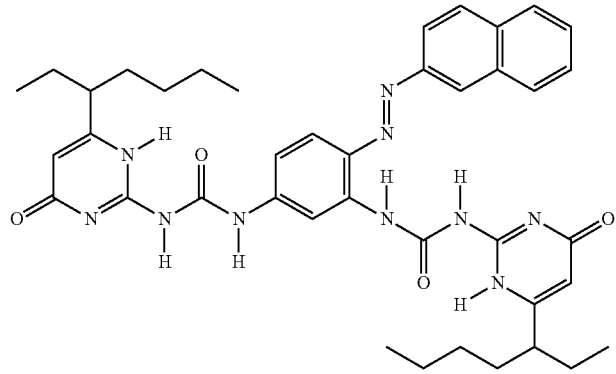
Dye 15
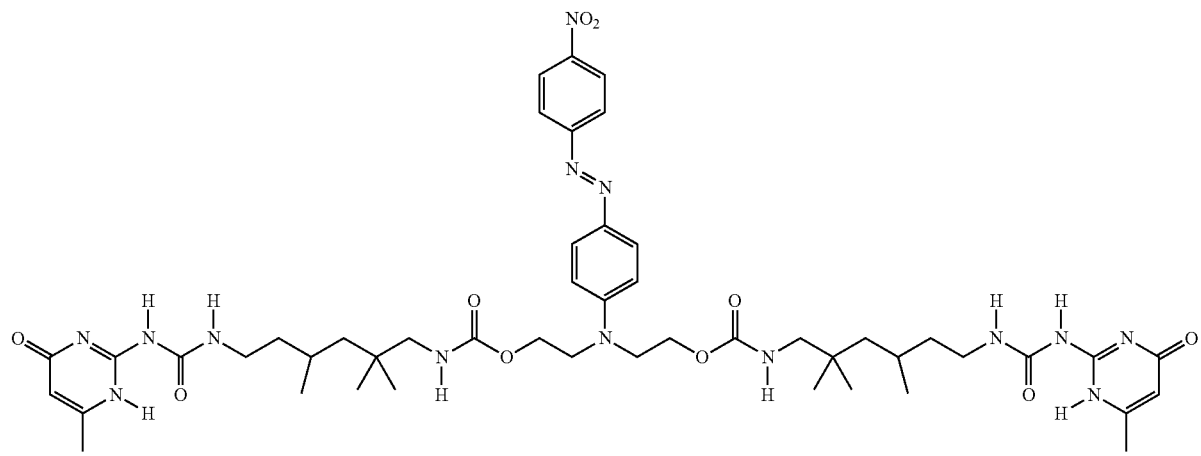
Dye 16
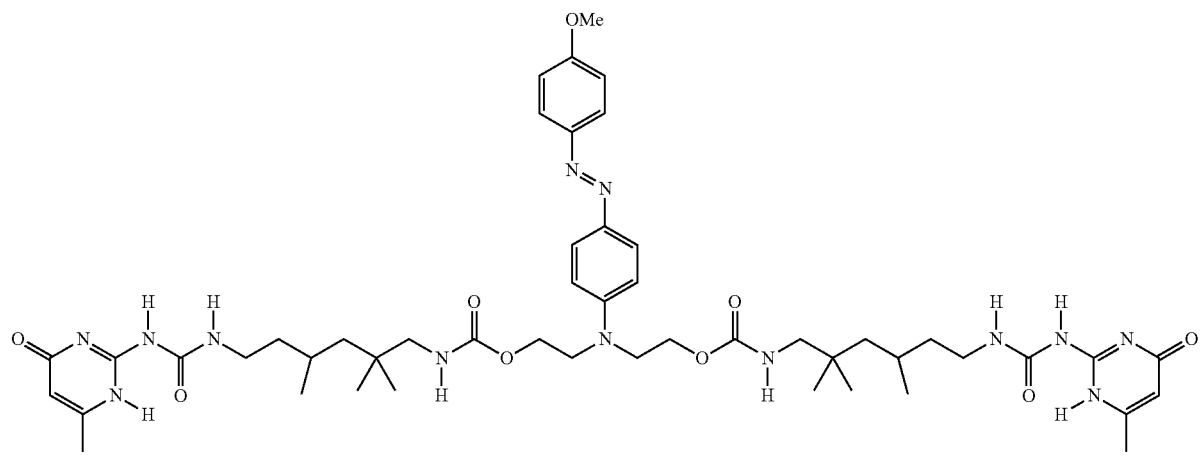
Dye 17
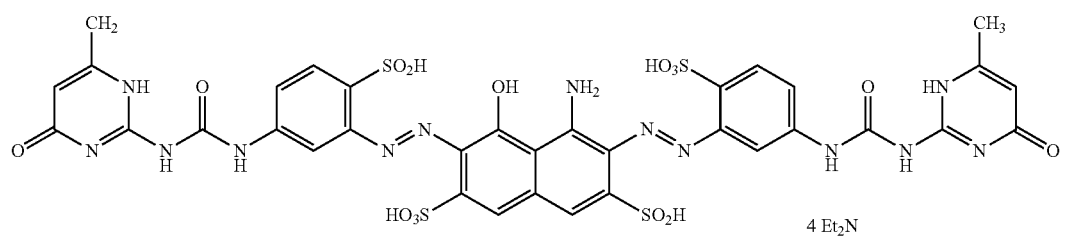

-continued
Dye 18
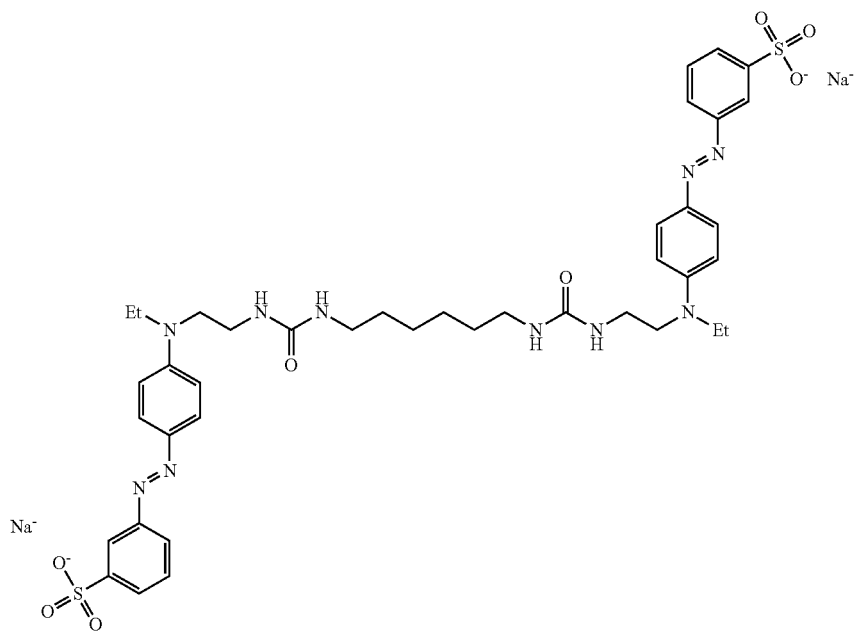
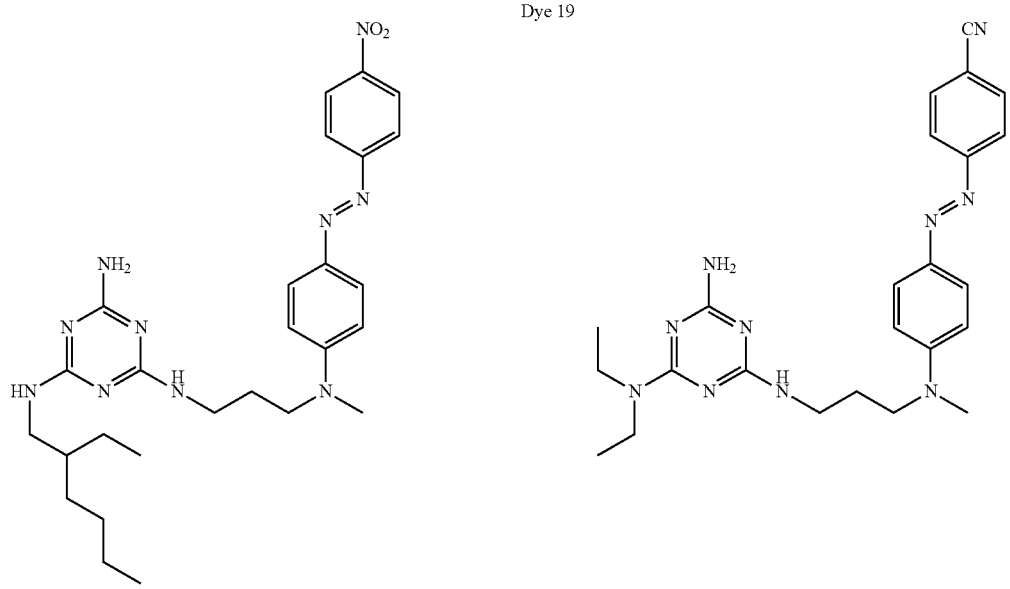
Dye 19
Dye 20

-continued
Dye 21
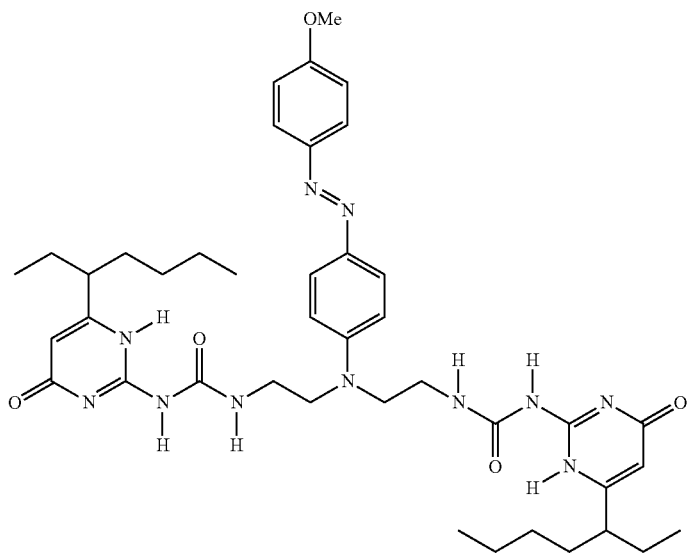
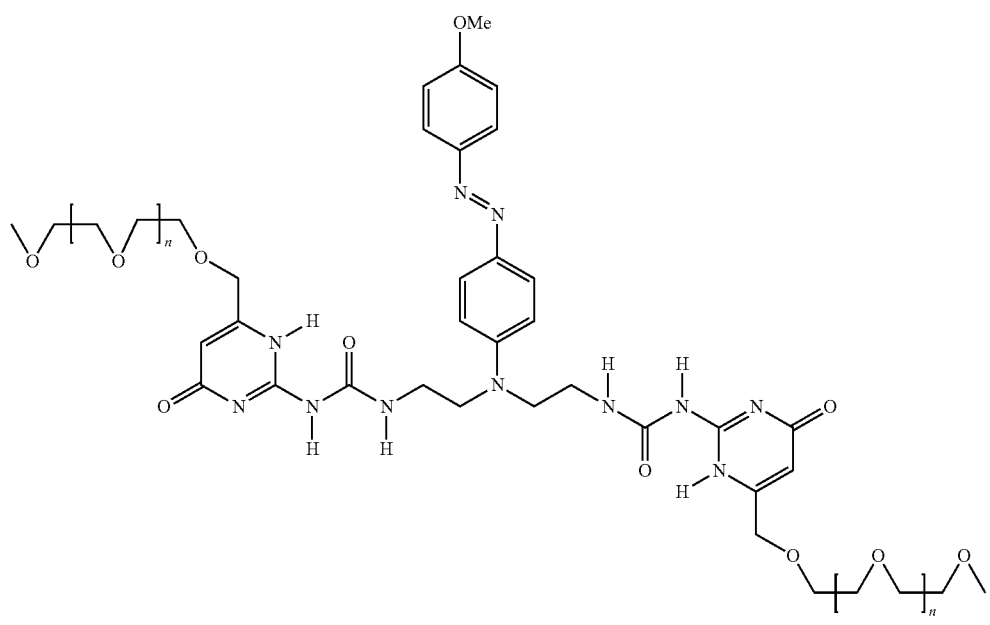
n = 2

-continued
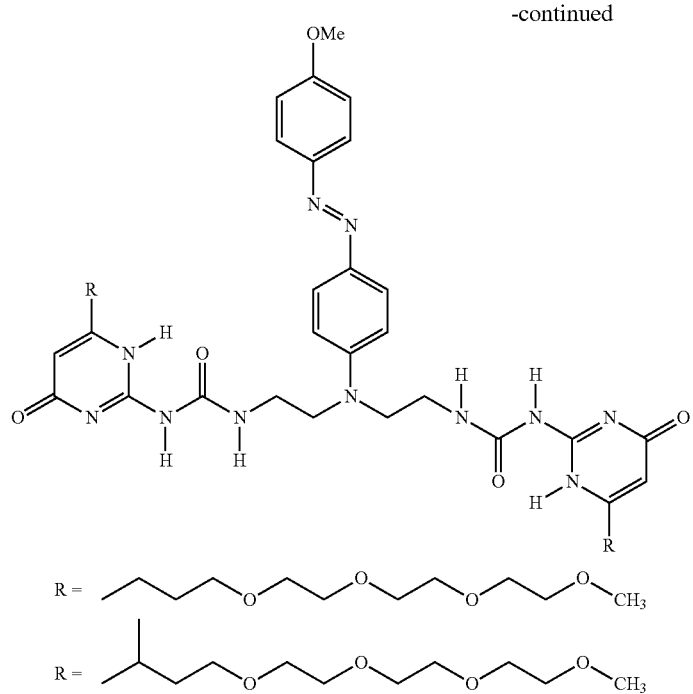
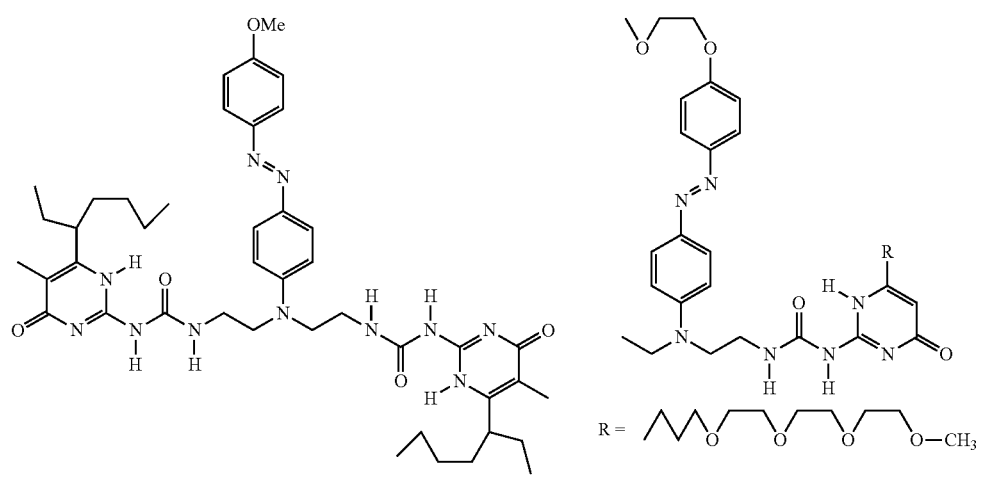
Dye 29
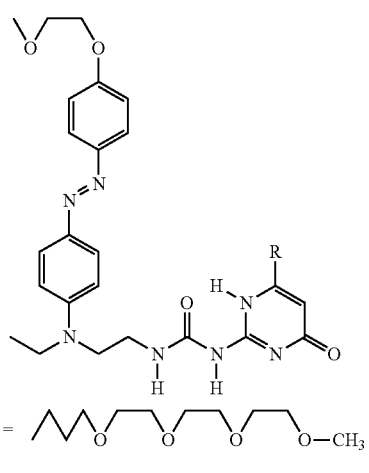
Dye 30
with R=—(CH2)4-(OCH2CH2)3-O—CH3.
A preferred dye that may be used is:
isopropyl-4-oxo-1,4-dihydropyrimidin-2-yl)amino]
carbonyl}amino)hexyl]carbamate of formula:

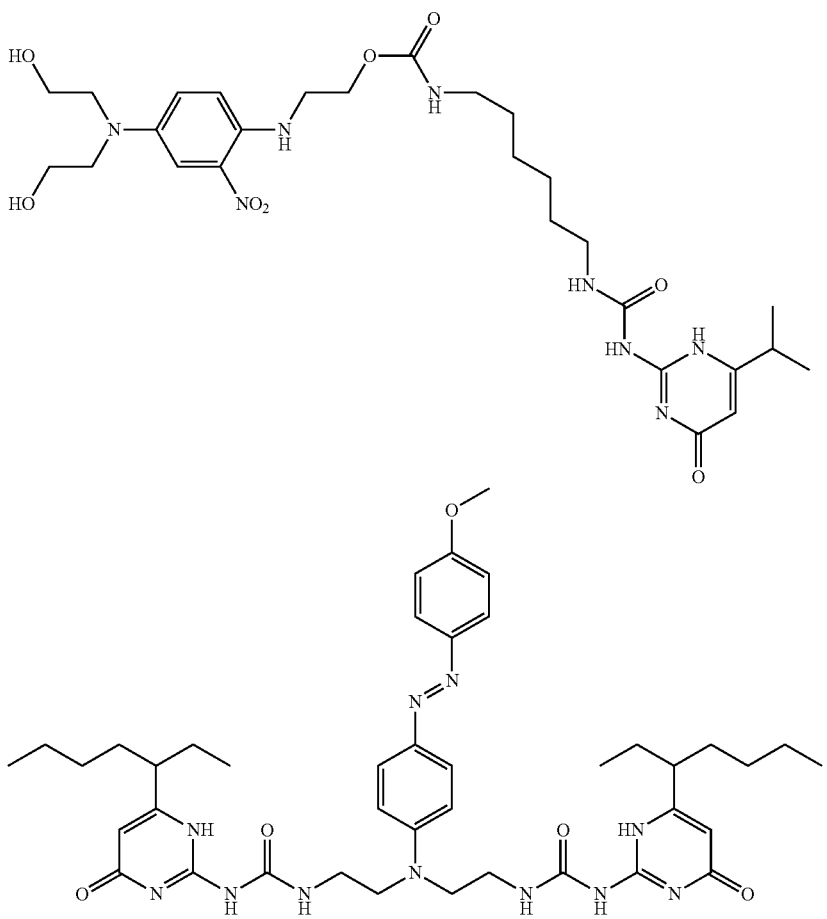

The dye of Example 13 described below.

3/Polymeric Hydrophilic Chains

Hydrophilic chains are characterized in that they contain a repetition of monomer units whose log p is less than 2 and preferably less than 1; it being understood that these chains bear at least one unit of formula (Ia).

These chains preferably have a number-average molecular mass (Mn) of between 200 and 100 000 g/mol, better still between 250 and 50 000 g/mol and even better still between 300 and 50 000 g/mol.

The following may especially be mentioned:

water-soluble synthetic polymers, for instance the following backbones: polyvinylpyrrolidone, polyvinyl alcohol (partially or totally deprotected), polyvinylamine (partially or totally deprotected), polyvinylpyrrolidone, polyvinyl methyl ether, polyvinyl aryl sulfonate, polyalkyl(methyl or ethyl)oxazoline, polyallylamine, polydiallylamine, polydimethyldiallylammonium chloride, polyethylene oxide (PEG) or copolymers thereof, especially PEG/PPO (with a PEG content of greater than 25% relative to the PPO in terms of the number of repeating units), polyacrylic acid, poly(N,N-dimethylacrylamide), poly(hydroxyethyl methacrylate), poly(hydroxypropylmethacrylamide), and copolymers thereof;

oligosaccharides, polysaccharides such as dextran, dextran sulfate, amylose, hydroxypropylcellulose, glycoaminoglycans (chondroitin sulfate), hyaluronic acid, xanthan gum, alginate, chitosan or inulin;

polyamino acids, for instance poly(glutamic acids), polylysine, polyornithine or polyarginine, and copolymers thereof.

Use is preferably made of the compound of formula:

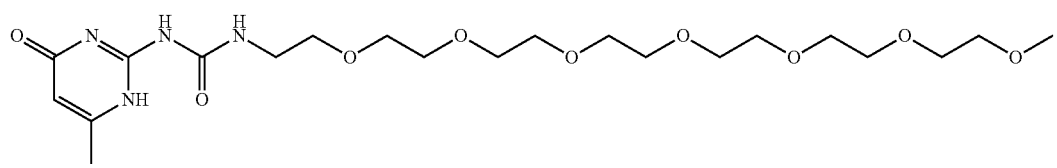 [SMILES: COCCOCCOCCOCCOCCOCCOCCNC(=O)Nc1nc(=O)cc(C)[nH]1]

A similar compound having a number of PEG units ranging from 5 to 20 may be used.

4/ Silicone Chains

The silicone chains are especially PDMS chains; they comprise at least one unit (Ia); the preferred PDMSs are described especially in WO 2004/052,963.

Mention may be made of phenyl silicones functionalized with ureidopyrimidone units, synthesized especially from aminopropylphenyl trimethicone, sold by Dow Corning, and onto which ureidopyrimidone units have been grafted via ureidopyrimidone functionalized with an isocyanate unit.

Use may be made, for example, of the compound of Example 11 described below.

5/ Fatty Substances, Especially "Supramolecular" Oils and Waxes

The supramolecular oils may be obtained by reaction between:
- on the one hand, at least one oil bearing at least one nucleophilic and/or electrophilic reactive function, and
- on the other hand, at least one junction group capable of establishing hydrogen bonds with one or more partner junction groups, each junction group pairing involving at least 3 hydrogen bonds, said junction group bearing at least one reactive function capable of reacting with the reactive function borne by the oil, said junction group comprising at least one unit of formula (I') or (II') as defined hereinbelow.

Preferably, the supramolecular oils may be obtained by reaction between:
- on the one hand, at least one oil bearing at least one nucleophilic reactive function chosen from OH and $NH_2$, and
- on the other hand, at least one junction group capable of establishing hydrogen bonds with one or more partner junction groups, each junction group pairing involving at least 3 hydrogen bonds, said junction group bearing at least one isocyanate or imidazole reactive function, said junction group comprising at least one unit of formula (I') or (II') as defined hereinbelow.

In conclusion, the supramolecular oils thus comprise at least one part (HB) originating from the oil and at least one part (G) originating from the junction group, said part (G) comprising at least one unit of formula (I') or (II').

In particular, said parts (HB) and (G) are connected via a covalent bond and may especially be connected via a covalent bond formed during the reaction between the OH and/or $NH_2$ reactive functions borne by the oil and the isocyanate functions borne by the junction group; or alternatively between the $NH_2$ reactive functions borne by the oil and the isocyanate or imidazole functions borne by the junction group.

The oil that may be used to prepare the supramolecular oils, which may preferably be represented schematically as $(HB)—(OH)_m(NH_2)_n$, is a fatty substance or a mixture of fatty substances, which is not crystalline at 25° C., and is liquid at room temperature and at atmospheric pressure (25° C., 1 atm.); preferably apolar or even, preferably, water-insoluble.

The term "liquid" means that the viscosity of the compound is less than or equal to 2500 centipoises, at 110° C. and 1 atm., measured with a Brookfield DV-I or Brookfield Cap 1000+ rheometer, a person skilled in the art selecting the machine that is suited to the viscosity measurement.

The term "apolar" refers to a compound whose HLB (hydrophilic-lipophilic balance) value is low; especially less than or equal to 8, preferably less than or equal to 4 and better still less than or equal to 2.

The term "insoluble" means that the fraction of oil which can dissolve in water, at 25° C., 1 atm., is less than 5% by weight (i.e. 5 g of oil in 100 ml of water); preferably less than 3%.

The term "fatty substance" means especially, but not exclusively, a hydrocarbon-based compound comprising one or more saturated or unsaturated, linear, cyclic or branched alkyl chains, containing at least 6 carbon atoms and possibly comprising polar groups such as an acid, hydroxyl or polyol, amine, amide, phosphoric acid, phosphate, ester, ether, urea, carbamate, thiol, thioether or thioester group, this chain possibly comprising up to 100 carbon atoms.

Preferably, the oil that may be used to prepare the supramolecular oil according to the invention is a non-volatile oil. The term "non-volatile oil" means an oil that is capable of remaining on keratin materials at room temperature and atmospheric pressure for at least several hours, and that especially has a vapor pressure of less than $10^{-3}$ mmHg (0.13 Pa).

Preferably, the oil has a molar mass (Mw) of between 150 and 6000, especially between 170 and 4000, or even between 180 and 2000, preferentially between 200 and 1500 and better still between 220 and 800 g/mol.

The oil that may be used in the context of the present invention bears at least one reactive function capable of reacting with the reactive function borne on the junction group, especially capable of reacting chemically with the isocyanate or imidazole groups borne by the junction group; preferably, this function is an OH or $NH_2$ function. Preferably, the oil comprises only OH functions, in particular 1 to 30H functions, preferentially primary or secondary OH functions, and better still only primary functions.

The oil that may be used in the context of the present invention may be chosen from:

(i) saturated or unsaturated, linear, branched or cyclic fatty alcohols comprising 6 to 50 carbon atoms, comprising 1 or more OH; optionally comprising one or more $NH_2$.

Mention may be made in particular of:
- saturated or unsaturated, linear or branched C6-C50, especially C6-C32 and in particular C8-C28 monoalcohols, and especially isostearyl alcohol, cetyl alcohol, oleyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol 1-12, Jarcol 1-16, Jarcol 1-20 and Jarcol 1-24;
- saturated or unsaturated, linear or branched C6-C50, especially C6-C40 and in particular C8-C38 diols, and especially branched C32-C36 diols, and in particular the commercial product Pripol 2033 from Uniqema;
- saturated or unsaturated, linear or branched C6-C50, especially C6-C32 and in particular C8-C28 triols, and especially phytanetriol;

(ii) esters and ethers bearing at least one free OH group, and especially partial polyol esters and ethers, and hydroxylated carboxylic acid esters.

The term "partial polyol ester" means esters prepared by esterification of a polyol with a substituted or unsubstituted carboxylic acid, the reaction not being total, i.e. not performed on all of the free OHs of the polyol; as a result, the ester thus still comprises at least one free OH.

Preferably, the carboxylic acid is a monoacid. A mixture of carboxylic acids, especially monocarboxylic acids, may also be used.

The term "partial polyol ether" means ethers prepared by etherification of a polyol, with itself or with at least one other monohydroxylated or polyhydroxylated alcohol, preferably a monoalcohol, the etherification reaction not being total, i.e. not performed on all of the free OHs of the polyol; as a result, the ether still comprises at least one free OH.

The term "hydroxylated carboxylic acid ester" means (mono and poly)esters prepared by reaction between a carboxylic acid bearing at least one OH function, and one or more (mono or poly)alcohols, preferably a monoalcohol, the reaction possibly being total or partial (performed on all or some of the free OHs of the alcohol). Among the polyols that may be used for preparing the above esters or ethers, mention may be made of propylene glycol, glycerol, neopentyl glycol, trimethylolpropane, trimethylolethane, polyglycerols and especially polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol or glucosamine; and also diol dimers obtained especially from fatty acid dimers, especially branched aliphatic and/or alicyclic C32-C38 and especially C36 diols, such as those defined in the article Hofer et al., European Coating Journal (March 2000), pages 26-37; and mixtures thereof.

Among the monoalcohols that may be used for preparing the above esters or ethers, mention may be made of linear or branched, preferably branched, C3-C50 alcohols, and especially 2-ethylhexanol, octanol and isostearyl alcohol, and mixtures thereof.

Among the carboxylic acids that may be used for preparing the above esters or ethers, mention may be made of linear or branched, saturated or unsaturated monoacids containing 6 to 50 carbon atoms and diacids containing 3 to 12 carbon atoms, among which mention may be made of octyldodecanoic acid, hexyldecanoic acid, ethylhexanoic acid, isostearic acid, nonanoic acid, isononanoic acid, arachidic acid, stearic acid, palmitic acid, oleic acid, oxalic acid, adipic acid, succinic acid, fumaric acid, maleic acid, capric acid, hexanedioic acid and decanoic acid, and mixtures thereof.

Among the hydroxylated carboxylic acids that may be used for preparing the above esters or ethers, mention may be made of monohydroxylated or polyhydroxylated acids, preferably monohydroxylated acids, containing for example 4 to 28 carbon atoms, and especially 12-hydroxystearic acid, ricinoleic acid, malic acid, lactic acid and citric acid; and mixtures thereof.

Thus, the oil that may be used in the present invention may be chosen, alone or as a mixture, from:

pentaerythritol partial esters, and especially pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl tetrakis(2-decyl)tetradecanoate, pentaerythrityl tetrakis(ethyl) hexanoate and pentaerythrityl tetrakis(octyl)dodecanoate;

dipentaerythritol diesters, triesters, tetraesters or pentaesters, and especially dipentaerythrityl pentaisononanoate, dipentaerythrityl pentaisostearate, dipentaerythrityl tetraisostearate and dipentaerythrityl tris(polyhydroxystearate);

trimethylolpropane monoesters and diesters, for instance trimethylolpropane monoisostearate, trimethylolpropane diisostearate, trimethylolpropane mono-2-ethylhexanoate and trimethylolpropane bis(2-ethylhexanoate);

bis(trimethylolpropane)monoesters, diesters and triesters, for instance bis(trimethylolpropane)diisostearate, bis(trimethylolpropane)triisostearate and bis(trimethylolpropane)triethylhexanoate;

partial monoesters or polyesters of glycerol or of polyglycerols, and especially:

glyceryl diisostearate and glyceryl diisononanoate;

polyglycerol-2 monoesters, diesters and triesters; for example with isostearic acid, 2-ethylhexanoic acid and/or isononanoic acid; and especially polyglyceryl-2 isostearate; polyglyceryl-2 diisostearate; polyglyceryl-2 triisostearate; polyglyceryl-2 nonaisostearate; polyglyceryl-2 nonanoate;

polyglycerol-3 monoesters, diesters, triesters or tetraesters; for example with either isostearic acid, 2-ethylhexanoic acid and/or isononanoic acid; and especially polyglyceryl-3 isostearate; polyglyceryl-3 diisostearate; polyglyceryl-3 triisostearate; polyglyceryl-3 nonaisostearate; polyglyceryl-3 nonanoate;

polyglycerol-10 partial esters and in particular polyglyceryl-10 nonaisostearate;

polyglyceryl-10 nonanoate; polyglyceryl-10 isostearate; polyglyceryl-10 diisostearate; polyglyceryl-10 triisostearate;

propylene glycol monoesters, for instance propylene glycol monoisostearate, propylene glycol neopentanoate or propylene glycol monooctanoate;

diol dimer monoesters, for instance isostearyl dimer dilinoleate and octyldodecyl dimer dilinoleate;

glycerol ethers, such as polyglyceryl-2 oleyl ether, polyglyceryl-3 cetyl ether, polyglyceryl-3 decyl tetradecyl ether and polyglyceryl-2 stearyl ether;

esters between a hydroxylated monocarboxylic, dicarboxylic or tricarboxylic acid and monoalcohols, and in particular:

esters, especially monoesters, of 12-hydroxystearic acid; such as octyl hydroxystearate and 2-octyldodecyl hydroxystearate; mention may also be made of the corresponding oligomeric polyhydroxystearates, especially having a degree of polymerization of from 1 to 10, bearing at least one residual OH;

lactic acid esters, and especially C4-40 alkyl lactates, such as 2-ethylhexyl lactate, diisostearyl lactate, isostearyl lactate, isononyl lactate or 2-octyldodecyl lactate;

malic acid esters, and especially C4-40 alkyl malates, such as bis(2-ethyl)hexyl malate, diisostearyl malate and bis(2-octyl)dodecyl malate;

citric acid esters, and especially C4-40 alkyl citrates, such as triisostearyl citrate, triisocetyl citrate and triisoarachidyl citrate;

(iii) hydroxylated natural oils, modified natural oils and plant oils, and especially:

triglyceryl esters bearing one or more OHs;

hydrogenated or non-hydrogenated castor oil, and also derivatives thereof derived especially from the transesterification of castor oil; for instance the products Polycin M-365 or Polycin 2525 sold by Vertellus;

modified epoxidized oils, the modification consisting in opening the epoxy function to obtain a diol, and especially hydroxylated modified soybean oil; hydroxylated soybean oils (directly hydroxylated or epoxidized beforehand); and especially the oils Agrol 2.0, Agrol 3.0 and Agrol 7.0 sold by Bio-Based Technologies, LLC; the oil Soyol R2-052 from the company Urethane Soy System; the Renuva oils sold by Dow Chemical; the oils BioH Polyol 210 and 500 sold by Cargill.

In particular, use may be made of the following glossy oils, for which the refractive index at 25° C. is indicated in parentheses: polyglyceryl-3 diisostearate (1.472), phytanetriol (1.467), castor oil (1.475), 2-octyldodecanol (1.46), oleyl alcohol (1.461), octyl hydroxystearate (1.46), polyglyceryl-2 isostearate (1.468), polyglyceryl-2 diisostearate (1.464), diisostearyl malate (1.462), 2-butyloctanol, 2-hexyldecanol (1.45), 2-decyltetradecanol (1.457), and also mixtures thereof.

Preferably, the oils that may be used in the present invention are chosen from 2-octyldodecanol, diisostearyl malate, 2-butyloctanol, 2-hexyldecanol, 2-decyltetradecanol; hydrogenated or non-hydrogenated castor oil, and also derivatives thereof; hydroxylated modified soybean oil, and mixtures thereof.

The junction group that may be used to form the supramolecular oil according to the invention bears at least one reactive group, especially isocyanate or imidazole, capable of reacting with the reactive functions, especially OH and/or $NH_2$ (exclusively $NH_2$ for imidazole), of the oil, in order to form a covalent bond, especially of urethane type, between said oil and said junction group.

Said junction group is capable of establishing H bonds with one or more partner junction groups, of identical or different chemical nature, each junction group pairing involving at least 3H (hydrogen) bonds, preferably at least 4H bonds and preferentially 4H bonds.

Said junction group, bearing isocyanate groups, may thus be represented schematically as $(G)(NCO)_p$, p being a non-zero integer, preferably equal to 1 or 2. The junction group moreover comprises at least one monovalent unit of formula (I') and/or at least one divalent unit of formula (II'), as defined below:

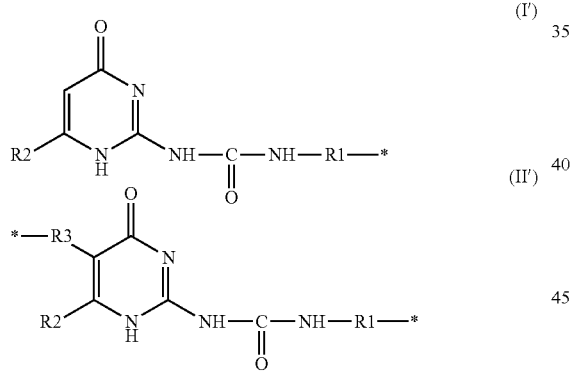

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a methyl radical.

In a particularly preferred manner, the following may apply in formula (I'):
R1=-isophorone-, R2=methyl, which gives the unit of formula:

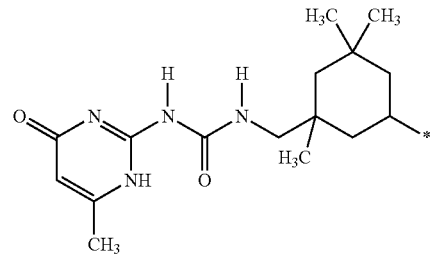

R1=—(CH$_2$)$_6$—, R2=methyl, which gives the unit of formula:

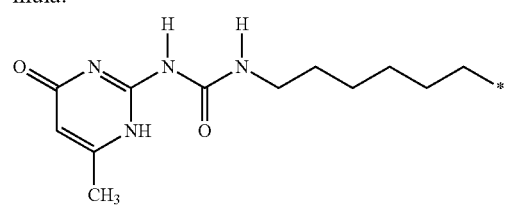

R1=—(CH$_2$)$_6$—, R2=isopropyl, which gives the unit of formula:

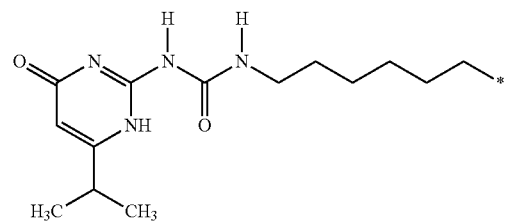

R1=4,4'-methylenebiscyclohexylene and R2=methyl, which gives the unit of formula:

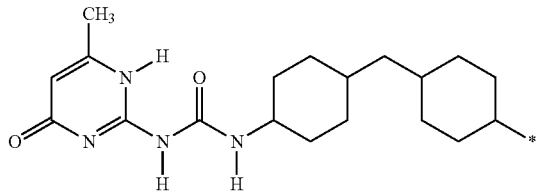

In a particularly preferred manner, in formula (II'), R1 represents the -isophorone-radical, R2=methyl and R3=—(CH$_2$)$_2$OCO—NH-isophorone-, which gives the divalent unit of formula:

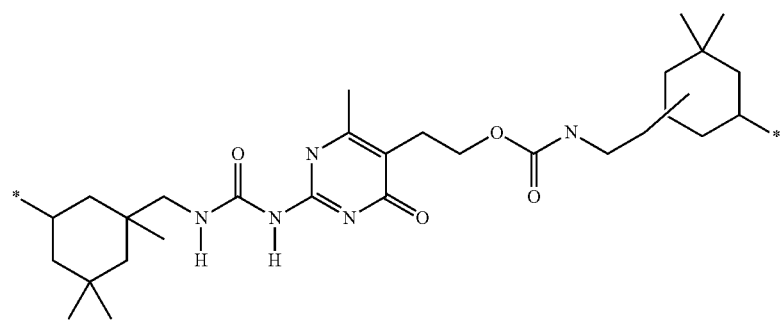

The junction groups bearing only one isocyanate function may have the formula:

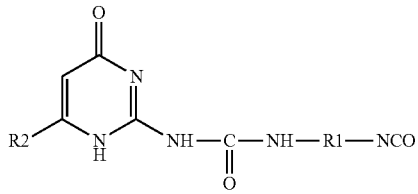

in which R1 and R2 are as defined above; and in particular:
R1 represents -isophorone-, —(CH$_2$)$_6$—, CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents CH$_3$.

Preferably, the junction groups may be chosen from the following groups:

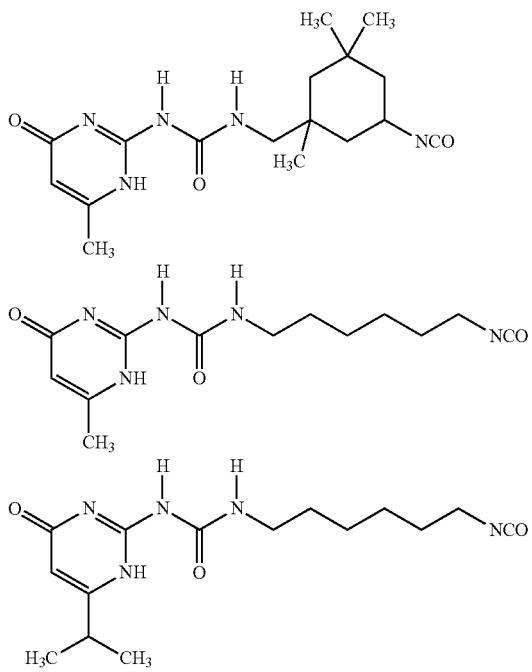

-continued

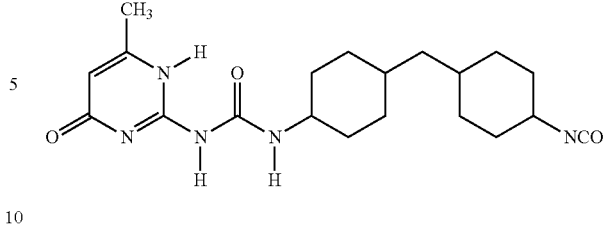

The junction groups bearing two isocyanate functions may have the formula:

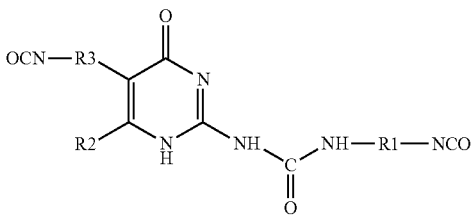

in which R1, R2 and R3 are as defined above, and in particular:
R1 represents -isophorone-, —(CH$_2$)$_2$—, —(CH$_2$)$_6$—, CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or R2 represents CH$_3$, and/or R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or mixtures thereof; and in particular R'3 represents a C1-C4 alkylene, in particular 1,2-ethylene, and R'4 represents the divalent radical derived from isophorone.

A junction group that is most particularly preferred is the one having the formula:

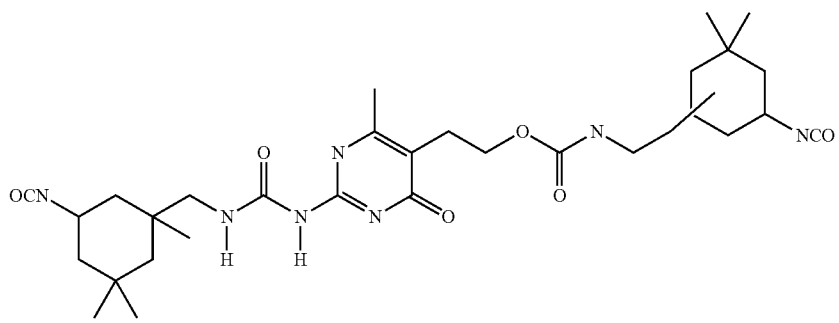

Among the junction groups bearing an imidazole group, mention may be made of the following compound:

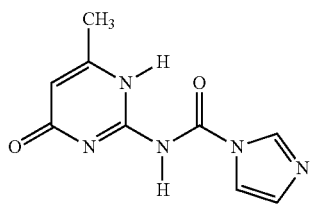 [SMILES: Cc1cc(=O)nc(NC(=O)n2ccnc2)[nH]1]

According to one particular embodiment of the invention, the junction groups may be attached to the oil by functionalization of the junction group with an isocyanate or imidazole.

According to another embodiment, it is possible to perform the reverse reaction by prefunctionalizing the oil with a diisocyanate.

The supramolecular oils according to the invention may especially correspond to the following structures:

ureidopyrimidone-functionalized octyldodecanol of structure:

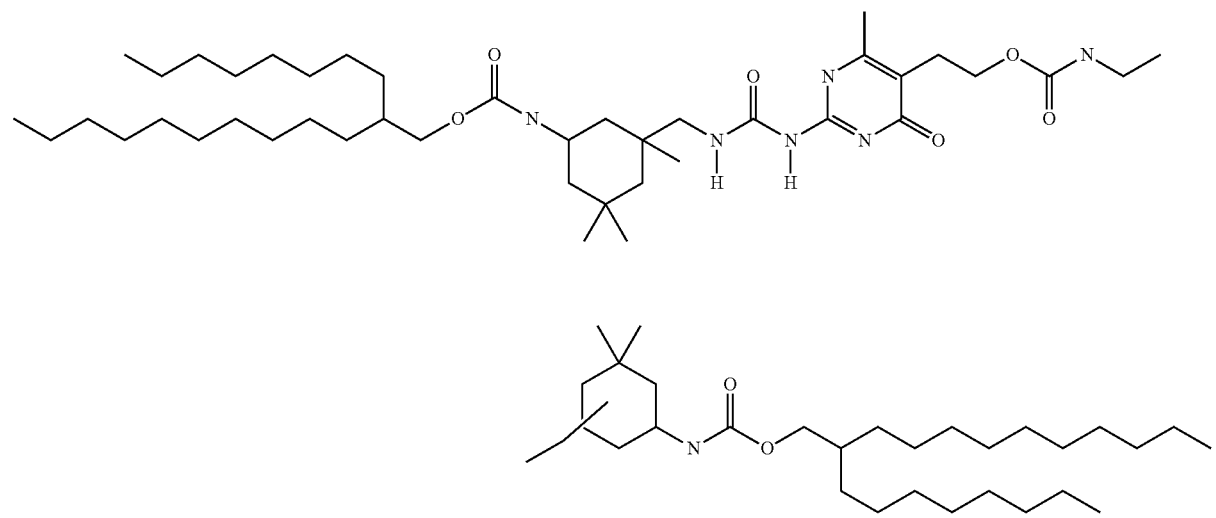

or of structure:

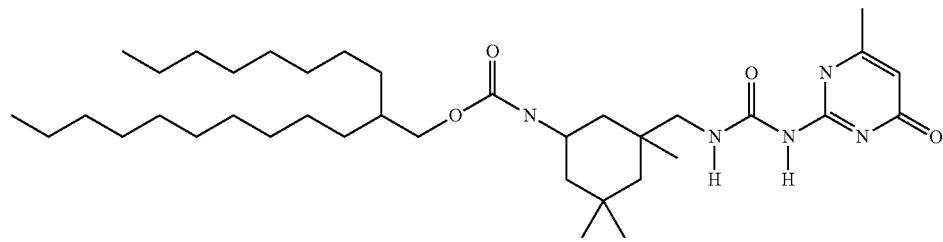 [SMILES: CCCCCCCCCCC(CCCCCCCC)COC(=O)NC1CC(C)(C)CC(C)(CNC(=O)Nc2nc(=O)cc(C)[nH]2)C1]

ureidopyrimidone-functionalized diisostearyl malate of structure:

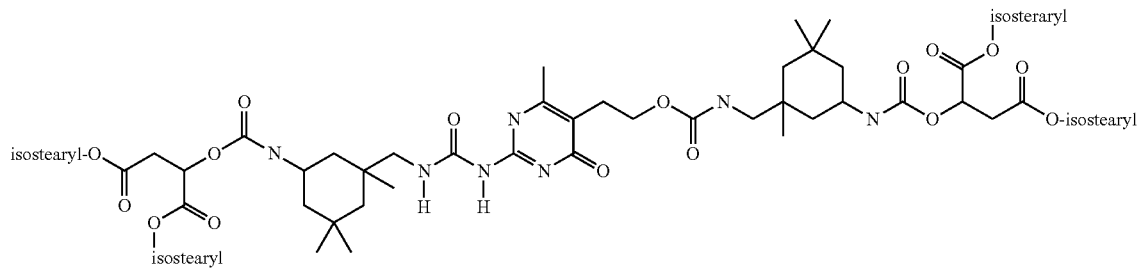

or of structure:

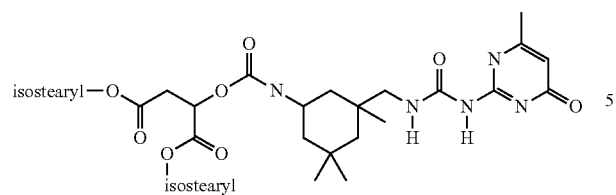
ureidopyrimidone-functionalized castor oil of structure:
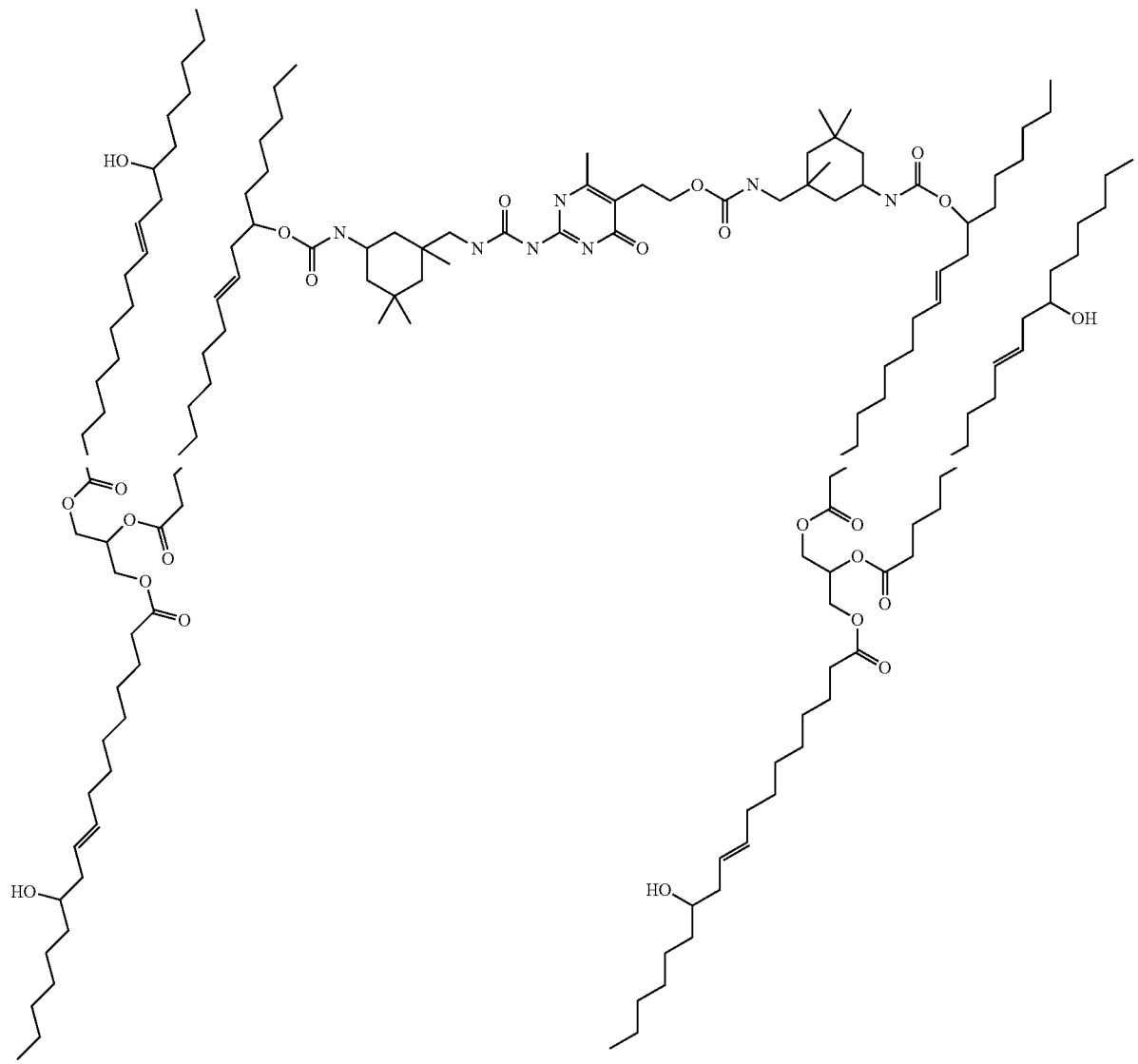
or of structure:

51
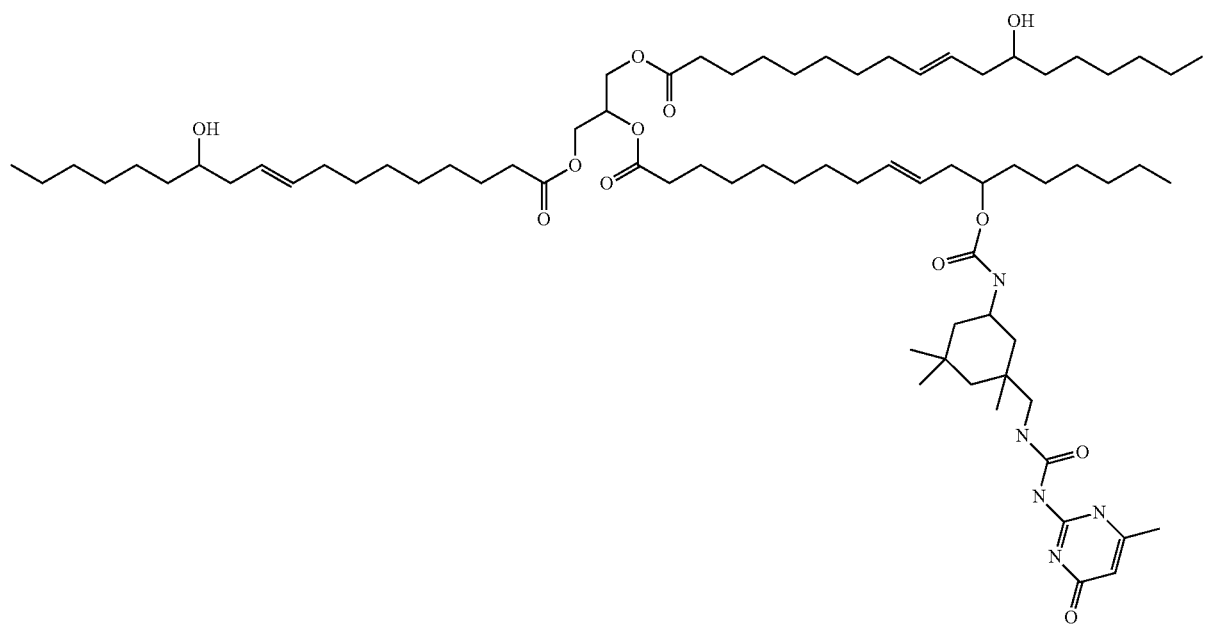 [SMILES: CCCCCCC(O)C/C=C/CCCCCCCC(=O)OCC(COC(=O)CCCCCCC/C=C/CC(O)CCCCCC)OC(=O)CCCCCCC/C=C/CC(CCCCCC)OC(=O)NC1CC(C)(C)CC(C)(CNC(=O)Nc2nc(=O)cc(C)[nH]2)C1]
52
ureidopyrimidone-functionalized 2-hexyldecanol of structure:
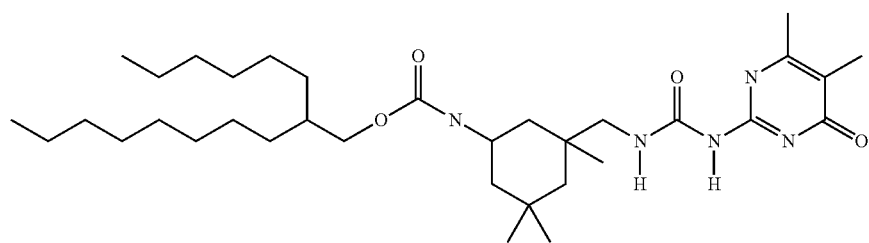
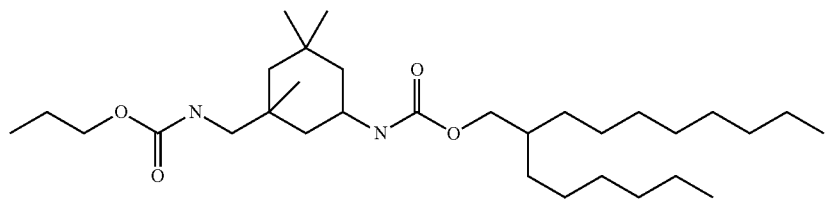
or of structure:
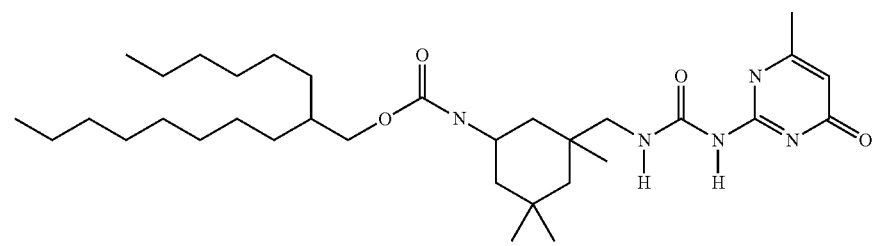 [SMILES: CCCCCCCCC(CCCCCC)COC(=O)NC1CC(C)(C)CC(C)(CNC(=O)Nc2nc(=O)cc(C)[nH]2)C1]
ureidopyrimidone-functionalized 2-decyltetradecanol of structure:

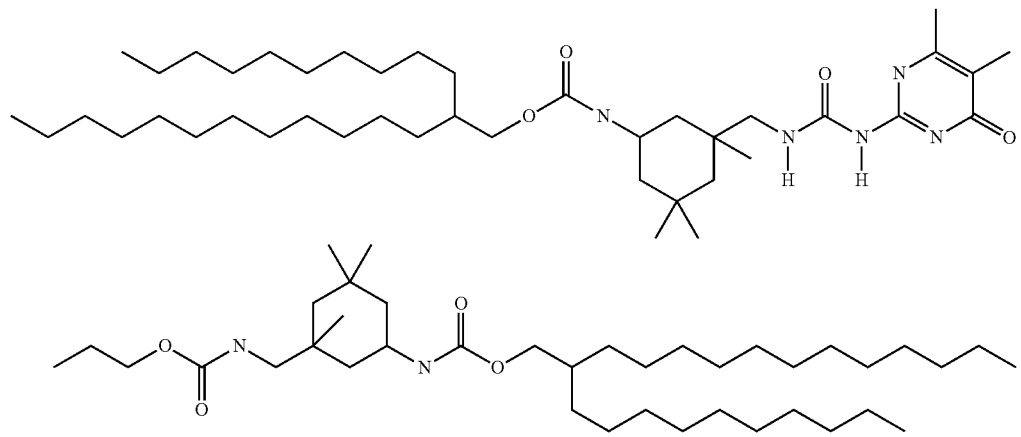

or of structure:

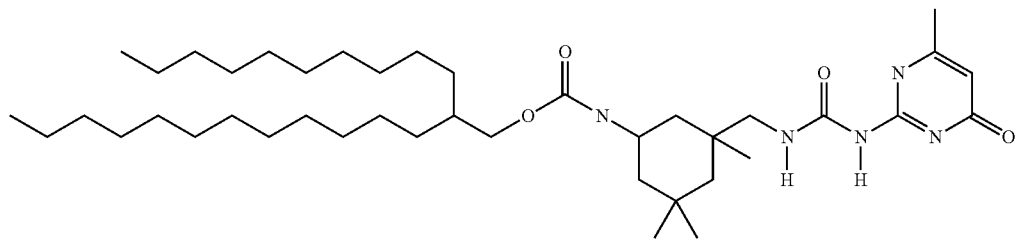 [SMILES: CCCCCCCCCCCCC(CCCCCCCCCC)COC(=O)NC1CC(C)(C)CC(C)(CNC(=O)Nc2nc(=O)cc(C)[nH]2)C1]

The ureidopyrimidone-functionalized castor oil described previously is preferably used.

Similarly, the supramolecular waxes may be obtained by reaction between:
- at least one wax bearing at least one reactive function chosen from OH and COOH, or even anhydride, and
- at least one junction group capable of establishing hydrogen bonds with one or more partner junction groups, each junction group pairing involving at least 4 hydrogen bonds, said junction group bearing at least one "complementary" reactive function capable of reacting with the reactive function borne by the wax, said junction group comprising at least one unit of formula (I') or (II') as defined above.

The wax that may be used for preparing the supramolecular wax according to the invention is a lipophilic fatty substance or a lipophilic fatty substance mixture, which is crystalline at 25° C., and solid at room temperature and under atmospheric pressure (25° C., 1 atm.), preferably with a reversible solid/liquid change of state and generally having a melting point above 40° C., better still above 55° C. and even better still above 75° C., and which can range up to 200° C., in particular up to 120° C. By bringing the wax to its melting point, it is possible to make it miscible with oils and to form a microscopically homogeneous mixture, but if the temperature of the mixture is brought back to room temperature, recrystallization of the wax from the oils of the mixture is obtained.

The wax that may be used in the context of the present invention therefore bears at least one reactive function capable of reacting with the complementary reactive function borne by the junction group, and in particular capable of reacting chemically with the isocyanate groups borne by the junction group; preferably, this function is an OH or COOH function, or even an anhydride function. Preferably, the wax bears only OH functions, preferentially primary or secondary OH functions, and even better still only primary OH functions.

The waxes that may be used in the context of the present invention may be of plant, mineral, animal or synthetic origin.

They may be chosen from the following waxes, alone or as a mixture, it being understood that these waxes bear a reactive function, in particular an OH, COOH, or even anhydride reactive function:

(i) long-chain, generally linear, alcohols of formula $CH_3—(CH_2)n\text{-}OH$ with n between 13 and 60, in particular between 15 and 47, or even between 15 and 31.

Such fatty alcohols are commercially available, for example from the company New Phase Technologies or the company Petrolite. They may be mixtures of long-chain linear alcohols that can be obtained by means of a polymerization process which makes it possible to obtain polymers with a very low polydispersity index (Mw/Mn less than 1.1). Their weight-average molar mass (Mw) is generally between 350 and 1000. Mention may in particular be made of cetyl alcohol, stearyl alcohol and octacosanol;

(ii) saturated or unsaturated, generally linear, C8-C60 long-chain acids; mention may in particular be made of those of formula $CH_3—(CH_2)n\text{-}COOH$ with n between 6 and 58, in particular between 8 and 48, or even between 10 and 32; mention may also be made of C6-C60, or even C8-C32, monounsaturated or polyunsaturated fatty acids;

(iii) calcium lanolates or stearates;

(iv) lanolin and derivatives thereof, such as hydrogenated, hydroxylated or acetylated lanolin, lanolin alcohols, lanolin fatty acids and acetylated lanolin alcohol;

(v) polyolefin waxes, in particular poly(alpha-olefin) homopolymers and copolymers, preferably having a melting point above 25° C., preferably between 25 and 110° C., which are optionally polyoxyalkylenated (C2-C3 alkyl), optionally (poly)glycerolated, and which bear at least one functional group —OH, —COOH or carboxylic acid anhydride, for example -(polyoxyalkylene)n-OH, or polyglyerol. Among these polyolefins, mention may be made of homopolymers and copolymers of C2-C30, preferably C2-C10, or even C2-C3, olefins. Polyethylene and polypropylene homopolymers, and their copolymers with each other or with another C4-C10 α-olefin, are in particular preferred. These polyolefins, preferably oligomers of Mw less than 10 000, can be obtained by means of the known polymerization techniques: radical polymerization, Ziegler-Natta polymerization, or using metallocene initiators.

Mention may be made in particular of:
polyethylene or polypropylene waxes, ending with an OH end group, such as the Performacol products sold by New Phase Technologies, in particular Performacol 350 (Mp 79° C.), 425 (Mp 91° C.) and 550 (Mp 99° C.);
polyoxyethylenated and/or polyoxypropylenated polyethylene or polypropylene waxes ending with a —(POE)—OH, —(PPO)—OH or —(POE)/(PPO)—OH end group, such as the Performatox Ethoxylate ethoxylated polyethylenes sold by New Phase Technologies, in particular Performatox Ethoxylate 420 (Mp 91° C.), 450 (Mp 91° C.), 480 (Mp 80° C.), 490 (Mp 71° C.), 520 (Mp 99° C.) and 550 (Mp 99° C.);
polyolefins, preferably polyethylene or polypropylene, which are glycerolated ou polyglycerolated (bearing —[O—CH$_2$—CH(OH)—CH$_2$]$_x$—OH groups) with x preferably between 1 and 50;
polyolefins, preferably polyethylene or polypropylene, bearing a COOH or carboxylic acid anhydride group; in particular
polyethylenes or polypropylenes bearing a COOH end such as the Performacid Acid products sold by New Phase Technologies, in particular Performacid Acid 350 (Mp 89° C.), 425 (Mp 93° C.), 550 (Mp 101° C.) and 700 (Mp 110° C.);
polyolefins, in particular ethylene and/or propylene homopolymers or copolymers, bearing one or more succinic anhydride groups along their chain and resulting from the addition of maleic anhydride on one or more residual unsaturations, or from direct olefin-maleic anhydride copolymerization, such as: (i) polypropylenes comprising maleic anhydride groups (or succinic anhydride groups once attached to the chain), in particular Licocare PP207 from Clariant, (ii) polyethylenes comprising maleic anhydride groups, in particular Ethylene-Maleic Anhydride Copolymer from Honeywell, such as A-C 573 A (Drop point: 106° C.), A-C 596 A (Drop point: 143° C.); (iii) poly(isobutylene-maleic anhydride) copolymers, in particular those sold by Kuraray under the trade name Isobam; (iv) maleic anhydride/octadecene copolymers such as those sold by Chevron Phillips Company under the name PA18; (v) copolymers between long-chain olefins and maleic anhydride, such as Licocare CM 401 LP 3345 from Clariant;
(vi) natural waxes which have a large fraction of free fatty alcohols and/or of free fatty acids; among those comprising free fatty alcohols, mention may be made of candelilla wax, carnauba wax and sugarcane wax; among those comprising free fatty acids, mention may be made of beeswax, orange wax, montan wax, lemon wax and sugarcane wax;
(vii) polyoxyethylenated (bearing an end OH) or polyglycerolated (several side OH and an end OH) "natural" waxes; these are natural or synthetic waxes which may have one or more residual COOH which are reacted with an alcohol, dialcohol, polyol or ethoxylated alcohol, or a C2-C4 alkylene glycol (preferably glycerol) or polyglycerol; mention may in particular be made of:
polyoxyethylenated natural waxes (number of EO preferably between 2 and 100): PEG Beewax (Apifil from Gattefosse or PEG-8 Bee Wax from Koster Keunen), PEG Candelilla Wax; PEG Carnauba Wax such as PEG-12 Carnauba from Koster Keunen; PEG Lanolin; oxypropylenated lanolin wax; PEG Spermaceti Wax; PEG Shellac Wax;
glycerolated or polyglycerolated waxes: polyglycerolated beeswax, in particular polyglyceryl-3 Beewax (Cera Bellina Wax from Koster Keunen); the *Acacia* Decurrens/Jojoba/Sunflower Seed Wax/Polyglyceryl-3 Esters mixture (Hydracire S from Gattefosse);
(viii) silicone waxes, for instance polyether silicone waxes, and alkyl or alkoxy dimethicones having from 16 to 45 carbon atoms;
(ix) polyoxyalkylenated C12-C40 fatty alcohols, in particular bearing at least one C12-C40, in particular C14-C32, alkyl group, and a polyoxylkylene, preferably polyoxyethylene and/or polyoxypropylene, group, with an OH end; in particular polyoxyethylenated stearyl alcohol, and more particularly Steareth-10 or polyoxyethylenated (10 EO) stearyl alcohol, Steareth-2 or polyoxyethylenated (2 EO) stearyl alcohol and Steareth-20 or polyoxyethylenated (20 EO) stearyl alcohol, and in particular Brij S10-SO, Brij S2-SO and Brij S20-SO from Croda; mixtures of oxyethylenated lanolin fatty alcohols, such as Solulan 16 Lanolin from Lubrizol; Tegocare 150 from Evonik, Emulcire 61 WL2659 from Gattefosse; lsosteareth-20 or polyoxyethylenated (20 EO) isostearyl alcohol, such as Arosurf 66E20 from Witco; PEG-6 Decyltetradeceth-30, in particular Nikkopol PEN-4630 from Nikko; PEG-6 Decyltetradeceth-12, in particular Nikkol PEN-4612 from Nikko; PEG-4 Montanate, in particular Licowax KST from Clariant; hydrogenated and polyoxyethylenated caster oils, such as PEG-7 Hydrogenated Castor Oil and in particular Cremophor PH from BASF; the PEG-45/dodecylglycol copolymer and in particular Elfacos ST9 from Akzo;
(x) monoesters or multiesters between at least one polyol, including glycerol, and a C8-C40 mono fatty acid, bearing at least one free OH; and monoesters or multi-ethers between a polyol and a C8-C40 mono fatty alcohol. Mention may in particular be made, as fatty acid, of: stearic acid, behenic acid; as polyol bearing at least one residual OH: pentaerythritol, erythritol, dipentaerythritol, trimethylolpropane, di-trimethylolpropane, glycerol, diglyerol, polyglycerols and sucrose. Mention may in particular be made of batyl alcohol or glycerol monostearyl ether, and in particular Batylalcool 100 from Nikko; bis-diglyceryl polyacyladipate-2 (=isostearic, adipic acid and glyceryl plant fatty acid esters) such as Softisan 649 from Sasol; glycol montanate or octacosanoate, such as Licowax KPS Flakes from Clariant; pentaerythrityl distearate such as Cutina PES from Cognis; esters of sucrose and of a fatty acid with a residual OH, and in particular sucrose esterified with 6-8 behenic acid chains, comprising at least 2 free OH, such as Cromaderm B from Croda; pentaerythrityl isostearate/caprate/caprylate/adipate with residual OHs, such as Supermol L-LQ(RB) from Croda, sucrose palmitate such as Surfhope SE COSME C-1615 from Mitsubishi; sucrose tribehenate such as Surfhope SE COSME C-2203 from Mitsubishi.

Mention may also be made, by way of preference, of monoesters or polyesters between at least one glycerol, monoglycerolated or polyglycerolated, and a C8-C40, in particular C12-C32, mono fatty acid, bearing at least one free OH; mention may in particular be made of polyglyceryl-10 behenate/eicosadioate such as Nomcort HK-P from Nisshin Oil; glyceryl behenate/eicosadioate such as Nomcort HK-G from Nisshin Oil; polyglyceryl-10 hydroxystearate/stearate/eicosadioate such as Nikkol Nikkowax LM from Nikko Chemicals; polyglyceryl-10 pentastearate (5 free OH) such as Sunsoft Q-185S from Taiyo Kagaku; glyceryl stearate such as Sunsoft 8000V from Taiyo Kagaku; glyceryl laurate such as Sunsoft 750 from Taiyo Kagaku; glyceryl behenate (mono-+ dibehenate) such as Dub BG from Stearinerie Dubois;

(xi) monoesters or polyesters between at least one C8-C40 polycarboxylic acid and one C8-C40 monoalcohol;

(xii) esters of a C8-C40 fatty acid and of a C8-C40 fatty alcohol, bearing in addition at least one OH group; and in particular:

esters of 12-hydroxystearic acid, with a C8-C40 monoalcohol, diol or polyol; in particular trihydroxystearin or glyceryl trihydroxystearate, such as Thixin R from Elementis; ethylhexyl hydroxystearate such as Wickenol 171 from Alzo; dipentaerythrityl hexahydroxystearate, such as Salacos 168M from Nisshin Oil; hydroxystearoyl stearate of C18-C38 fatty alcohols such as Kesterwax K82P from Koster Keunen; hydroxyoctacosanyl hydroxystearate such as Elfacos C26 from Akzo (which in the end bears 2 free OH)

esters of hydrogenated ricinoleic acid with a C8-C40 monoalcohol, diol or polyol; in particular cetyl esters of hydrogenated castor oil fatty acids, such as Phytowax Ricin 16L 64 from Sophim;

esters or polyesters between hydrogenated castor oil (30H) and $C_8$-$C_{40}$ monoacid or diacid, retaining at least one of the three OH of the hydrogenated castor oil molecule, and in particular the polycondensate between hydrogenated castor oil and isostearic and adipic acids, such as Haimalate 618 from Kokyu Alcohol;

esters of citric acid and of C8-C40 fatty alcohols, comprising at least one OH of the acid that is free; in particular tri(C14-C15)alkyl citrate, such as Cosmacol ECL from Sassol.

A mixture of waxes may obviously be used.

Preferably, the waxes that can be used in the present invention are chosen from cetyl alcohol, beeswax, carnauba wax and jojoba wax, and mixtures thereof.

6/ UV-Screening Agents

The active agents may also be UV-screening agents and may correspond to either of the formulae (Ib) and (IIb) below:

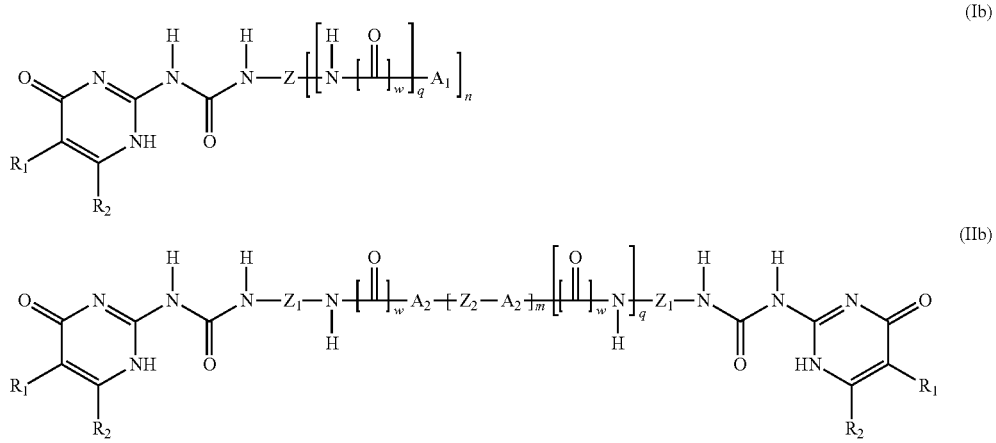

in which:

n=1, 2 or 3; preferably n=1;

m=0 or 1;

w=0 or 1; the value of w is conditioned by the nature of the groups $A_1$ and $A_2$ as specifically mentioned in the definition of said groups;

with the condition that when w=0, then the radical $A_1$ and the diradical $A_2$ cannot end with a nitrogen;

q=0 or 1; the value of q is conditioned by the nature of the groups $A_1$ and $A_2$ as specifically mentioned in the definition of said groups;

$R_1$=H and $R_2$=methyl;

Z represents a multivalent radical (divalent to tetravalent, depending on the value of n) chosen from:

(i) a linear or branched, saturated or unsaturated $C_1$-$C_{32}$ carbon-based and especially hydrocarbon-based radical; optionally interrupted or substituted, one or more times, with an optionally aromatic $C_3$-$C_{12}$ (hetero)cycle; or (ii) an optionally aromatic $C_3$-$C_{12}$ carbon-based and especially hydrocarbon-based (hetero)cyclic radical; optionally substituted with one or more linear or branched, saturated or unsaturated $C_1$-$C_{32}$ carbon-based and especially hydrocarbon-based radicals;

(iii) a radical —($C_5$-$C_6$)cycloalkyl($C_1$-$C_{12}$)alkyl-said radical Z possibly being:

(1) substituted with 1 to 12 identical or different groups chosen from —OH, —SO₃R, —OSO₃R, —SO₃H, —OSO₃H, —COOH, —COOR, —CONRR', $C_1$-$C_4$ alkyl and —N⁺RR'R", An⁻ and/or (2) interrupted or terminated with 1 to 5 identical or different groups chosen from the divalent groups: —S—, —NH— (or =NH), —O—, —C(O)—, —SO₂—, or combinations thereof, for instance —NHC(O)—, —C(O)NH—, —OC(O)—, —C(O)O—, or

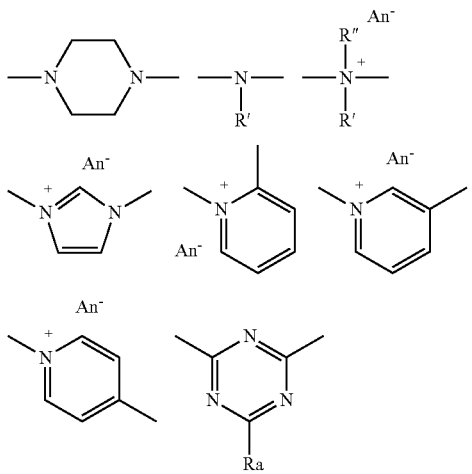

with $R_a$=H or halogen, especially Cl, or $C_1$-$C_6$ alkyl; and R, R' and R", which may be identical or different, being H or a linear or branched $C_1$-$C_{12}$ alkyl radical; it being understood that said radical Z comprises at least one heteroatom chosen from N, O and S; when Z is interrupted or substituted with a cationic group, the electrical neutrality of the compounds of formula (Ib) is ensured by a cosmetically acceptable anion or mixture of anions An⁻;

- Z may also denote a covalent bond for the compounds of formula (Ib) when n=1 and q=0, $Z'_1$ not being able to denote a covalent bond;
- $Z_1$ and $Z'_1$, which may be identical or different, denote a divalent radical Z; not being able to denote a covalent bond;
- $Z_2$ is a linear or branched divalent $C_1$-$C_{32}$ alkyl radical;
- the monoradicals $A_1$ corresponding to one of the formulae (IIIa) to (XIIa) below:

a) Para-Aminobenzoate:

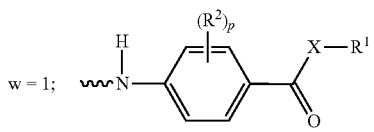
(IIIa)

b) Cinnamate, Benzalmalonate or Cyanoacrylate:

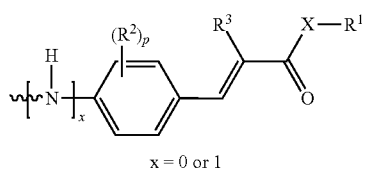
(IVa)

it being understood that
- q=w=x=1 when Z is not a covalent bond, and
- q=x=0 when Z is a covalent bond c) benzophenone:

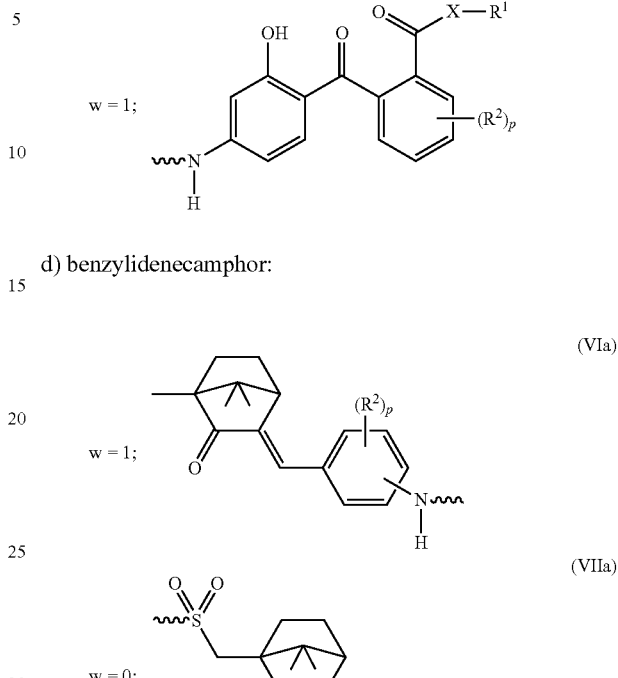
(Va)
(VIa)
(VIIa)
(VIIIa)

e) benzotriazole:

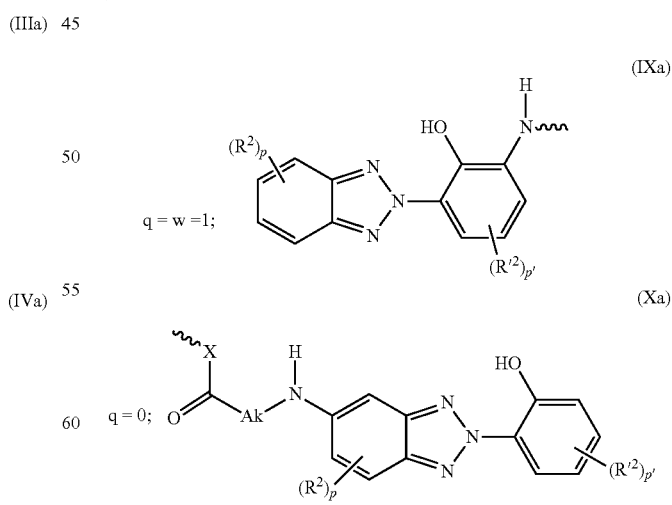
(IXa)
(Xa)

with X=O or NH
Ak=linear saturated divalent C1-C6, preferably C2, alkyl radical.

(XIa)

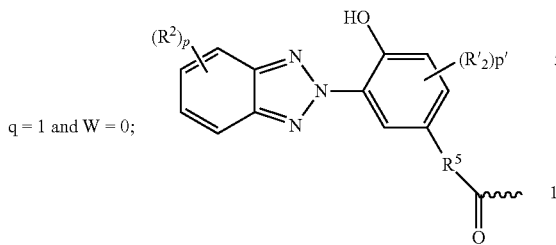

q = 1 and W = 0;

f) s-Triazine:

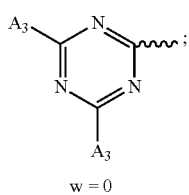

(XIIa)

w = 0 with the radicals $A_3$, which may be identical or different, representing the radicals $A_1$ of formula (IIIa), (IVa), (Va), (VIa) or (IXa);
the diradicals $A_2$ corresponding to one of the formulae (IIIb) to (VIIb) below:

a/ Para-Aminobenzoate:

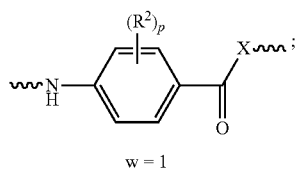

(IIIb)

w = 1 with X=O or NH b/ Cinnamate, Benzalmalonate or Cyanoacrylate:

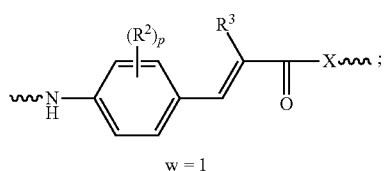

(IVb)

w = 1 with X=O or NH c/ Benzophenone:

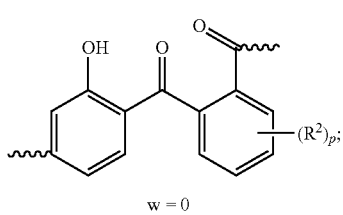

(Vb)

w = 0 d) Benzylidenecamphor:

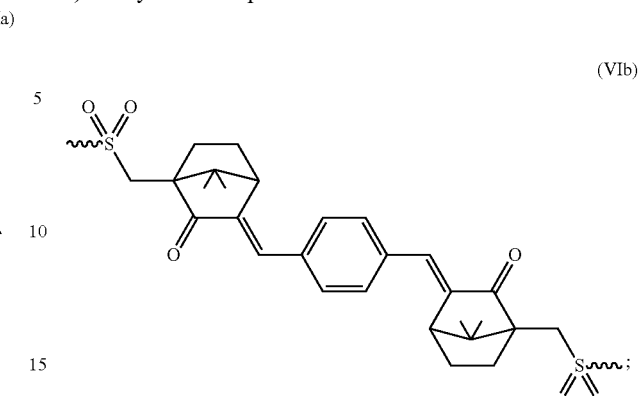

(VIb)

w = 0 e/ s-Triazine:

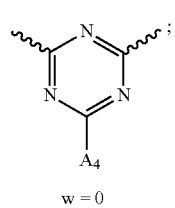

(VIIb)

w = 0 with $A_4$ representing a radical of formula (IIIa), (IVa), (Va), (VIa) or (IXa);
in which:
  $R^1$ represents a linear or branched $C_1$-$C_{30}$ alkyl or $C_3$-$C_{30}$ alkenyl radical, which may bear one or more hydroxyl substituents and which may contain in the carbon-based chain an alkyl ring, one or more heteroatoms chosen from oxygen, nitrogen and silicon atoms, an optionally substituted $C_6$-$C_{20}$ aryl radical;
  $R^2$ and $R'^2$ represent, independently, a linear or branched $C_1$-$C_{10}$ alkoxy radical, a linear or branched $C_1$-$C_{10}$ alkyl radical, a linear or branched $C_2$-$C_8$ alkenyl radical or —OSi(CH$_3$)$_3$, two adjacent radicals $R^2$ together possibly forming an alkylidenedioxy group in which the alkylidene group contains from 1 to 2 carbon atoms (i.e. a group —O—(CH$_2$)$_t$—O— with t=1 or 2),
  p and p' are, independently, 0, 1 or 2,
  $R^3$ is hydrogen, a $C_1$-$C_4$ alkyl radical, or a radical chosen from —(C=O)XR$^1$, —CN, —(C=O)R$^1$, —SO$_2$R$^4$ with $R^1$ having the same definition as above and
  $R^4$ represents a linear or branched $C_1$-$C_{12}$ alkyl radical or a $C_6$-$C_{20}$ aryl radical, which is optionally substituted,
  $R^5$ represents a divalent $C_2$-$C_8$ alkyl radical,
  X represents oxygen or a radical —NR$^6$ with $R^6$ being a linear or branched $C_1$-$C_8$ alkyl radical.

Preference will be given to the compounds of formula (Ib) or (IIb) in which:
  n=1; and/or
  m=0 or 1; and/or
  $R_1$=H or —Z'$_1$-A$_1$; and/or
  $R_2$ is a linear or branched $C_1$-$C_3$ alkyl radical; and/or
  the radical Z (or $Z_1$ and/or $Z'_1$) denotes a linear $C_1$-$C_{12}$ divalent alkyl radical, the divalent $C_3$-$C_8$ cycloalkyl radical optionally substituted with one or more identical or different linear or branched C1-C4 alkyl radicals or the following divalent radicals:

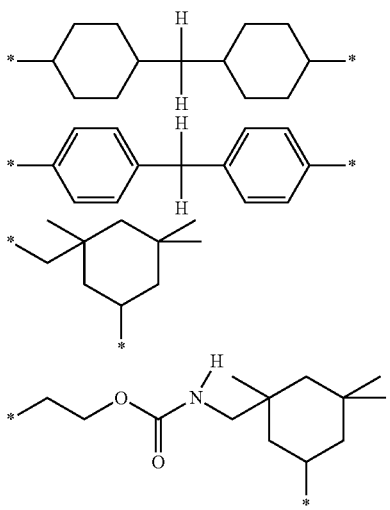

Z also possibly denoting a covalent bond when n=1 and q=0; and/or $Z_2$ denotes a linear divalent $C_2$-$C_{20}$ alkyl radical, and in the radicals $A_1$ and/or $A_2$, $R^1$ is a $C_1$-$C_8$ alkyl, optionally substituted with 1 or 2 hydroxyl groups, X is —O—, p=p'=0, $R^3$ is —CN or —COOR', $R^5$ is —CH$_2$CH$_2$—.

Even more preferably, the compounds correspond to formulae (Ib) and (IIb) in which:

n=1;
m=0 or 1;
$R_1$ is H or —Z'$_1$-A$_1$;
$R_2$ is the linear or branched $C_1$-$C_3$ alkyl radical;

the radical Z (or $Z_1$ and/or $Z'_1$) denotes a linear divalent $C_1$-$C_{12}$ alkyl radical, preferably a 1,2-ethylene; 1,6-hexylene; 1,4-butylene radical, or a divalent radical:

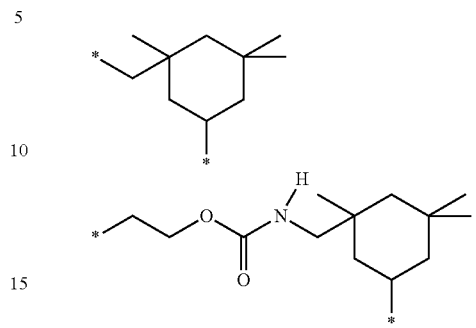

Z also possibly denoting a covalent bond when n=1 and q=0;

$Z_2$ denotes a linear divalent $C_2$-$C_{20}$ alkyl radical, in particular a tetradecyl radical;

$R^1$ is a $C_1$-$C_8$ alkyl, optionally substituted with 1 or 2 hydroxyl groups, X is —O—, p=p'=0, $R^3$ is —CN or —COOR$^1$, $R^5$ is —CH$_2$CH$_2$—.

Preferably, the mass-average molecular weight (Mw) of the compounds of formula (Ib) or (IIb) is less than 2000 g/mol.

The compound described in Example 5 below may be used as screening agent bearing a triazine group.

Particularly preferred compounds that may be mentioned include:

1/ Para-Aminobenzoate Derivatives:
those of formula (Ib) for which $A_1$ corresponds to formula (IIIa)

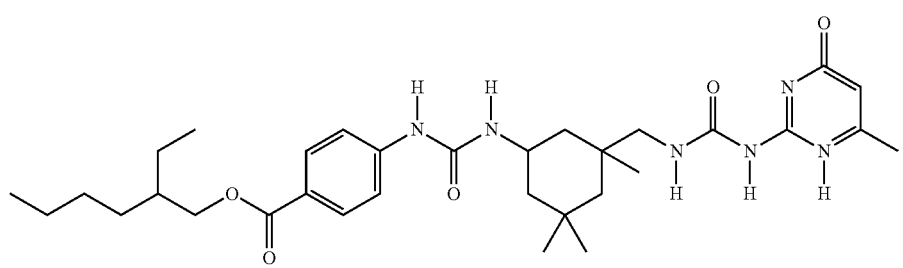

(1)

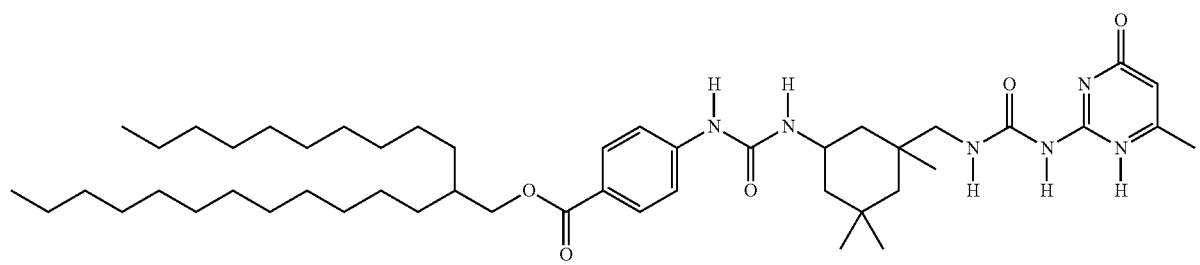

(2)

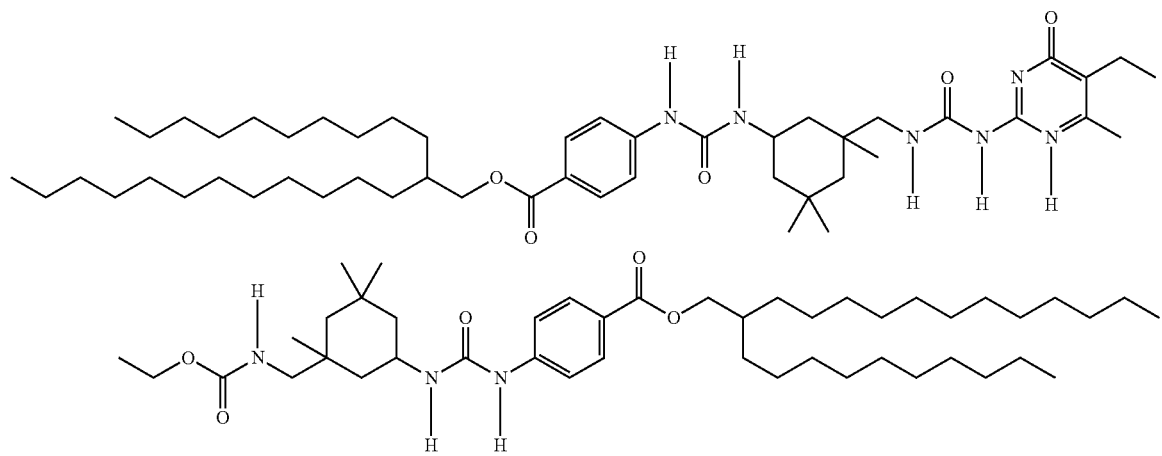
(3)
those of formula (IIb) for which $A_2$ corresponds to formula (IIIb)
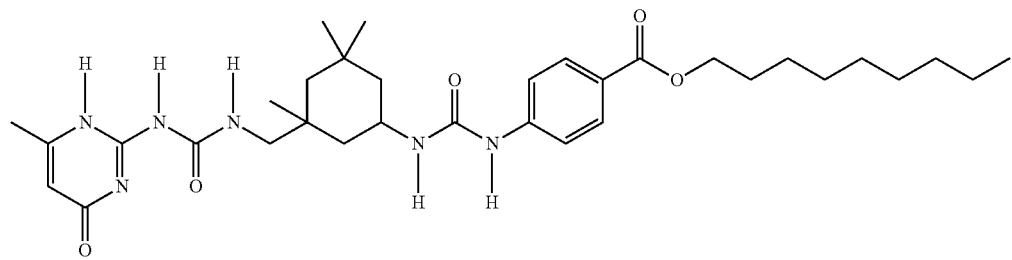
(4)
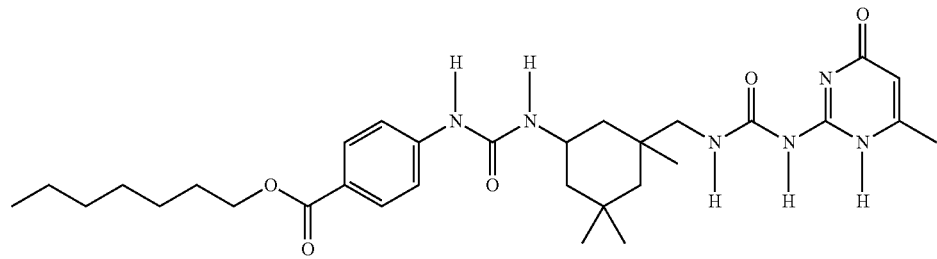
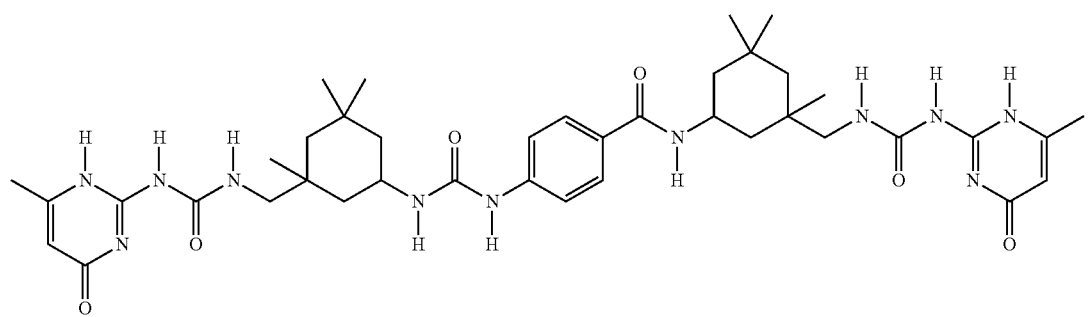
(5)

2/ Cinnamate Derivatives:
   those of formula (Ib) for which $A_1$ corresponds to formula (IVa)
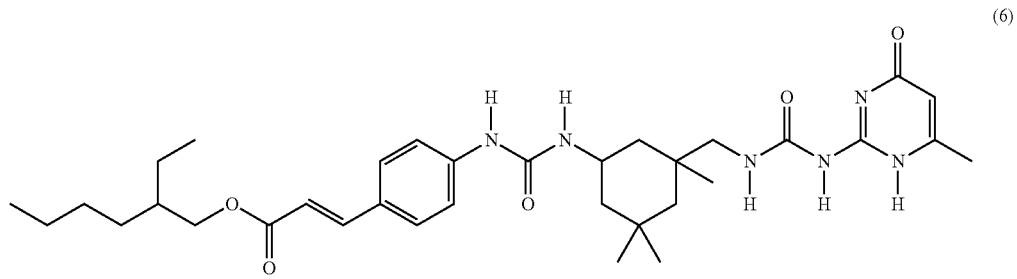 [SMILES: CCCCC(CC)COC(=O)/C=C/c1ccc(NC(=O)NC2CC(C)(C)CC(C)(CNC(=O)Nc3nc(=O)cc(C)[nH]3)C2)cc1]
(6)
   those of formula (IIb) for which $A_2$ corresponds to formula (IVb)
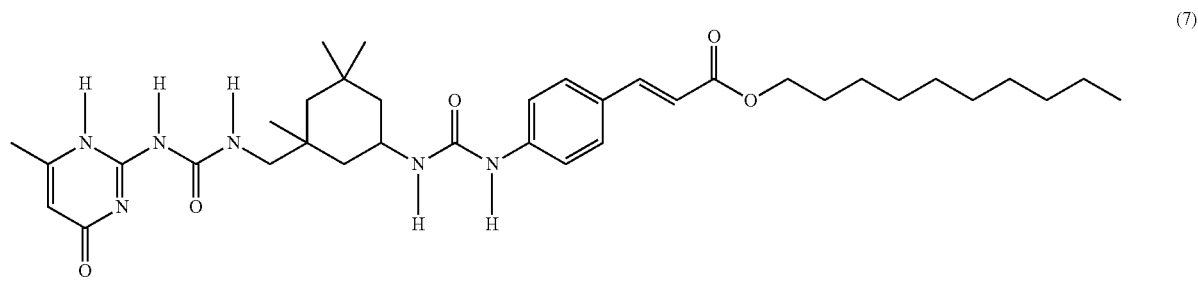
(7)
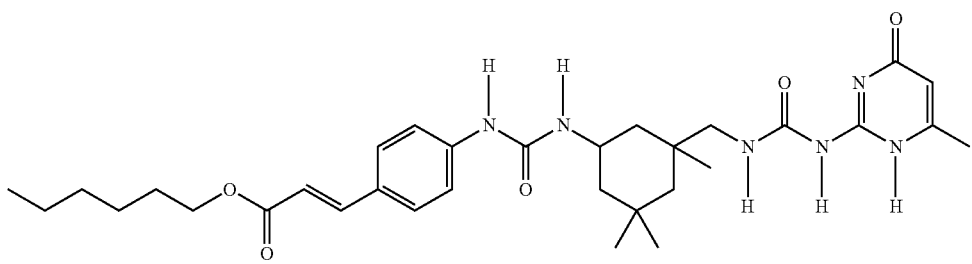
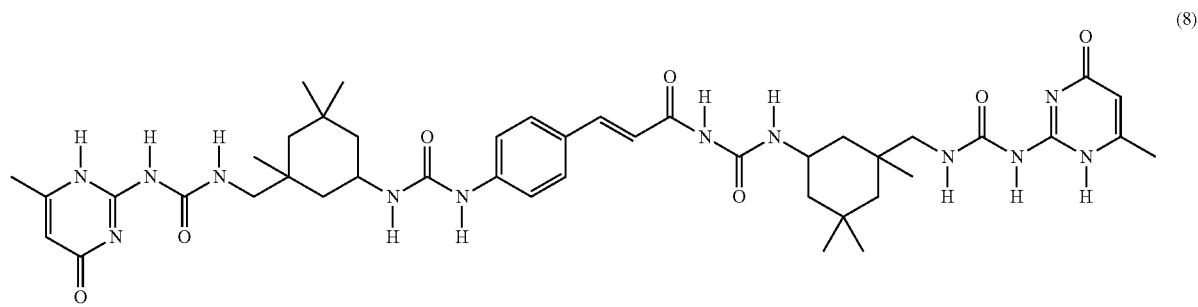
(8)

3/ Benzalmalonate Derivatives of Formula (Ib) for which $A_1$ corresponds to Formula (IVa):
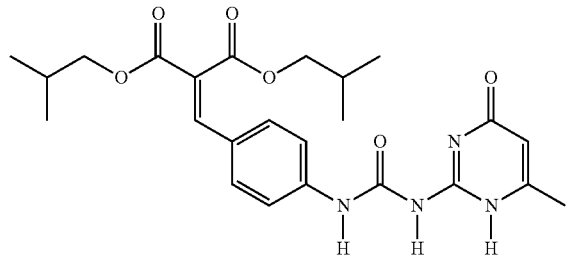
(9)
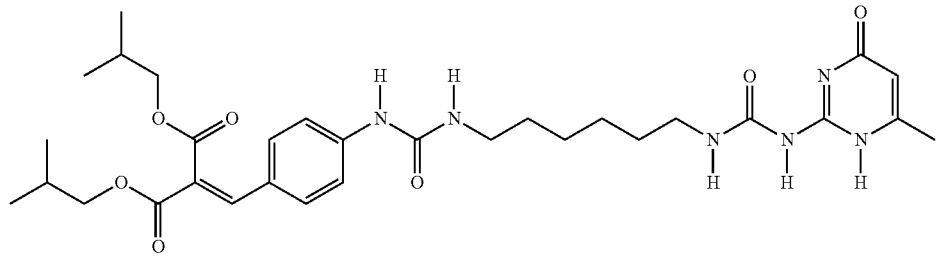
(10)
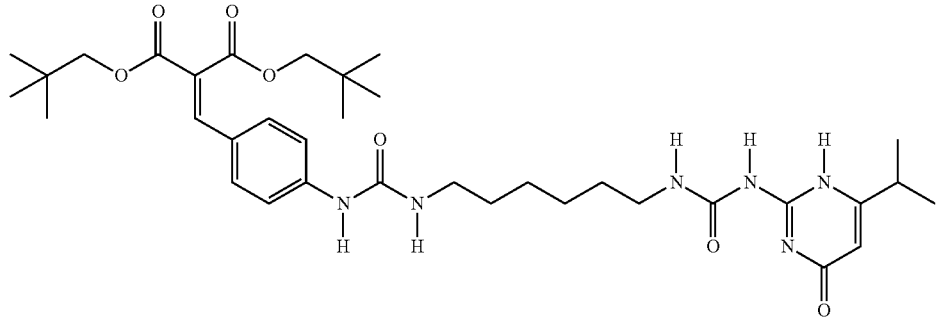
(11)
4/ Cyanoacrylate Derivatives:
  those of formula (Ib) for which $A_1$ corresponds to formula (IVa)
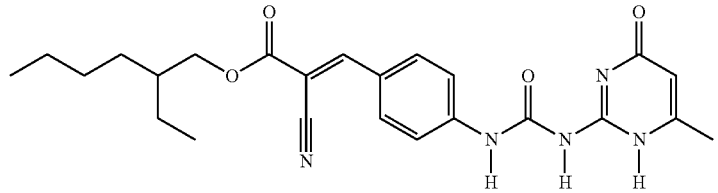
(12)
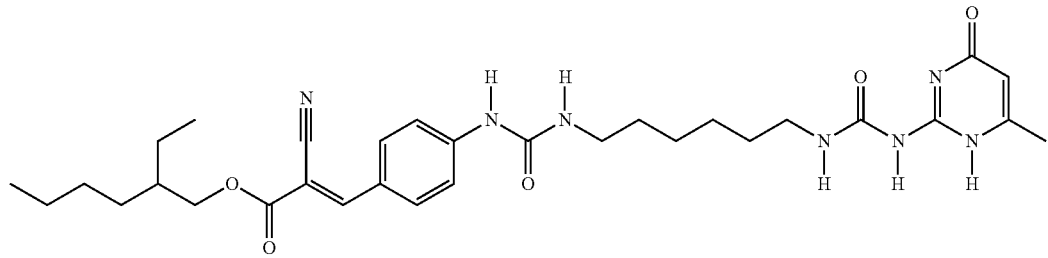
(13)

(14)
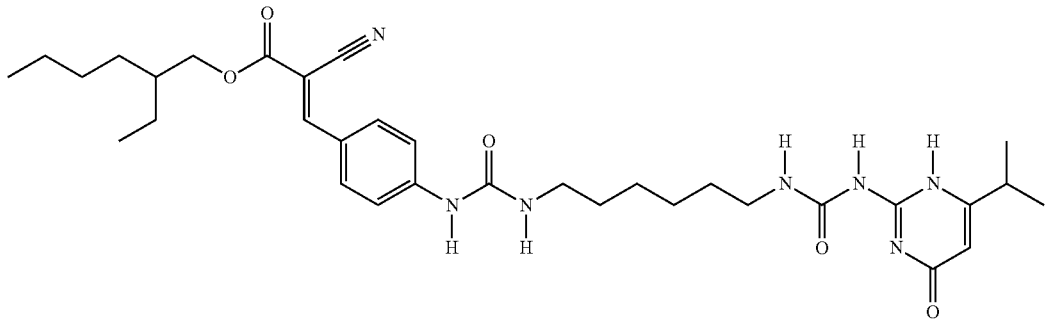
15
those of formula (IIb) for which $A_2$ corresponds to formula (IVb)
(15)
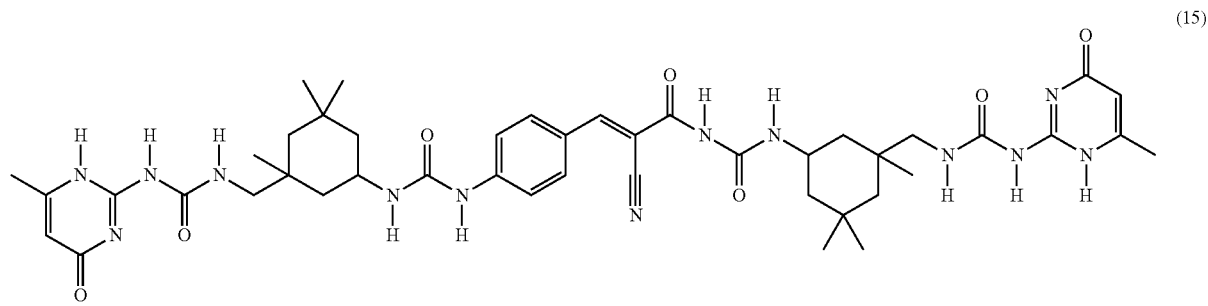
5/ Benzophenone Derivatives of Formula Ib in which $A_1$ Corresponds to Formula (Va):
(16)
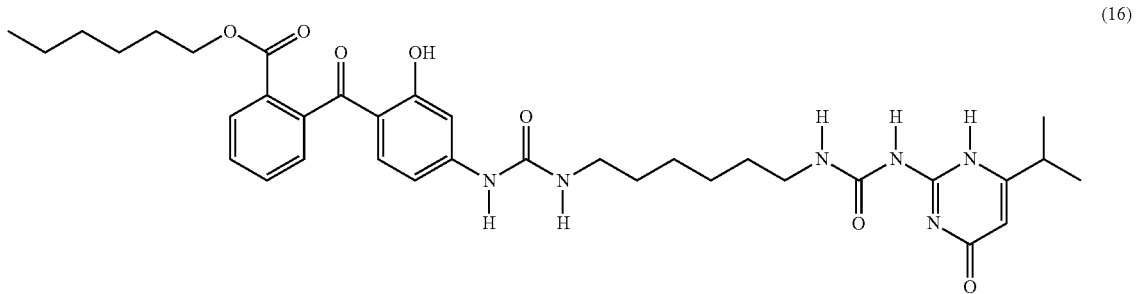 [SMILES: CCCCCCOC(=O)c1ccccc1C(=O)c1ccc(NC(=O)NCCCCCCNC(=O)Nc2nc(=O)cc(C(C)C)[nH]2)cc1O]
6/ Benzylidenecamphor Derivatives:
  those of formula (Ib) for which $A_1$ corresponds to formula (IVa)
(17)
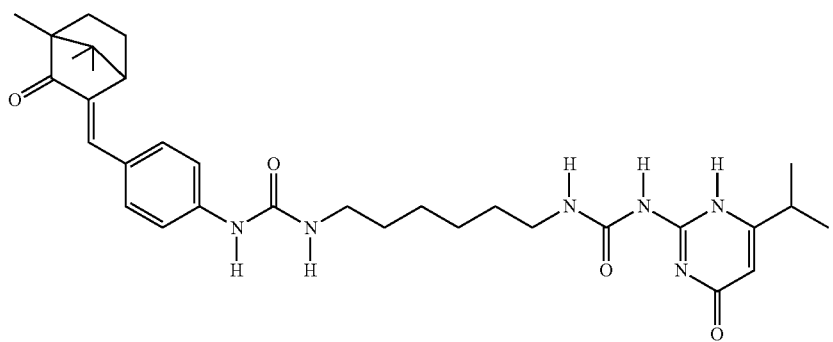

those of formula (Ib) for which $A_1$ corresponds to formula (VIIa)
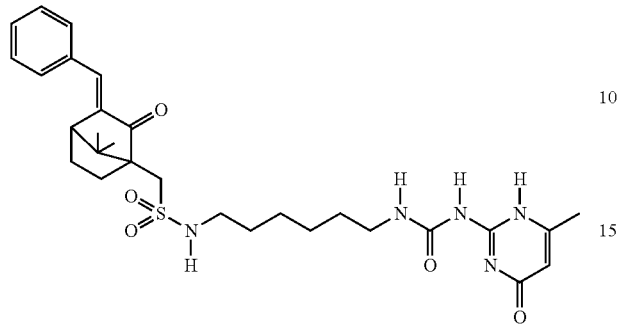
(18)
those of formula (IIb) for which $A_2$ corresponds to formula (VIb)
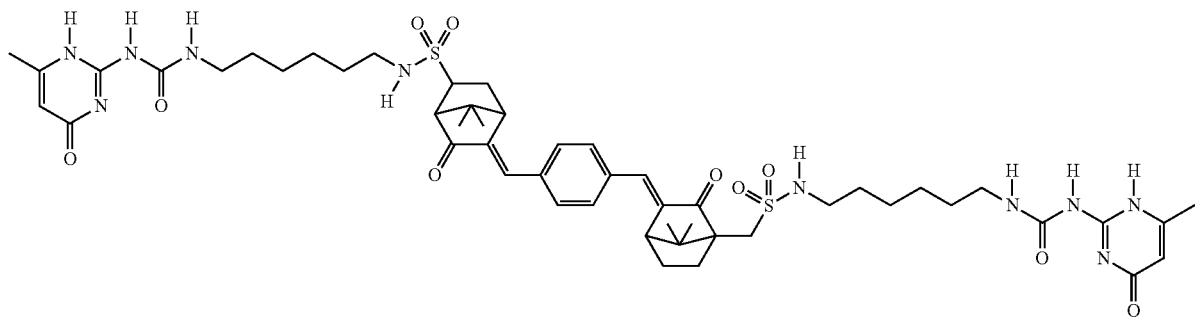
(19)
7/ Benzotriazole Derivatives:
those of formula (Ib) for which $A_1$ corresponds to formula (IXa)
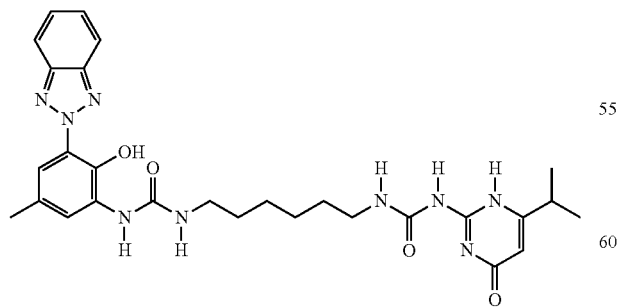
(20)
those of formula (Ib) for which $A_1$ corresponds to formula (Xa)

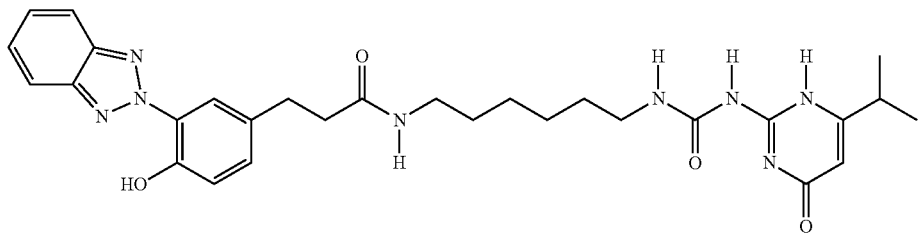
(21)
8/ s-Triazine Derivatives:
those of formula (Ib) for which $A_1$ corresponds to formula (XIIa)
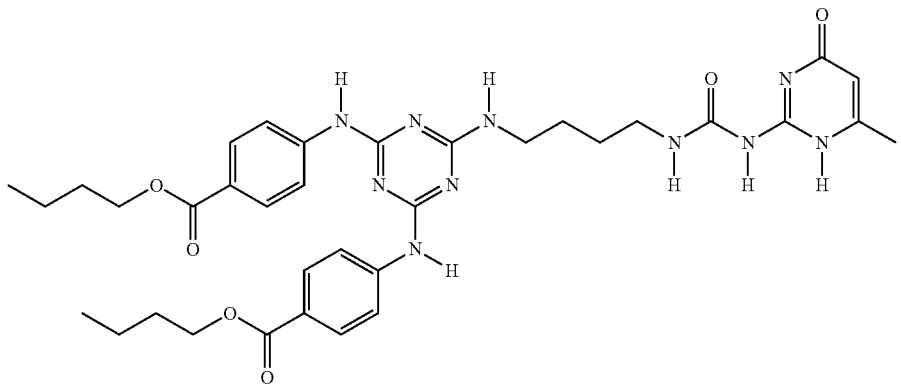
(22)
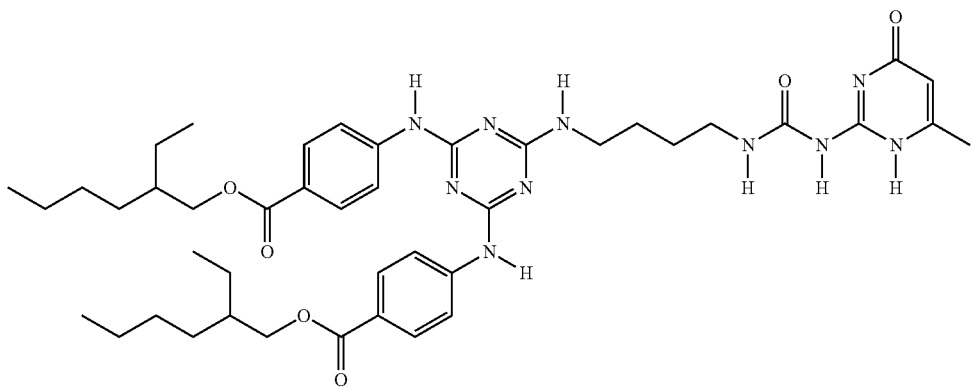
(23)
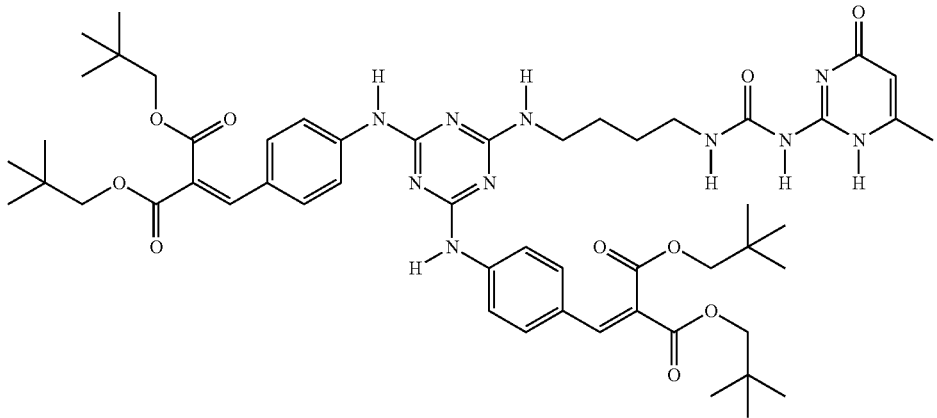
(24)

(25)
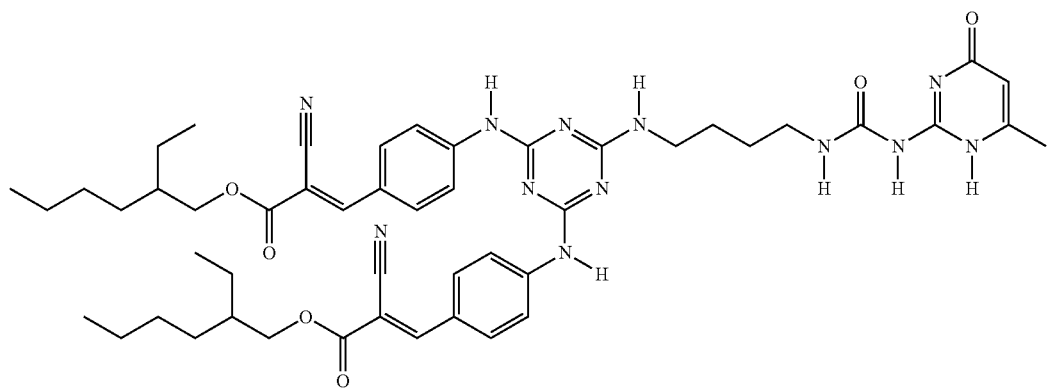
those of formula (IIb) for which $A_2$ corresponds to formula (VIIb) in which $A_4$ represents a radical of formula (IVa)
(26)
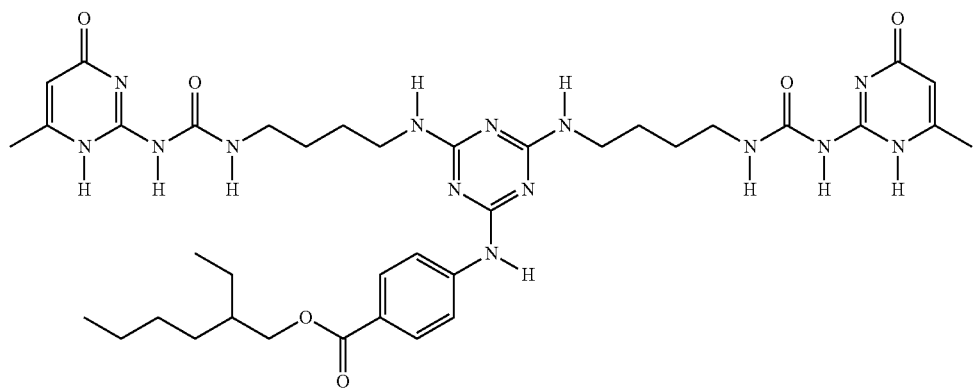
(27)
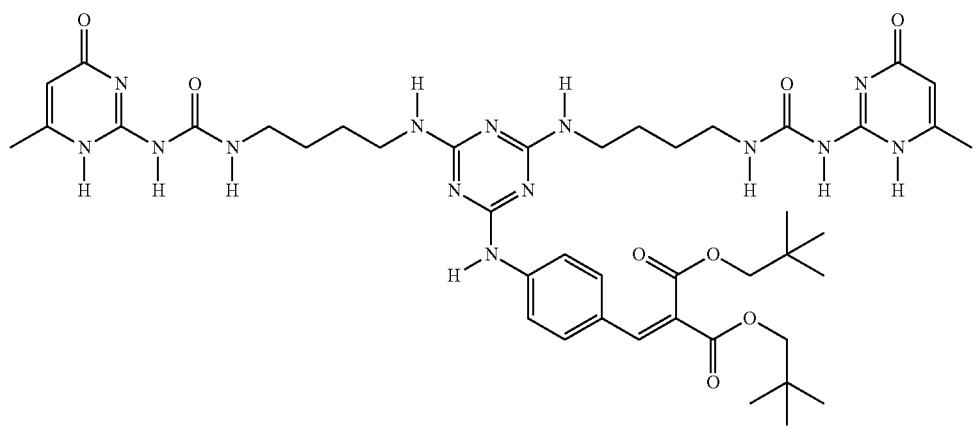

-continued

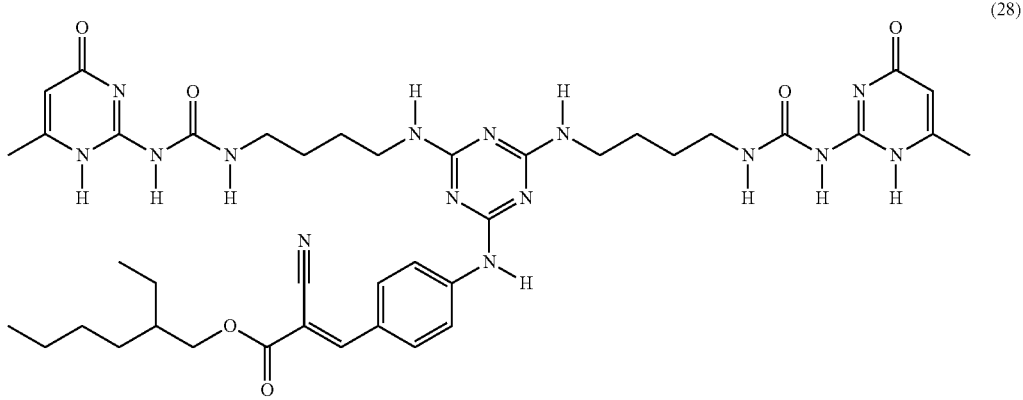

(28)

The compounds of formula (Ib) may be obtained by reaction between a reactive function Y linked to group $A'_1$, with a reactive function W attached to Z of the derivative of formula (XIII), the two reactive functions obviously being capable of reacting together, as described in the scheme below.

The compounds of formula (IIb) may be obtained by reaction between a reactive function Y linked to group $A'_2$, with a reactive function W attached to $Z_1$ of the derivative of formula (XIII), the two reactive functions obviously being capable of reacting together, as described in the scheme below.

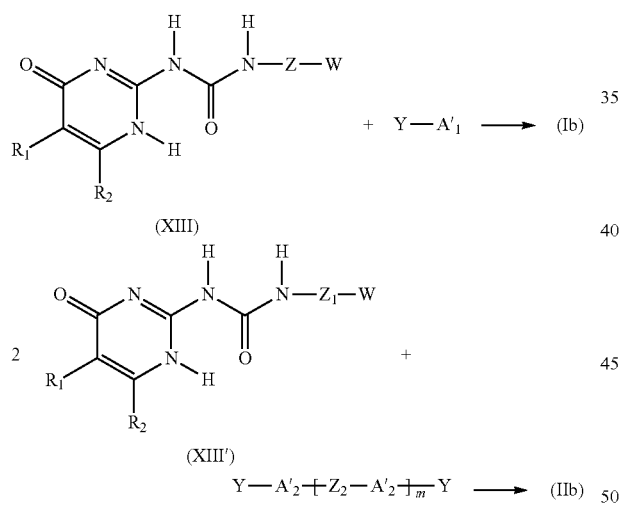

$A'_1$ and $A'_2$ are such that, after reaction between the reactive groups W and Y, the compounds (Ib) and (IIb) containing, respectively, the radicals A1 and A2 are obtained.

The reactive functions W and Y may preferably be chosen from the following functions:

isocyanate —N=C=O;
isothiocyanate —N=C=S;
acid or carboxylic ester —COOR$_a$ or activated ester COOR$_b$ with R$_a$ being H or a linear or branched $C_1$-$C_4$ alkyl radical and better still a methyl or ethyl radical; and OR$_b$ being chosen from phenoxy, 4-nitrophenoxy, 2,4,5-trichlorophenoxy and the following radicals:

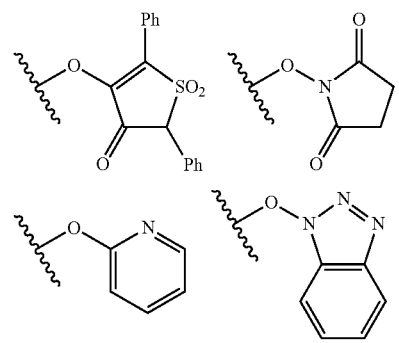

acyl halide,
acyl imidazole or acyl benzotriazole of formula:

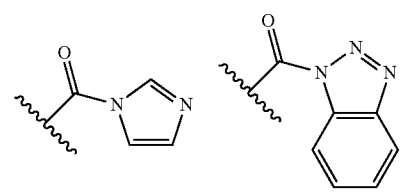 [SMILES: *C(=O)n1ccnc1 ; *C(=O)n1nnc2ccccc21]

acid anhydride;
activated carbamic acid —NHCOX with X=Cl, imidazole or OR$_b$ with OR$_b$ as defined above;
hydroxyl (OH) or activated hydroxyl, for example in O-tosylate form;
primary or secondary amine —NHR$_a$, in which R$_a$ is as defined above.

Preferably, the reactive functions W and Y that are precursors of the bond between Z or $Z_1$ and $A_1$ or $A_2$ (or $A'_1$ and $A'_2$) are chosen from isocyanate, amine and hydroxyl functions.

One particular method for obtaining the derivative of formula (XIII) or (XIII') is the one described in the article by Katritzky et al., Comprehensive Organic Functional Group Transformations, Pergamon: Oxford, 1995, vol. 6, pp. 500-506 or in Arkiv der Pharmazie, 314(1), 34-41, 1981.

To obtain compound (XIII), it is especially possible to react:

an isocytosine B with an activated carbamic acid:

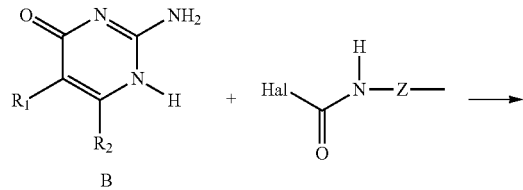

an isocytosine B with an amine-derived isocyanate:

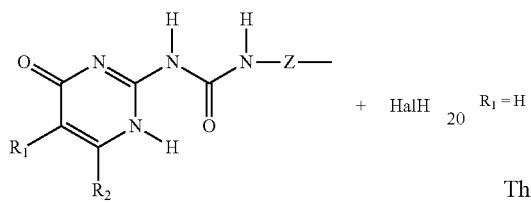

an isocytosine containing an activated carbamic function C with an amine:

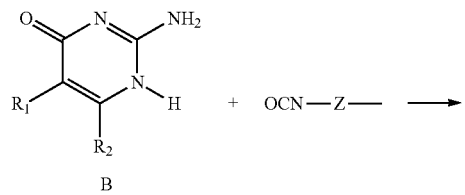

a β-keto ester D (with $R_1$ being H) with a guanylalkylurea derivative E:

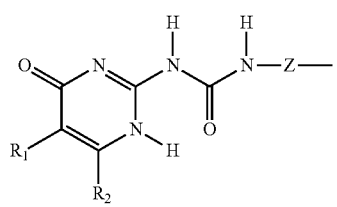

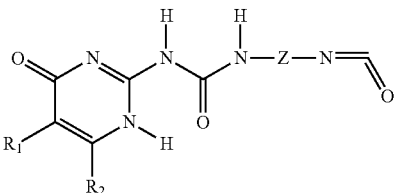

$R_1 = H$

The process is performed in the same manner to obtain the compounds (XIII').

Another process for preparing the derivatives of formula (Ib) or (IIb) for which w=1 consists in synthesizing the following compound (with $R_1$=H and $R_2$=methyl):

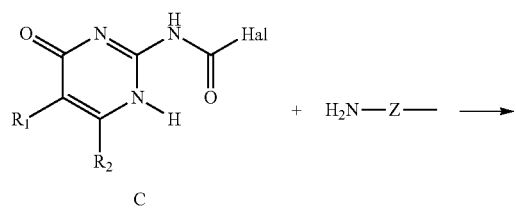

$R_1 = H$  $R_2 = CH_3$ and then in reacting it with (respectively) the function(s) Y=alcohol or amine of the compound Y-A'$_1$ (or, respectively, of the compound Y-A'$_2$-[Z$_2$-A'$_2$]$_m$-Y).

Another process for preparing the derivatives of formula (Ib) or (IIb) consists in synthesizing the following compound (with $R_1$=H and $R_2$=methyl):

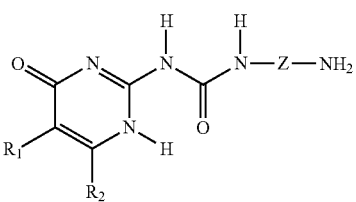

$R_1 = H$  $R_2 = CH_3$ and then in reacting it with (respectively) the function(s) Y=activated carboxylic acid or sulfonic acid of the compound Y-A'$_1$ (or, respectively, of the compound Y-A'$_2$-[Z$_2$-A'$_2$]$_m$-Y).

7/ Hyaluronic Acid

The cosmetic active agent may also be a hyaluronic acid derivative, and comprise both units (Ia) and (Ib):

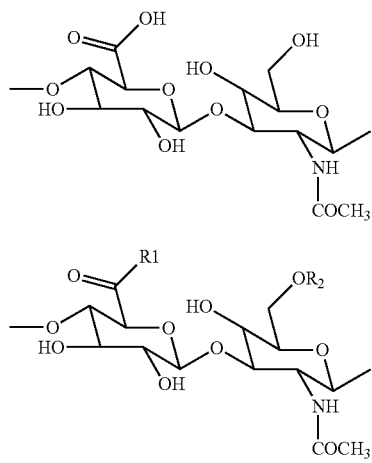

in which:
- $R_1$ represents OH or an —NH—R'—Z radical,
- R2 represents H or a radical —C(O)—NH—R'—Z, with:
  - R' is a linear or branched, divalent C1-C18, in particular C2-C14, indeed even C4-C10, alkyl radical; or a single bond;
  - Z is a radical of formula (I):

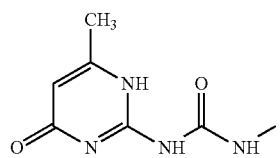

it being understood that at least one, and preferably only one, of the radicals R1 and R2 comprises a radical Z.

Preferably, the ratio between the units (Ia) and the units (Ib) is such that the degree of functionalization of the derivative is between 1% and 99%, better still between 1.5% and 60% and preferentially between 2% and 30%.

Preferably, the derivatives according to the invention advantageously have an average molecular weight (Mw) of between 5000 and 3 000 000 daltons, better still between 50 000 and 2 500 000 daltons, indeed even between 500 000 and 2 000 000 daltons.

The hyaluronic acid derivatives may also be in the form of salts, in particular sodium, ammonium or potassium salt.

8/ Capsules

The capsules according to the invention may be obtained by reaction between:
- on the one hand, at least one preformed capsule, bearing at least one reactive function, especially at the surface, said reactive function possibly being nucleophilic or electrophilic, and
- on the other hand, at least one junction group capable of establishing hydrogen bonds with one or more partner junction groups, each junction group pairing involving at least 3 hydrogen bonds, said junction group bearing at least one reactive function capable of reacting with the reactive function borne by said capsule, said junction group comprising at least one unit of formula (I) or (II) as defined hereinbelow.

The preformed capsule is preferably obtained by organic and/or mineral covalent polymerization. It may especially be obtained by radical polymerization and/or by polycondensation.

Mention may be made in particular of capsules of crosslinked polyurethane, polyurea and/or polyurethane/polyurea type, obtained especially by interfacial polycondensation; such capsules are especially described in patent application EP 1 837 073.

The non-functionalized capsules may especially be obtained by reacting at least two reagents, one of isocyanate type and the other of alcohol and/or amine type, at least one of these reagents bearing at least 3 identical or different functions, chosen, for one, from isocyanate functions, and, for the other, from hydroxyl and amine functions. This reagent especially ensures the crosslinking function.

According to a first embodiment variant, the capsule may be obtained by reacting a reagent of alcohol and/or amine type comprising at least three identical or different functions chosen from hydroxyl and amine functions, with a reagent of isocyanate type comprising only one, or preferably even two, isocyanate function(s). According to another embodiment variant, the capsule may be obtained by reacting a triisocyanate or a polyisocyanate with a reagent of alcohol and/or amine type comprising only one, or preferably even two, function(s), which may where appropriate be identical or different, chosen from hydroxyl and amine functions.

Reagents of Isocyanate Type

The reagents of isocyanate type that may be used to form the capsules according to the invention may comprise one or more, and especially two, or even three isocyanate functions. They may be chosen, for example, from aliphatic, cycloaliphatic, araliphatic, aromatic and heterocyclic di- or polyisocyanates such as those described, for example, by W. Siefken in Justus Liebigs Annalen der Chemie, 562, pages 75 to 136.

According to one embodiment of the invention, the reagents of isocyanate type may be chosen from diisocyanates, and especially ethylene diisocyanate, 1,4-tetramethylene diisocyanate, 1,6-hexamethylene diisocyanate, 2,2,4- or 2,4,4-trimethyl-1,6-hexamethylene diisocyanate, 1,12-dodecane diisocyanate, cyclobutane 1,3-diisocyanate, cyclohexane 1,3- and 1,4-diisocyanate, and any mixture of the isomers thereof, 4,4'-methylenebis(cyclohexyl)diisocyanate, 1-isocyanato-3,3,5-trimethyl-5-isocyanatomethylcyclohexane, 2,4- and 2,6-hexanehydrotolylene diisocyanate and any mixture of the isomers thereof, hexahydro-1,3- and 1,4-phenylene diisocyanate, perhydro-1,4'- and 4,4'-diphenylmethane diisocyanate, 1,3- and 1,4-phenylene diisocyanate, 2,6-tolylene diisocyanate and any mixture of the isomers thereof, 4,4'-diphenylmethane diisocyanate (4,4'-MDI), 1,5-naphthylene diisocyanate, m-xylylene diisocyanate, tetramethylxylylene diisocyanate, m- and p-isocyanatophenylsulfonyl isocyanates, lysine alkyl ester diisocyanate in which the alkyl is of $C_1$ to $C_{10}$, or 2-butyl-2-ethylpentamethylene diisocyanate, and mixtures thereof.

According to another embodiment of the invention, the reagents of isocyanate type may comprise at least three isocyanate functions and may thus act as crosslinking agent. They may then be chosen especially from triisocyanates, for instance tri-phenylmethane 4,4',4"-triisocyanate, or 4-isocyanatomethyl-1,8-octanemethylene diisocyanate, or alternatively from polyisocyanates, and especially polyphenylpolymethylene polyisocyanates, perchlorinated aryl polyisocyanates, polyisocyanates containing carbodiimide groups, polyisocyanates containing allophanate groups, polyisocyanates containing isocyanurate groups, polyisocyanates containing acylated urea groups, polyisocyanates containing bis-urea groups, polyisocyanates prepared by telomerization reaction, polyisocyanates containing ether groups, the products of reaction of the isocyanates mentioned above with acetals, polyisocyanates containing polymeric fatty acid radicals, and any mixture of the polyisocyanates mentioned above.

It is also possible to use, as reagent of isocyanate type, mixtures of said isocyanates, i.e. mixtures of aliphatic isocyanates, mixtures of aromatic isocyanates, mixtures of aliphatic and aromatic isocyanates, and in particular mixtures optionally comprising modified diphenylmethane diisocyanates.

Illustrations of these mixtures that may especially be mentioned include biuret hexamethylene diisocyanate mixed with 4,4'-diphenylmethane isocyanate, and optionally with 2,4-diphenylmethane isocyanate, trimerized hexamethylene diisocyanate, mixed with 4,4'-diphenylmethane diisocyanate, and optionally with 2,4-diphenylmethane diisocyanate.

It is also possible to use, as reagent of isocyanate type, oligo- or polyisocyanates that may be prepared from the di- or polyisocyanates mentioned above or mixtures thereof by bonding them using urethane, allophanate, urea, bis-urea, amide, isocyanurate, carbodiimide, uretonimine, oxadiazinetrione or iminooxadiazinedione structures.

Mention may also be made of di- or polyisocyanates, such as mixtures of diphenylmethane diisocyanate monomers and of diphenylmethane diisocyanate oligomers (also known as MDI polymers), 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl)diisocyanate and 4-methylcylcohexane 1,3-diisocyanate (H-TDI), which may be used more particularly as reagent of isocyanate type.

Thus, according to one preferred embodiment, the reagents of isocyanate type that may be used to form the capsules according to the invention are chosen from di- or polyisocyanates and especially mixtures of diphenylmethane diisocyanate monomers and of diphenylmethane diisocyanate oligomers (MDI polymers), tolylene diisocyanate (TDI), and especially 2,4-tolylene diisocyanate and 2,6-tolylene diisocyanate, and also the mixture thereof, 4,4'-diphenylmethane diisocyanate (4,4'-MDI), or alternatively isophorone diisocyanate (IPDI).

The amount of reagent of isocyanate type to be used for the implementation of the invention varies within the range usually used in interfacial polyaddition processes.

Reagents of Alcohol and/or Amine Type

The reagents of alcohol and/or amine type that may be used to form the capsules according to the invention may comprise one or more, and especially two, or even three, identical or different functions chosen from hydroxyl and amine functions. They may be chosen, for example, from reagents of alcohol type, reagents of amine type and reagents of amino alcohol type, used alone or as mixtures. They preferably have a molecular weight ranging from 200 to 4000 g/mol.

The reagents of alcohol type may comprise one or more, and especially two, or even three, hydroxyl functions.

More particularly, these reagents may be a polyol. For the purposes of the invention, the term "polyol" means any organic molecule comprising in its chemical structure at least two hydroxyl groups —OH. The polyol may be, for example, a linear, branched or cyclic, saturated or unsaturated hydrocarbon-based compound bearing at least two hydroxyl functions. The polyol may in particular be a (hydro)carbon-based compound preferably comprising from 2 to 300 carbon atoms, and bearing at least two hydroxyl groups and preferably from 2 to 10 hydroxyl groups.

Preferably, it is a (hydro)carbon-based compound containing from 3 to 32 carbon atoms, especially from 4 to 18 carbon atoms or even from 4 to 12 carbon atoms. In particular, the polyol may be a compound containing from 2 to 18 carbon atoms and from 2 to 6 hydroxyl functions.

According to one embodiment of the invention, the reagents of alcohol type may be chosen from diols and especially glycol derivatives such as diethylene glycol, dipropylene glycol, ethylene glycol, propylene glycol, hexylene glycol, isoprene glycol, butylene glycol and pentylene glycol, or alternatively butanediol, 1,2-propanediol, pentanediols and in particular 1,2-pentanediol and dodecanediol, or mixtures thereof.

According to another embodiment of the invention, the reagents of alcohol type may comprise at least three hydroxyl functions, and may thus act as crosslinking agent. They may then be chosen especially from trimethylolpropane, glycerol, pentaerythritol, 1,2,3-trihydroxyhexane, erythritol, arabitol, adonitol, dulcitol and sorbitol, glycerol polymers and copolymers, for instance hexaglycerol and diglycerol, glycerol derivatives, for instance butyldiglycol, polyglyceryl-3 diisostearate and castor oil, glycol derivatives, for instance polyethylene glycols and especially polyethylene glycols (PEG) containing from 4 to 150 ethylene glycol units, for instance PEG-400, PEG-600, PEG-800 and PEG-1200, polypropylene glycols, copolymers of ethylene glycol and of propylene glycol, or alternatively sugars such as glucose, fructose, xylose, trehalose, sucrose, maltose and lactose, and mixtures thereof. Preferably, the reagents of alcohol type that are useful for acting as crosslinking agent are chosen from trimethylolpropane, glycerol, pentaerythritol and sugars. The polyol may also be a polyether alcohol with an average molecular weight ranging from 150 to 600, such as polyethylene glycol 300 and polyglycerol 500. It is also possible to use any mixture of the polyols mentioned above.

The polyol may also be chosen from non-etherified polyols and non-esterified polyols.

According to a preferred embodiment, the reagents of alcohol type are chosen from diols, for instance diethylene glycol, polyols, for instance polyethylene glycols, and especially those containing from 4 to 150 ethylene glycol units, or alternatively mixtures of polyethylene glycols and of diethylene glycol.

The reagents of amine type may comprise one or more, and especially two, or even three, amine functions.

According to one embodiment of the invention, the reagents of amine type may be chosen from diamines, for instance diaminoethane, diaminopropanes, diaminobutanes, diaminohexanes, piperazine, 2,5-dimethylpiperazine, amino-3-aminomethyl-3,5,5-trimethylcyclohexane (isophorone diamine, IPDA), 4,4'-diaminodicyclohexylmethane, 1,4-diaminocyclohexane, aminoethylethanolamine, hydrazine or hydrazine hydrate.

According to another embodiment of the invention, the reagents of amine type may comprise at least three amine functions, and may thus act as crosslinking agent. They may then be chosen especially from triamines, for instance guanidine, diethylenetriamine or 1,8-diamino-4-aminomethyloctane.

The reagents of amine type may also be used in the form of ketimines, ketazines or corresponding amine salts.

According to a preferred embodiment, the reagents of amine type comprise at least one amino group chosen from primary amine and secondary amine groups of the type NHR, in which R represents an alkyl group containing from 1 to 8 carbon atoms.

The reagents of amino alcohol type may comprise at least two different functions chosen from amine and hydroxyl functions.

According to one embodiment of the invention, the reagents of amino alcohol type may be difunctional, i.e. they may comprise two functions, namely an amine function and a hydroxyl function.

According to another embodiment of the invention, the reagents of amino alcohol type may comprise at least three functions, and may thus act as crosslinking agent. They may comprise, for example, a single hydroxyl (or, respectively, amine) function and at least two amine (or, respectively, hydroxyl) functions, or alternatively two hydroxyl (or, respectively, amine) functions and at least one amine (or, respectively, hydroxyl) function.

As reagents of amino alcohol type that may be used in the present invention, mention may be made especially of ethanolamine and triethanolamine.

As mentioned previously, the capsules according to the invention may, according to a first alternative, be obtained by reacting at least one diisocyanate with at least one reagent of alcohol and/or amine type bearing at least three identical or different functions, chosen from hydroxyl and amine functions, and acting as crosslinking agent, optionally in the presence of at least one diol and/or of at least one diamine and/or of at least one difunctional amino alcohol.

Preferably, the reagent of isocyanate type is a diisocyanate chosen from mixtures of diphenylmethane diisocyanate monomers and of diphenylmethane diisocyanate oligomers (MDI polymers), tolylene diisocyanate (TDI) and especially 2,4-tolylene diisocyanate and 2,6-tolylene diisocyanate, and also a mixture thereof, 4,4'-diphenylmethane diisocyanate (4,4'-MDI), or alternatively isophorone diisocyanate (IPDI).

Examples of reagents acting as crosslinking agent that may be used include the triols, polyols, triamines and polyamines described previously. Preferably, the reagent acting as crosslinking agent is chosen from triols, for instance trimethylolpropane, glycerol and pentaerythritol, and polyols, for instance sugars such as glucose, fructose, xylose, trehalose, sucrose, maltose and lactose. Preferably, the diamines comprise at least one amino group chosen from primary amine and secondary amine groups of the type —NHR, in which R represents an alkyl group containing from 1 to 8 carbon atoms.

Preferably, the capsules are obtained by interfacial polymerization. Interfacial polycondensation is a polymerization reaction that takes place at the interface of two immiscible liquids, at least one of the two containing a suitable polyfunctional reagent. Preferably, at least one monomer and/or reagent is soluble in the first phase and at least one monomer and/or reagent is soluble in the second phase, which is immiscible with said first phase.

When this reaction takes place without removal of side products, it is also known as interfacial polymerization.

This reaction may especially be performed in an emulsion, especially a two-phase or a multi-phase emulsion, at the interface between the immiscible phases. The reaction may be performed in an emulsion of oil-in-water or water-in-oil type, or alternatively in a multiple emulsion of the W/O/W or O/W/O type. According to one preferred embodiment, the emulsion is of the oil-in-water type.

The capsules are crosslinked. This crosslinking may be obtained by reacting the polymer chains with a reagent having a functionality at least equal to 3, known as a crosslinking agent.

The capsules according to the invention, before functionalization, preferably have a size of between 0.5 and 1200 microns and especially between 0.6 and 30 microns.

In one particular embodiment, the capsules may comprise an encapsulated active agent.

Said encapsulated active agent may especially be a dyestuff, in particular a pigment, i.e. a white or colored solid particle, which is naturally insoluble in the liquid hydrophilic and lipophilic phases usually used in cosmetics, or which is rendered insoluble by formulation in the form of a lacquer, for example. Said pigment is preferably at least partly organic, or even totally organic. It may also be mineral.

The capsules preferably comprise from 0.5% to 80% by weight, especially from 1% to 70% by weight, especially from 20% to 65% by weight or even from 30% to 60% by weight of pigment relative to the weight of the capsule.

Mention may be made especially of carbon black, pigments of D&C and FD&C type, and lakes thereof, and especially those known under the names D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 6, FDC Blue 1, D&C Yellow No. 7, D&C Yellow No. 8, D&C Yellow No. 10 or D&C Yellow No. 11; and also lakes thereof, especially lakes based on barium, strontium, calcium or aluminum, or alternatively diketopyrrolopyrroles.

Dyestuffs that may also be mentioned include mineral pigments, optionally surface-treated and/or coated, and especially titanium dioxide, zirconium oxide or cerium oxide, zinc oxide, iron oxide (black, yellow or red) or chromium oxide, manganese violet, ultramarine blue, chromium hydrate and ferric blue, or alternatively metal powders, for instance aluminum powder, copper powder, gold powder and silver powder.

Mention may also be made of pigments having an optical effect, such as particles comprising a natural or synthetic and organic or mineral substrate, for example glass, acrylic resins, polyester, polyurethane, polyethylene terephthalate, ceramics or aluminas, said substrate being covered or not covered with metal substances, such as aluminum, gold, silver, platinum, copper or bronze, or with metal oxides, such as titanium dioxide, iron oxide or chromium oxide.

Among the dyestuffs, mention may also be made of nacres, i.e. iridescent pigments produced especially by certain molluscs in their shell, or else synthesized. The nacres may be chosen from mica coated with titanium or with bismuth oxychloride, titanium mica coated with iron oxides, titanium mica coated with ferric blue or with chromium oxide, titanium mica coated with an organic pigment, and also nacreous pigments based on bismuth oxychloride.

Use may also be made of interference pigments, especially liquid-crystal or multi-layer interference pigments; or pigments with a structure of silica microsphere type containing iron oxide.

The dyestuffs may also be dyes (soluble), among which mention may be made of those listed in annex IV, such as D&C Red 27, D&C Red 21, D&C Orange No. 5, D&C Yellow 11, D&C Green 6, D&C Violet 2, Red 4, Red 6, D&C Red 22, Red 28, D&C Red 30, Red 33, Orange 4, Yellow 5, Yellow 6, D&C Yellow No. 8, D&C Green 5, FDC Green 3, FDC Blue 1; *Beta Vulgaris*; bismuth oxychloride; bromo-cresol green; bromothymol blue; capsanthin/capsorubin; caramel; CI-10006; CI-10020; CI-10316; CI-11920; CI-12010; CI-12150; CI-12700; CI-13015; CI-14270; CI-14700; CI-14720; CI-14815; CI-15620; CI-15980; CI-15985; CI-16035; CI-16185; CI-16230; CI-16255; CI-16290; CI-17200; CI-18050; CI-18130; CI-18690; CI-18736; CI-18820; CI-18965; CI-19140; CI-20170; CI-20470; CI-21230; CI-24790; CI-26100; CI-27290; CI-27755; CI-28440; CI-40800; CI-40820; CI-40825; CI-40850; CI-42045; CI-42051; CI-42053; CI-42080; CI-42090; CI-42100; CI-42170; CI-42510; CI-42520; CI-42735; CI-44045; CI-44090; CI-45100; CI-45190; CI-45220; CI-45350; CI-45370; CI-45370; CI-45380; CI-45380; CI-45380; CI-45396; CI-45405; CI-45410; CI-45425; CI-45430; CI-47000; CI-47005; CI-50325; CI-50420; CI-59040; CI-60725; CI-60730; CI-61565; CI-61570; CI-61585; CI-62045; CI-73015; CI-73900; CI-75100; CI-75120; CI-75125; CI-75130; CI-75135; CI-75300; CI-75810; CI-77713; CI-77820; CI-77891; CI-77947; CI-40215; CI-74180; CI-75470; Acid Red 195; CI-19140; CI-45370; CI-47005; CI-75810; CI-75810; ribo-flavin; and mixtures thereof.

The encapsulated active agent may also be a gas, such as air, carbon dioxide or nitrogen; and/or a constituent chosen from cosmetic oils and waxes, which are especially mineral, animal, vegetable or synthetic, and cosmetic active agents such as vitamins, UV-screening agents, fragrances, moisturizers or treating active agents. In general, any type of encapsulable active agent may be envisaged.

The capsules may be prepared by interfacial polymerization, especially in the manner described in EP 1 837 073. They may also be of polyurethane, polyester, polyamide, polycarbonate, polysiloxane, polysaccharide, cellulosic, polyether, polyamine, polypeptide, protein, polyvinyl alcohol or polyvinyl acetate type.

They may also be prepared by radical polymerization, and may be of the poly(C1-C16 alkyl(meth)acrylate) type, especially PMMA; or alternatively polystyrene or copolymers thereof.

The capsules may be copolymers of the above types, or mixtures of these polymers.

The capsules may also be totally or partially mineral, for example of the type such as silica, $TiO_2$, $ZrO_2$, alumina, $SnO_2$ or iron oxide, or mixtures thereof; they may also be of the clay, sepiolite or montmorillonite type, or mixtures thereof.

The capsules may also combine organic polymers with mineral materials.

The preformed capsule thus prepared, by organic or mineral covalent polymerization, must bear at the surface at least one reactive function, which may be nucleophilic or electrophilic, and chosen especially from OH, C=O (carbonyl) and $NH_2$, and which must be capable of reacting with a complementary function borne by the junction group.

In conclusion, the functionalized capsules according to the invention thus comprise at least one part originating from the preformed capsule and at least one part originating from the junction group, said part comprising at least one unit of formula (I) or (II). In particular, said parts are linked via a covalent bond, especially formed during the reaction between the reactive functions borne by the preformed capsule and the reactive functions borne by the junction group.

The junction group that may be used for preparing the functionalized capsule according to the invention bears at least one reactive function and comprises at least one unit of formula (I') or (II') as defined below.

The reactive function may especially be of isocyanate or imidazole type, capable of reacting with the reactive functions of the capsule, so as to form a covalent bond, especially of urea or urethane type, between said capsule and said junction group.

Said junction group is capable of establishing H bonds with one or more partner junction groups, of identical or different chemical nature, each junction group pairing involving at least 3H (hydrogen) bonds, preferably at least 4H bonds and preferentially 4H bonds.

For the purposes of the invention, the term "junction group" means any functional group comprising groups that are H bond donors or acceptors, and capable of establishing at least three H bonds, preferably at least 4H bonds, preferentially 4H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The junction group moreover comprises at least one monovalent unit of formula (I') and/or at least one divalent unit of formula (II'), as defined below:

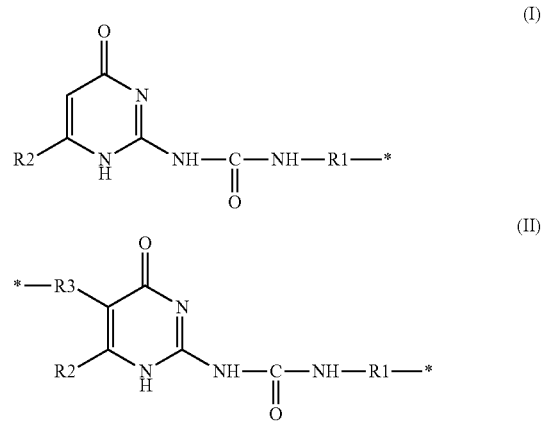

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a methyl group.
The radical R1 may in particular be:
a linear or branched, divalent C2-C12 alkylene group, in particular a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;

a divalent C4-C12 cycloalkylene or arylene group, chosen in particular from the following radicals: -isophorone-, tolylene, 2-methyl-1,3-phenylene, 4-methyl-1,3-phenylene; 4,4'-methylenebiscyclohexylene; 4,4-bisphenylenemethylene; or of structure:

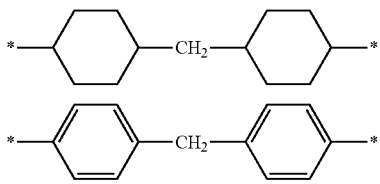

The term "-isophorone-" means the divalent radical having the structure:

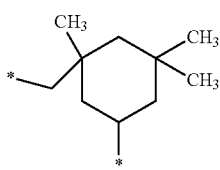 [SMILES: *CC1(C)CC(*)CC(C)(C)C1]

Preferentially, R1 represents -isophorone-, —(CH$_2$)$_6$— or 4,4'-methylenebiscyclohexylene.

Preferably, R3 represents a divalent radical —R'3-O—C(O)—NH—R'4- in which R'3 and R'4, which may be identical or different, represent a divalent carbon-based radical chosen from a linear or branched C$_1$-C$_{32}$ alkyl group, a C$_4$-C$_{16}$ cycloalkyl group and a C$_4$-C$_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; isophorone.

Most particularly, R'3 may represent a C1-C4 alkylene, especially 1,2-ethylene. Preferably, R'4 may represent the divalent radical derived from isophorone.

Most particularly, R3 may have the structure:

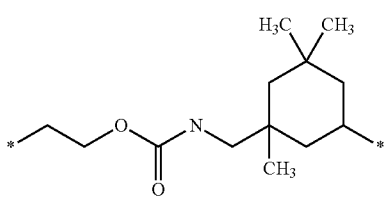 [SMILES: *CCOC(=O)NCC1(C)CC(*)CC(C)(C)C1]

In a particularly preferred manner, the following may apply in formula (I):

R$_1$=-isophorone-, R2=methyl, which gives the unit of formula:

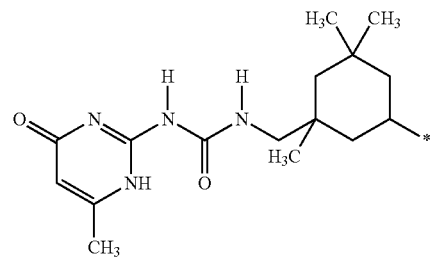

R$_1$=—(CH$_2$)$_6$—, R2=methyl, which gives the unit of formula:

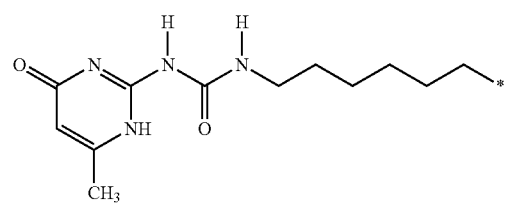

R$_1$=—(CH$_2$)$_6$—, R2=isopropyl, which gives the unit of formula:

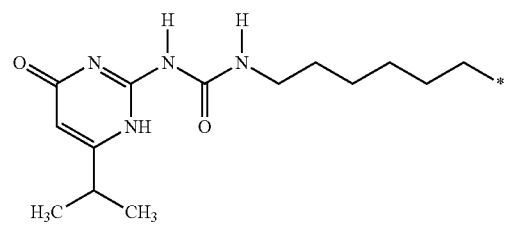

R$_1$=4,4'-methylenebiscyclohexylene and R2=methyl, which gives the unit of formula:

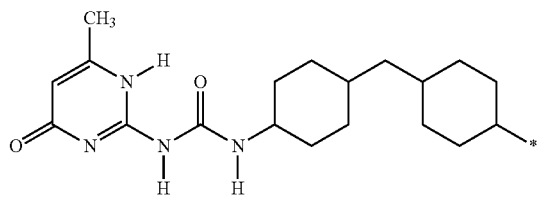

In a particularly preferred manner, in formula (II), R1 represents the -isophorone-radical, R2=methyl and R3=—(CH$_2$)$_2$OCO—NH-isophorone-, which gives the divalent unit of formula:

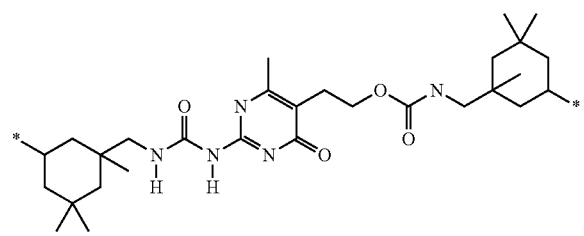

The junction groups bearing only one isocyanate function may have the formula:

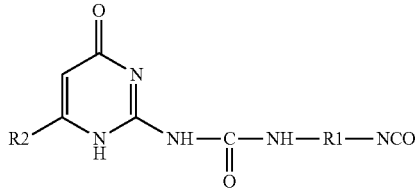

in which R1 and R2 are as defined above; and in particular:
R1 represents -isophorone-, —(CH$_2$)$_6$—, CH$_2$CH(CH$_3$)— CH$_2$—C(CH$_3$)$_2$—CH$_2$—CH$_2$, 4,4'-methylenebiscyclohexylene or 2-methyl-1,3-phenylene.

Preferably, the junction groups may be chosen from the following groups:

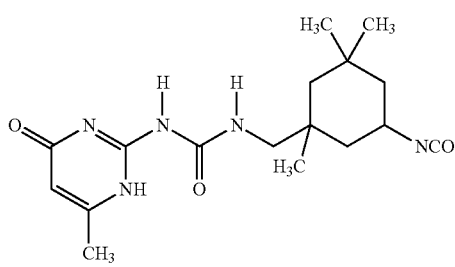

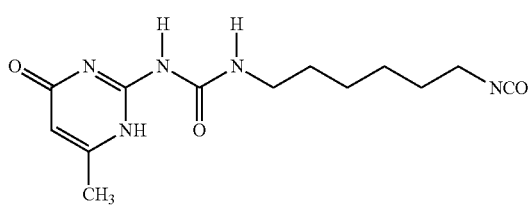

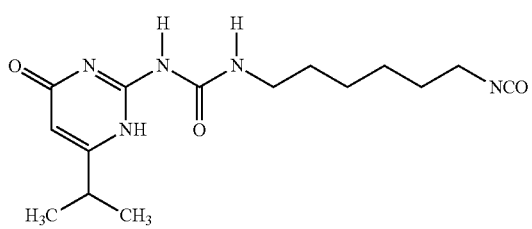

-continued

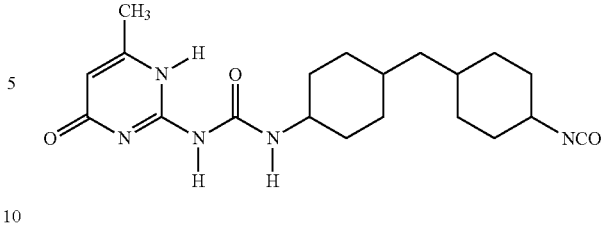

The junction groups bearing two isocyanate functions may have the formula:

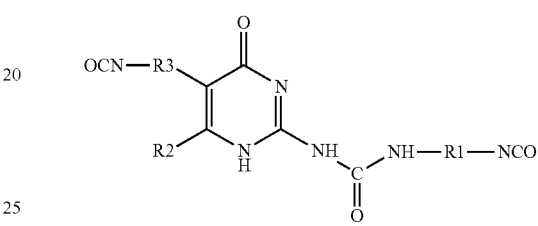

in which R1, R2 and R3 are as defined above, and in particular:

R1 represents -isophorone-, —(CH$_2$)$_2$—, —(CH$_2$)$_6$—, CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or R2 represents CH$_3$; and/or R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or mixtures thereof; and in particular R'3 represents a C$_1$-C$_4$ alkylene, in particular 1,2-ethylene, and R'4 represents the divalent radical derived from isophorone.

A junction group that is most particularly preferred is the one having the formula:

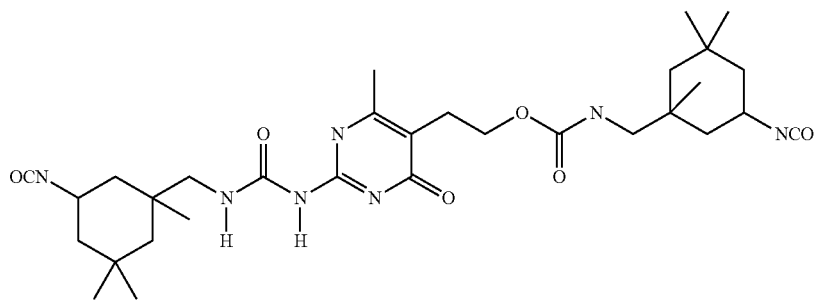

Among the junction groups bearing an imidazole group, mention may be made of the following compound:

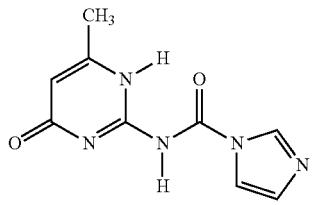 [SMILES: Cc1cc(=O)nc(NC(=O)n2ccnc2)[nH]1]

According to one particular embodiment of the invention, the junction groups may be attached to the capsule by functionalization of the junction group with an isocyanate or imidazole.

According to another embodiment, it is possible to perform the reverse reaction by prefunctionalizing the capsule with a diisocyanate.

In a first preparation method, the functionalized capsule according to the invention may result from the chemical reaction between a preformed capsule bearing a reactive function and a junction group bearing a complementary reactive function. The capsule may be prepared via the processes usually employed by those skilled in the art for forming a urethane bond, between the free OH functions of the capsule and the isocyanate functions borne by the junction group. By way of illustration, a general preparation process consists in:

- heating the capsule bearing at least one reactive function, in particular OH, to a temperature that may be between 25 and 140° C. and especially between 60° C. and 130° C.;
- adding the junction group bearing the reactive functions, in particular isocyanate;
- optionally stirring the mixture, under a controlled atmosphere, at a temperature of about 100-130° C.; for 1 to 24 hours;
- monitoring by infrared spectroscopy the disappearance of the characteristic band for isocyanates (between 2500 and 2800 cm$^{-1}$) so as to stop the reaction on total disappearance of the peak, and then to allow the final product to cool to room temperature.

The reaction may be performed in the presence of a solvent, especially methyltetrahydrofuran, tetrahydrofuran, toluene or butyl acetate. It is also possible to add a conventional catalyst for forming a urethane bond. An example that may be mentioned is dibutyltin dilaurate.

According to the second embodiment, the reaction may include the following steps:
(i) functionalization of the capsule with a diisocyanate, and then
(iia) either reaction with 6-methylisocytosine:
(iib) or reaction with 5-hydroxyethyl-6-methylisocytosine:

An illustration of such a reaction is given in Folmer et al., Adv. Mater., 12, 874-78 (2000).

In one particular embodiment, the topcoat preferably contains, besides the cosmetic active agent, at least one polymer comprising at least one unit (Ia) capable of associating via at least 3 hydrogen bonds with another unit (Ia).

The polymers bearing at least one unit of formula (Ia) that may be used in the cosmetic composition according to the invention are defined below.

Such a polymer may also be present in the mixture of topcoat and basecoat intended to be applied to the keratin materials, as described previously.

Structure of the Polymers

The polymer that may be used in the context of the present invention thus comprises:
(a) a polymer backbone -POL-,
(b) at least one junction group (of formula (I)) linked to said polymer backbone, bearing at least one unit (Ia).

For the purposes of the invention, the term "polymer backbone", also known as POL, means a homopolymer or copolymer, referred to hereinbelow as polymer, comprising at least two identical or different covalently bonded repeating units and better still at least three covalently bonded repeating units. According to the present invention, the term "comprising at least two repeating units" means a consecutive unit of a homopolymer or copolymer resulting from the homopolymerization or copolymerization of at least two identical or different monomer or oligomer units. Said polymer may be linear, cyclic, branched, especially star, dendrimer or grafted, or alternatively crosslinked; it may be a homopolymer or a copolymer, which may be in random, alternating, block or other form.

Preferably, the number-average molecular mass (Mn) of the polymers according to the invention is between 1000 and 3 000 000, especially 5000 and 1 000 000 and preferably between 8000 and 500 000.

I/

The polymer backbone POL may be prepared via a radical, anionic or cationic route, by polyaddition, by polycondensation, by ring opening or by any other (co)polymerization mechanism.

Among the functions that may be (co)polymerized via a radical, anionic or cationic route, mention may be made of activated or unactivated ethylenic double bonds, such as olefinic functions, vinyl, allylic, (meth)acrylic or (meth)acrylamide functions, and combinations thereof.

Among the functions that may be polymerized by polyaddition or by polycondensation, mention may be made of hydroxyl, primary and secondary amine, ester, carboxylic acid and isocyanate functions, which may be activated or unactivated.

Among the functions that may be polymerized by anionic or cationic ring opening, mention may be made of cyclic esters, cyclic amides, cyclic carbonates and cyclic ethers.

Mention may also be made of reactions between halides and tertiary amines.

Among the ethylenically unsaturated monomers that may be used to form the polymer backbone, mention may be made of:
a) (meth)acrylates of formula $CH_2=CHCOOR^4$ or $CH_2=C(CH_3)COOR^4$ in which $R^4$ represents:
- a hydrogen,
- a linear, cyclic or branched C1-C30 alkyl group (especially cycloalkyl or alkylcycloalkyl), into which are optionally inserted one or more heteroatoms chosen from O, N, S and P; it also being possible for said alkyl group to be substituted with one or more substituents chosen from OH, halogens (Cl, Br, I and F), and groups Si ($R_7$)($R_8$), in which $R_7$ and $R_8$, which may be identical or different, represent a C1-C6 alkyl group or a phenyl group;
- a $C_3$ to $C_{20}$ aryl group such as the phenyl group;
- a $C_4$ to $C_{30}$ aralkyl or alkylaryl group ($C_1$ to $C_8$ alkyl group) such as 2-phenylethyl or benzyl;
- a C4-C12 heterocycloalkyl group containing one or more heteroatoms chosen from O, N, P and S, the ring being aromatic or non-aromatic, such as imidazole;
- a C4-C30 alkylheterocycloalkyl group ($C_1$-$C_8$ alkyl) such as furfurylmethyl or tetrahydrofurfurylmethyl;

said aryl and aralkyl groups possibly comprising, intercalated, one or more heteroatoms chosen from O, N, S and P, and/or possibly being substituted with one or more substituents chosen from hydroxyl groups, halogen atoms and linear or branched $C_1$-$C_4$ alkyl groups, which may themselves comprise, intercalated, one or more heteroatoms chosen from O, N, S and P and/or which may be substituted with one or more substituents chosen from hydroxyl groups, halogen atoms (Cl, Br, I and F), and groups Si $(R_7)(R_8)$, in which $R_7$ and $R_8$, which may be identical or different, represent a $C_1$ to $C_6$ alkyl group, or a phenyl group.

Mention may be made especially of methyl and ethyl (meth)acrylates.

b) (meth)acrylamides of formula $CH_2$=$CHCONR^6R^5$ or $CH_2$=$C(CH_3)CONR^6R^5$ in which $R^5$ and $R^6$, which may be identical or different, have the same meanings as for the groups $R^4$ above.

Examples of (meth)acrylamide monomers are (meth)acrylamide, N-ethyl(meth)acrylamide, N-butylacrylamide, N-t-butylacrylamide, N-isopropylacrylamide, N,N-dimethyl (meth)acrylamide, N,N-dibutylacrylamide, N-octylacrylamide, N-dodecylacrylamide, undecylacrylamide and N(2-hydroxypropylmethacrylamide).

c) vinyl monomers of formula: CH2=CH—$R^9$, CH2=CH—CH2-$R^9$ or CH2=C(CH3)-CH2-$R^9$
in which $R^9$ is a group chosen from hydroxyl, halogen (Cl or F), $NH_2$, acetamide (—$NHCOCH_3$) and —$OR_{10}$ in which $R_{10}$ represents a phenyl group or a C1-C12 alkyl group (vinyl ether); —$OCOR_{11}$ (vinyl ester) in which $R_{11}$ represents:
(i) a linear or branched $C_2$ to $C_{12}$ alkyl group,
(ii) a $C_3$ to $C_{12}$ cycloalkyl group such as isobornyl or cyclohexyl,
(iii) a $C_3$-$C_{20}$ aryl group such as phenyl,
(iv) a $C_4$ to $C_{30}$ aralkyl group ($C_1$ to $C_8$ alkyl group) such as 2-phenylethyl or benzyl,
(v) a saturated or unsaturated, aromatic or non-aromatic, 4- to 12-membered heterocycloalkyl group containing one or more heteroatoms chosen from O, N and S, such as furfuryl or tetrahydrofurfuryl,
(vi) a $C_1$ to $C_4$ alkylheterocycloalkyl group, such as furfurylmethyl or tetrahydrofurfurylmethyl;
said alkyl, cycloalkyl, aryl, aralkyl, heterocycloalkyl or alkylheterocycloalkyl groups possibly being substituted with one or more substituents chosen from hydroxyl groups, halogen atoms and linear or branched $C_1$-$C_4$ alkyl groups in which are optionally intercalated one or more heteroatoms chosen from O, N, S and P, said alkyl groups also possibly being substituted with one or more substituents chosen from hydroxyl groups, halogen atoms (Cl, Br, I and F), and groups $Si(R_7)(R_8)$, in which $R_7$ and $R_8$, which may be identical or different, represent a $C_1$ to $C_6$ alkyl group, or a phenyl group.

Examples of vinyl monomers are vinylcyclohexane, styrene, N-vinylpyrrolidone and N-vinylcaprolactam.

Examples of vinyl esters are vinyl acetate, vinyl propionate, vinyl butyrate, vinyl ethylhexanoate, vinyl neononanoate and vinyl neododecanoate.

Among the vinyl ethers are, for example, methyl vinyl ether, ethyl vinyl ether and isobutyl vinyl ether.

d) ethylenically unsaturated monomers comprising at least one carboxylic acid (COOH), phosphonic acid ($PO_3H_2$) or sulfonic acid ($SO_3H$) function, such as those of formula:
$CH_2$=$C(R_{19})$—$(Z1)_{z1}$-$(Z2)_{z2}$—Y in which:
$R_{19}$ is a hydrogen atom or a methyl radical;
Z1 is a divalent group chosen from —COO—, —CONH—, —CONCH$_3$—, —COO— and —O—, preferably $Z_1$ is chosen from —COO— and —CONH—;

$z_1$ is 0 or 1, preferably 1;
Z2 is a linear, branched or cyclic, saturated or unsaturated, optionally aromatic divalent carbon-based radical, of 1 to 30 carbon atoms, which may comprise 1 to 30 heteroatoms chosen from O, N, S and P;
$z_2$ is 0 or 1, preferably 1; and
Y is a group chosen from —COOH, —$SO_3H$, —$OSO_3H$, —$PO(OH)_2$ and —$OPO(OH)_2$. Z2 may especially be:
a C1-C30 alkylene radical such as methylene, ethylene, propylene, n-butylene, isobutylene, tert-butylene, n-hexylene, n-octylene, n-dodecylene, n-octadecylene, n-tetradecylene or n-docosanylene;
a phenylene radical (ortho, meta or para)-$C_6H_4$—, which is optionally substituted, with a $C_1$-$C_{12}$ alkyl radical optionally comprising 1 to 8 heteroatoms chosen from O, N, S and P; or alternatively a benzylene radical —$C_6H_4$—$CH_2$—, which is optionally substituted, with a C1-C12 alkyl radical optionally comprising 1 to 8 heteroatoms chosen from O, N, S and P;
a radical of formula —$CH_2$—$CH(OH)$—, —$CH_2$—$CH_2$—$CH(OH)$—, —$CH_2$—$CH_2$—$CH(NH_2)$—, —$CH_2$—$CH(NH_2)$—, —$CH_2$—$CH_2$—$CH(NHR')$—, —$CH_2$—$CH(NHR')$—, —$CH_2$—$CH_2$—$CH(NR'R'')$—, —$CH_2$—$CH(NR'R'')$—, —$CH_2$—$CH$=$CH$— with R' and R'' representing a linear or branched $C_1$-$C_{18}$ alkyl, especially methyl or ethyl.

Mention may be made especially of acrylic acid, methacrylic acid, crotonic acid, itaconic acid, fumaric acid, maleic acid, diacrylic acid, dimethylfumaric acid, citraconic acid, acrylamidopropanesulfonic acid, 2-acrylamido-2-methylpropanesulfonic acid, styrenesulfonic acid, vinylbenzoic acid, vinylphosphoric acid, vinylsulfonic acid, vinylbenzenesulfonic acid, acrylamidoglycolic acid of formula CH2=CH—CONHCH(OH)COOH, vinylphosphonic acid; 2-carboxyethyl(meth)acrylate, sulfopropyl acrylate or methacrylate ($CH_2$=$C(CH_3)CO_2(CH_2)_3SO_3H$), sulfoethyl acrylate or methacrylate and methyl vinyl sulfone, 2-(methacryloyloxy)ethyl phosphate of formula $CH_2$=$C(CH_3)COOC_2H_4OP(O)(OH)_2$; diallyl maleate of formula $C_3H_5$—$CO_2$—$CH$=$CH$—$CO_2$—$C_2H_5$; and mixtures thereof.

e) ethylenically unsaturated monomers comprising at least one primary, secondary or tertiary amine function, especially those of formula:

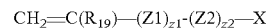

in which:
$R_{19}$, Z1, Z2, $z_1$ and $z_2$ have the same meanings as in the preceding formula; and
either X is a group of formula —N—$R_{17}R_{18}$ with $R_{17}$ and $R_{18}$ representing, independently of each other,
(i) a hydrogen atom;
(ii) a linear, branched or cyclic, saturated or unsaturated, optionally aromatic C1-C30 alkyl group, which may comprise 1-10 heteroatoms chosen from O, N, S and P; especially a methyl, ethyl, propyl, isopropyl, n-butyl, t-butyl, isobutyl, lauryl or stearyl group;
(iii) an alkylene oxide group of formula —$(R_{20}O)_yR_{21}$ with $R_{20}$ representing a linear or branched $C_2$-$C_4$ alkyl, $R_{21}$ is hydrogen or a linear or branched $C_2$-$C_{30}$ alkyl radical and y is between 1 and 250 inclusive;
$R_{17}$ and $R_{18}$ may form, with the nitrogen atom, a saturated or unsaturated, optionally aromatic ring comprising in total 5 to 8 atoms, and especially 4 to 6 carbon atoms and/or 2 to 4 heteroatoms chosen from O, S and N; said ring also possibly being fused with one or more other saturated or unsaturated, optionally aromatic rings, each comprising 5 to 7 atoms, and especially 4 to 7 carbon atoms and/or 2 to 4 heteroatoms chosen from O, S and N;

or X represents a group —R'$_{15}$—N—R'$_{16}$— in which R'$_{15}$ and R'$_{16}$ form, with the nitrogen atom, a saturated or unsaturated, optionally aromatic ring comprising in total 5, 6, 7 or 8 atoms, and especially 4, 5 or 6 carbon atoms and/or 2 to 4 heteroatoms chosen from O, S and N; said ring possibly being fused with one or more other saturated or unsaturated, optionally aromatic rings, each comprising 5, 6 or 7 atoms, and especially 4, 5, 6, 7 or 8 carbon atoms and/or 2 to 4 heteroatoms chosen from O, S and N.

Mention may be made especially of the following monomers: 2-vinylpyridine, 4-vinylpyridine, allylamine and allylpyridine; aminoalkyl(meth)acrylates such as [N,N-di(C$_1$-C$_4$)alkylamino](C$_1$-C$_6$)alkyl(meth)acrylates or [N—(C$_1$-C$_4$)alkylamino](C1-C6)alkyl(meth)acrylates and especially N,N-dimethylaminoethyl(meth)acrylate, N,N-diethylaminoethyl(meth)acrylate, 2-aminoethyl(meth)acrylate, 2-(N-tert-butylamino)ethyl(meth)acrylate; aminoalkyl(meth)acrylamides such as [N,N-di(C$_1$-C$_4$)alkylamino](C$_1$-C$_6$)alkyl(meth)acrylamides or [N—(C$_1$-C$_4$)alkylamino](C$_1$-C$_6$)alkyl(meth)acrylamides, and especially N,N-dimethylaminopropyl(meth)acrylamide, N,N-dimethylaminoethyl(meth)acrylamide, 3-aminopropyl(meth)acrylamide; vinylamine, vinylimidazole, 2-(diethylamino)ethylstyrene; N-vinylimidazole, N-vinyl-2-methylimidazole, N-vinylcarbazole; and also salts thereof and/or quaternized forms thereof.

Polymer backbones that may also be mentioned include polydienes, polyesters, polycarbonates, polyacetals, polyoxyalkylenes, polythioethers, perfluoropolyethers, polyolefins, polyorganosiloxanes, vinyl polymers, poly(meth)acrylics, cellulose derivatives and polysaccharide derivatives, especially ethers and esters.

1/ polydienes, which are preferably hydrogenated, with hydroxyl end groups and polyolefins with hydroxyl end groups, chosen especially from polybutadiene, polyisoprene and poly(1,3-pentadiene)homopolymers and copolymers. They preferably have a number-average molecular mass of less than 7000 and preferably from 1000 to 5000, and have a hydroxyl end-group functionality of from 1.8 to 3 and preferably in the region of 2. These polydienes are preferably used hydrogenated. Mention will be made in particular of the hydroxylated polybutadienes sold by the company Elf Atochem under the brand names Poly BD R-45HT and Poly BD R-20LM, which will preferably be used hydrogenated. Use may also be made of polyolefins, homopolymers or copolymers, with α,ω hydroxyl end groups, such as polyisobutylene oligomers with α,ω hydroxyl end groups and the copolymers sold by the company Mitsubishi under the brand name Polytail, with, in particular, those corresponding to formula:

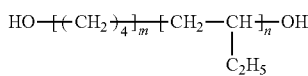

2/ polyesters initially with α,ω-OH end groups, also known as polyester-polyols, especially those obtained by reaction between:

at least one polyhydric alcohol such as ethylene glycol, propylene glycol, diethylene glycol, neopentyl glycol, 1,4-butanediol, furandimethanol, cyclohexanedimethanol, glycerol, trimethylolpropane or pentaerythritol, and mixtures thereof, and at least one carboxylic acid, preferably a dicarboxylic acid, or a derivative, especially an ester, such as succinic acid, glutamic acid or adipic acid and the dimethyl esters thereof; and phthalic anhydride.

They may also be obtained by polymerization of a lactone, for example caprolactone, and of a polyol.

Mention may be made of the polyesterpolyols obtained by condensation with a fatty acid dimer and/or diol dimer. The fatty acid dimers may be of the formula:

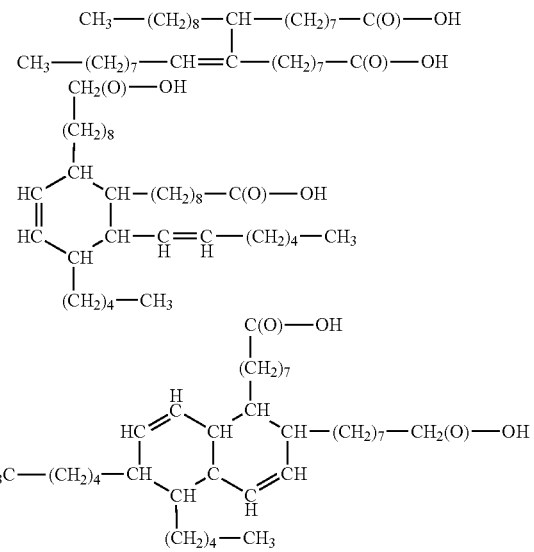

The diol dimers are preferably those defined in the article by R. Höfer, European Coating Journal, March 2000, pages 26-37. They have the same chemical structures as the corresponding fatty acid dimers, only the functionalities change. As indicated in the article by R. Höfer, European Coating Journal, March 2000, pages 26-37, the transformation of the fatty acid dimers into diol dimers may be performed either by hydrogenation of methyl esters of the fatty acid dimers or by direct dimerization of oleyl alcohol.

Mention may also be made of the polyesterpolyols obtained by reaction with natural or synthetic hydrocarbon-based oils bearing two to three hydroxyl groups (or epoxides). The preferred oils may bear two hydroxyl groups per chain, such as the monoglycerides of structure:

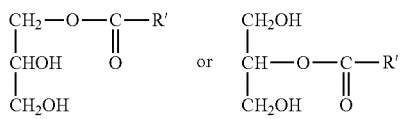

in which R' is a linear or branched alkyl chain, for instance glyceryl monostearate.

3/ polycarbonates initially bearing α, ω-OH end groups, which may be obtained by reaction between a diol, which may be chosen from 1,3-propanediol, 1,4-butanediol, 1,6-hexanediol, diethylene glycol and tetraethylene glycol, and a diaryl carbonate, for instance a diphenyl carbonate, or phosgene.

4/ polyalkylene oxides initially bearing α,ω-OH end groups, which may be obtained by polymerization of cyclic oxides, chosen especially from ethylene oxide, propylene oxide and tetrahydrofuran, or by addition of one or more cyclic oxides to polyfunctional initiators, chosen especially from water, ethylene glycol, diethylene glycol, cyclohexanediethanol, glycerol, trimethylolpropane, pentaerythritol and bisphenol A. The polyoxypropylene diols and triols and the poly(oxyethylene-oxypropylene)diols and triols, obtained via simultaneous or sequential addition of ethylene oxides or of propylene glycols to suitable initiators, are preferred poly-alkylene oxides. Similarly, polytetramethylene glycols obtained by polymerization of tetrahydrofuran and polyalkylene oxide oligomers bearing at least two amine groups at the ends of the POE chain are preferred polyalkylene oxides.

5/ polythioethers initially bearing α,ω-OH end groups, which may be obtained by condensation of thiodiglycol alone or with other glycols, or dicarboxylic acids, formaldehyde, amino alcohols or aminocarboxylic acids.

6/ polyacetals initially bearing α,ω-OH end groups, which may be obtained by reaction between a glycol, especially diethylene glycol, trimethylene glycol and hexanediol, and formaldehyde. Mention may also be made of polyacetals obtained by polymerization of cyclic acetals.

7/ polyorganosiloxanes initially bearing at least two reactive groups such as —OH, —NH$_2$, —NHR, —SH and SiH, among which mention may be made of α,ω-telechelic polyorganosiloxanes bearing OH, NH$_2$ and/or NHR end groups, of structure:

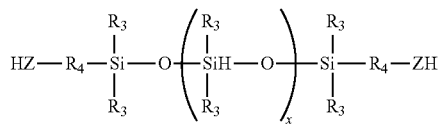

with:
x denotes an integer from 0 to 100,
Z represents —O—, or —NH—, or —NR—,
R is as defined previously,
R$_3$ is a group chosen from linear or branched C1-C40 alkyl or alkoxy (preferably —CH$_3$, —C$_2$H$_5$, n-C$_3$H$_7$ and iso-C$_3$H$_7$), phenyl groups, optionally substituted with 1 to 3 methyl or ethyl groups, polyorganosiloxane chains, linear or branched C$_1$-C$_{12}$ fluoroalkyl groups, and linear or branched C$_1$-C$_{12}$ fluoroalkoxyethylene groups, R$_4$ is chosen from divalent C$_1$-C$_{60}$ alkyl groups, C$_1$-C$_{60}$ oxyalkylene groups containing from 0 to 3 ethylene oxide units, and mixtures thereof, and in which each atom directly linked to a hydroxyl group is a carbon atom.

Preferably, R$_4$ is a divalent C$_1$-C$_{10}$ alkylene radical in which x is an integer such that the number-average molecular mass of the polysiloxane ranges from 300 to 10 000.

Very preferably, the polydimethylsiloxanes have the structure:

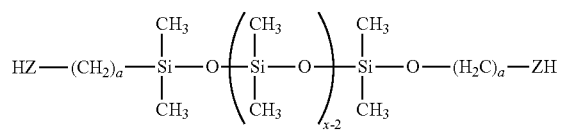

in which a denotes an integer ranging from 1 to 10, and Z is as defined above.

Mention may also be made of polyorganosiloxanes for which R$_4$ is an oxyalkylene group comprising butylene oxide units, or propylene oxide units, or from 0 to 3 ethylene oxide units, especially those of structure:

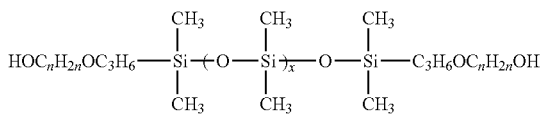

in which n ranges from 2 to 6 independently, and x is an integer from 2 to 100.

Mention may also be made of polyorganosiloxanes bearing polyalkylene oxide grafts ending with —OH groups (PEO grafts or PEO-PPO grafts), especially of structure:

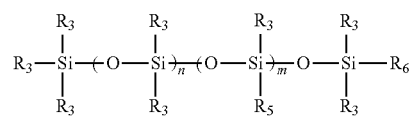

in which R$_5$ is a monovalent polyalkylene oxide group with an —OH end group, and R$_6$ being identical to R$_3$ or to R$_5$.

Mention may also be made of polyorganosiloxanes bearing amine side and/or end groups, especially of structure:

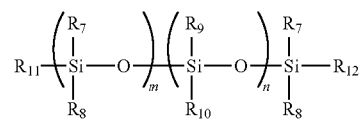

in which:
the groups R$_7$ and R$_9$, which may be identical or different, are chosen from C1-C22 alkyl, phenyl, naphthyl and polyoxyalkylene groups,
at least one of the groups represented by the symbols R$_{10}$ and R$_{12}$ is a group of structure H$_2$N—(—R$_{13}$—NH—)$_s$—R$_{14}$, in which R$_{12}$ and R$_{14}$ each represent an alkylene group comprising from 1 to 6 carbon atoms and s is 0 or 1,
the other groups may be identical or different, and are C1-C22 alkyl groups, or phenyl, naphthyl or polyoxyalkylene groups, and
m and n each represent a number at least equal to 1.

Mention may also be made of polyorganosiloxanes bearing thiol —SH side and/or end groups.

Mention may also be made of polyorganosiloxanes bearing hydrogenosilane side and/or end groups, of structure:

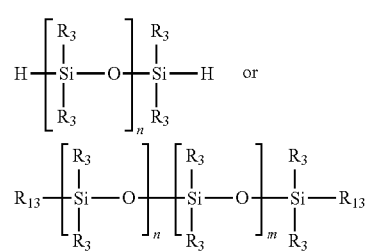

in which R$_{13}$ represents either R$_3$ or H.

Such polyorganosiloxanes can only be used for attaching junction groups (A) bearing a (meth)allylic double bond.

8/ perfluoropolyethers initially bearing hydroxyl end and/or side groups, preferably the perfluoro polyether diols of formula:

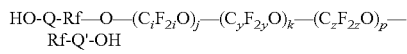

in which:
the oxyperfluoroalkylene groups —(C$_i$F$_{2i}$O)—, (C$_y$F$_{2y}$O)— and —(C$_z$F$_{2z}$O)— are randomly distributed, or are grouped in blocks in a chain,
i, y and z are integers from 1 to 10, j and p are integers from 0 to 100, and k is an integer from 1 to 100,
each group Rf is independently chosen from divalent perfluoroalkyl radicals comprising from 1 to 20 carbon atoms,
each group Q is independently chosen from —C$_6$H$_4$, —C$_6$H$_3$Cl—, C$_2$H$_4$OCH$_2$— and C$_b$H$_{2b}$,
each group Q' is independently chosen from —C$_6$H$_4$, —C$_6$H$_3$Cl—, C$_2$H$_4$OCH$_2$— and C$_b$H$_{2b}$, and
b is an integer from 1 to 20.

9/ vinyl or (meth)acrylic oligomers or polymers initially bearing —OH, —NH$_2$, —NHR or —SH reactive groups.

These are preferably oligomers with a number-average molecular weight of less than 10 000, obtained by copolymerization of one or more vinyl, allylic, olefin, vinyl ether or (meth)acrylic acid or ester or amide monomers, with at least one co-reagent monomer bearing at least one group chosen from —OH, —NH$_2$ and —NHR. Mention may be made of homopolymers and copolymers obtained by polymerization of hydroxyalkyl(meth)acrylates, such as 2-hydroxyethyl acrylate, or vinyl alcohol (obtained by hydrolysis of the vinyl acetate units of the polymer), or allyl alcohol, vinylamine or allylamine. It is also possible to use (homo- and co-) oligomers bearing α,ω-OH reactive end groups. The polymerization of methacrylic (acid, ester or amide) monomers in the presence of the transfer agent 2-mercaptoethanol (HS—CH$_2$—CH$_2$—OH) leads to oligomers functionalized at each α,ω end with a hydroxyethyl sulfide group:

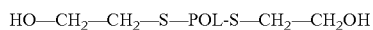

where POL denotes:

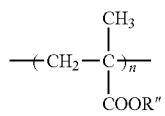

and R" represents a group chosen from alkyl, aryl, aralkyl, alkenyl, alkoxy, alkoxy-alkyl, alkoxyaryl and phenyl groups.

10/ cellulose (or polysaccharide) derivatives, such as cellulose (or guar) ethers, hydroxyalkyl ethers and alkyl ethers, and cellulose esters (such as acetates, propionates, butyrates and mixed esters), and nitrocellulose.

11/ di-, tri-, tetra- and more generally polysaccharides or derivatives thereof, especially ethers and esters.

12/ hyperbranched polymers or dendrimers, initially bearing reactive end groups such as —OH, —NH$_2$, —NHR and —SH. These are molecular structures constructed about a central unit that is generally polyvalent. About this central unit are linked, in concentric layers and in a fully determined structure, branched chain-extending units, thus giving rise to monodispersed symmetrical macromolecules having a well-defined chemical and stereochemical structure. Dendrimers of polyamidoamine type are sold, for example, under the name Starburst® by the company Dendritech. The hyperbranched polymers are polycondensates, generally of polyester, polyamide or polyethyleneamine type, obtained from multifunctional monomers, which have an arborescent structure similar to that of dendrimers but are much less regular than dendrimers.

Attachment of the Junction Groups to the Polymer Backbone

The chemical attachment reactions mentioned here are not limiting, but merely given for illustrative purposes.

According to a first embodiment, the junction groups are attached to polymer backbones comprising groups bearing labile hydrogen such as —OH, —NH$_2$, —NHR or —SH, via functionalization of the junction group with an isocyanate. This reaction comprises the following steps:

functionalization of the group A with an isocyanate according to the reaction scheme:

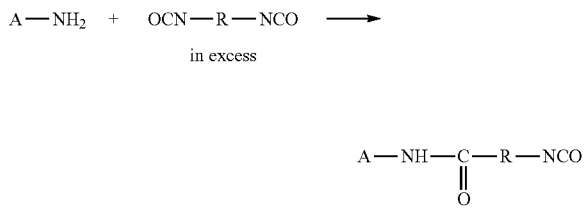

followed by reaction with the polymer backbone comprising at least two groups bearing labile hydrogen such as —OH, —NH$_2$ or —SH.

By way of example, mention may be made of the reaction for attaching a ureidopyrimidone group, for instance 6-methylisocytosine, to a polymer backbone POL of structure HO—POL-OH or H$_2$N—POL-NH$_2$:

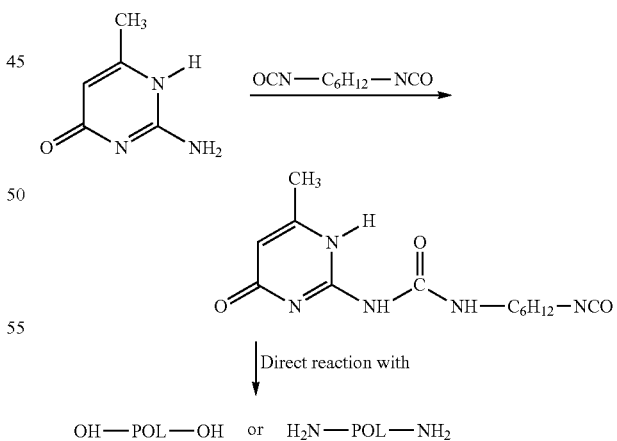

It is also possible to perform the reverse reaction by pre-functionalizing the polymer backbone bearing a labile hydrogen group such as —OH, NH$_2$, —NHR or —SH with a diisocyanate. By way of example, mention may be made of the reaction of a polymer backbone POL with a diisocyanate below:

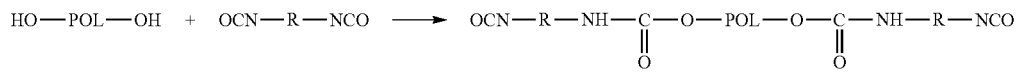

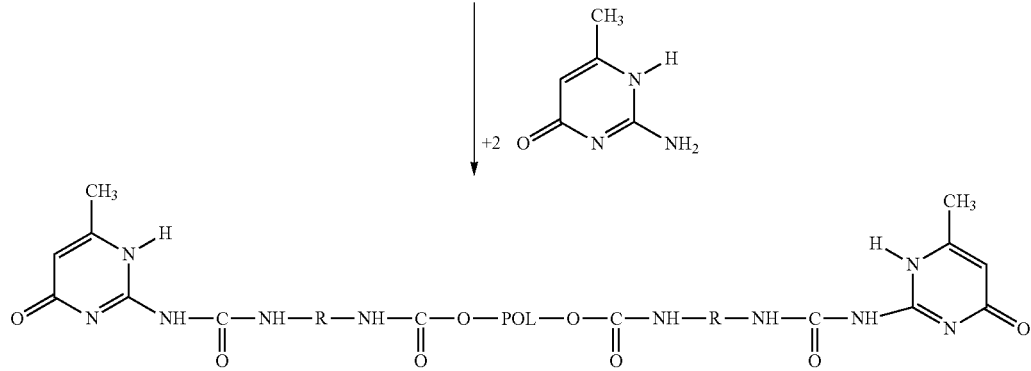

These two reactions are described in the publication Folmer et al., Adv. Mater., 12, 874-878 (2000). This publication also gives the conditions for attaching the ureidopyrimidone groups, for one or other of the two routes described above, to polymer backbones POL of polyoxyalkylene nature (for example: HO-PEO/PPO-OH), polyester (for example polybutyl adipate bearing —OH end groups), polycarbonate (for example copoly(ethylene/butylene) bearing α,ω-OH end groups).

These two routes for attaching ureidopyrimidone groups may be transposed to all the polymer backbones -POL- comprising two or more —OH, —NH, —NHR and —SH groups.

The conditions for attaching the 6-methylisocytosine groups via isophorone diisocyanate to PEO/PPO block copolymers bearing OH end groups are detailed in the publication by Lange, J. Polymer Sci. Part A, Polym. Chem., 37 3657-70 (1999) and also in patent application WO 98/14504.

In one variant, the junction groups may be attached to the polyorganosiloxanes via hydrolyzation. This reaction comprises the following steps: functionalization of the junction group (A) with an allylic group —CH$_2$—CH=CH$_2$ via direct synthesis, which leads to CH$_2$=CH—CH$_2$-(A); followed by reaction with an organosiloxane bearing at least two hydrogenosilane groups —SiH:

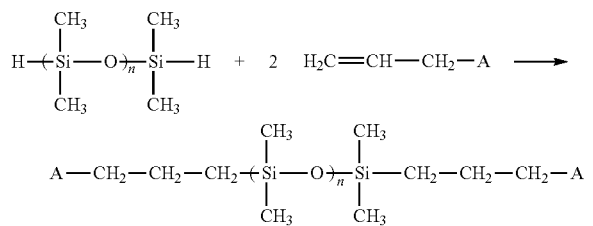

By way of example, mention may be made of the hydrosilylation reaction described in the publication by Sivbesma, Science, 278, 1601-04 (1997).

These protection, hydrosilylation and then deprotection reactions are detailed in the article by Hirschberg, Macromolecules, 32, 2696-2705 (1999) and in patent application WO 98/14504.

II/

Among the polymers obtained by condensation that may be used in the context of the invention, mention may also be made of polymers resulting from the reaction:

- of at least one monomer (a) which comprises at least two identical or different polymerizable groups, chosen from —N=C=O and —N=C=S, or the activated or blocked form thereof;
- of at least one monomer (b) comprising at least two identical or different polymerizable groups bearing labile hydrogen, chosen from —OH, —SH, —NH$_2$ and —NHR, with R representing a $C_1$-$C_6$ alkyl group;
- at least one of the monomers (a) and/or (b) comprising at least one junction group, which is capable of forming at least 3H bonds, preferably at least 4H bonds and more preferentially 4H bonds.

The monomer (a) may thus be of formula Y=C=N—$R^a$—N=C=Y' with Y, Y', which may be identical or different, representing O or S; preferably, Y=Y' and better still Y=Y'=O.

When it is in activated or blocked form, the monomer (a) may also be of formula B—C(O)—NH—$R^a$—NH—C(O)—B' as is described in "Comprehensive Polymer Science", vol. 5: step polymerization p. 421, Pergamon Press (1989). Thus, B and B' may be chosen, independently of each other, from:

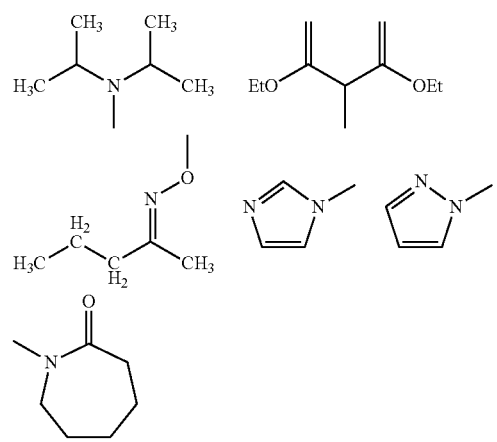

A first preferred family (a1) of monomers (a) is that in which $R^a$ is a saturated or unsaturated, linear or branched, cyclic or non-cyclic, aromatic or non-aromatic divalent radical comprising from 1 to 40 carbon atoms, optionally comprising one or more heteroatoms chosen from O, S and/or N, and/or optionally substituted with one or more fluorine atoms and/or hydroxyl radicals, and mixtures thereof.

The radical $R^a$ may especially be a linear or branched $C_1$-$C_{30}$ alkyl group or a $C_4$-$C_{12}$ cycloalkyl group or a $C_4$-$C_{12}$ aryl group; optionally substituted with an ester and/or amide function.

It may, for example, have the structure:
—$(CH_2)_c$—, —$(CRH)_c$ and —$(CRR')_c$ in which R and R', which may be identical or different, represent a linear or branched $C_1$-$C_{30}$ alkyl group and c is an integer from 1 to 20 and preferably from 1 to 12,
or alternatively of structure:

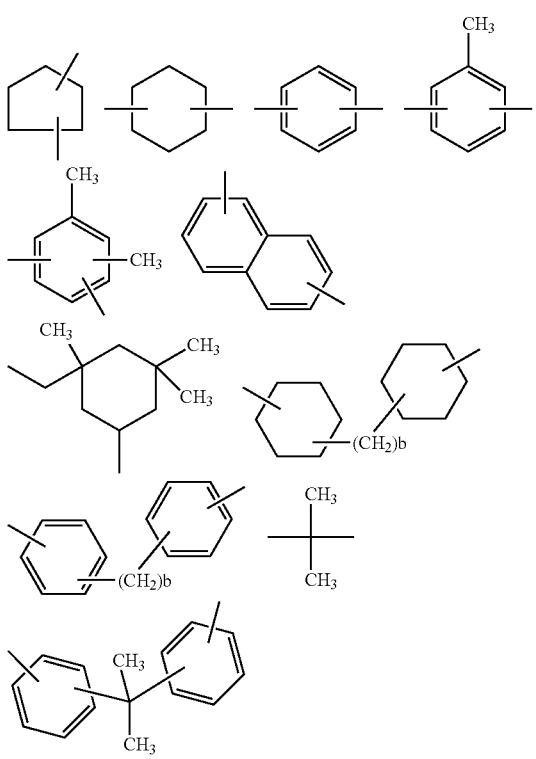

in which b is an integer between 0 and 3 (when b=0, the 2 rings are linked together via a covalent bond);
and also all the combinations of these structures.

Among the divalent radicals $R^a$ that are particularly preferred, mention may be made of the following radicals: 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene); 4,4'-methylenebis(cyclohexyl); 1,4-cyclohexylene; 2,4-tolylene, 2,6-tolylene; 1,5-naphthylene; 4,4'-methylenebis(phenyl); tetramethylxylylene; the divalent radical derived from isophorone.

The monomers (a) that are particularly preferred may be chosen from the following compounds:
1,4-diisocyanatobutane,
1,6-hexamethylene diisocyanate or 1,6-diisocyanatohexane,
1,5-diisocyanato-2-methylpentane,
1,4-diisocyanato-4-methylpentane,
1,6-diisocyanato-2,2,4-trimethylhexane,
1,6-diisocyanato-2,4,4-trimethylhexane,
1,5-diisocyanato-5-methylhexane,
3(4)-isocyanatomethyl-1-methylcyclohexyl isocyanate,
1,6-diisocyanato-6-methylheptane,
1,5-diisocyanato-2,2,5-trimethylhexane,
1,7-diisocyanato-3,7-dimethyloctane,
1-isocyanato-1,2,2-trimethyl-3-(2-isocyanatoethyl)cyclopentane,
1-isocyanato-n-butyl-3-(4-isocyanatobut-1-yl)cyclopentane,
1-isocyanato-1,2-dimethyl-3-ethyl-3-isocyanatomethylcyclopentane,
1-isocyanato-1-methyl-4-(4-isocyanatobut-2-yl)cyclohexane,
1-isocyanato-1,4-dimethyl-4-isocyanatomethylcyclohexane,
1-isocyanato-1,3-dimethyl-3-isocyanatomethylcyclohexane,
1,3-bis(isocyanatomethyl)cyclohexane,
isophorone diisocyanate,
4,4'-methylenebis(cyclohexyl isocyanate),
1,4-diphenylene diisocyanate, tolylene 2,4-diisocyanate, tolylene 2,6-diisocyanate,
1,3-bis(isocyanatomethyl)benzene,
4,4'-methylenebis(phenyl isocyanate),
naphthalene diisocyanate,
tetramethyl-1,3-xylylene diisocyanate.

Needless to say, these diisocyanates may be used alone or in the form of a mixture of two or more diisocyanates.

A second preferred family (a2) of monomers (a) is that in which the divalent radical $R^a$ is a polymeric radical, especially of homopolymer or copolymer type, for instance chosen from:

ethylenic copolymers such as polyolefins comprising units chosen from 1,2-butadiene; 1,4-butadiene; isoprene; ethylene; propylene; 1,2-butylene, 1,4-butylene; isobutylene; (meth)acrylic copolymers, (meth)acrylamide copolymers, vinyl copolymers, allylic copolymers, and mixtures thereof.

Thus, vinyl/(meth)acrylate, vinyl/(meth)acrylamide, vinyl/(meth)acrylate/methacrylamide, olefinic/vinyl and (meth)acrylate/(meth)acrylamide copolymers are suitable for use in the invention.

perfluoro or non-perfluoro polyethers, of polyethylene oxide or polypropylene oxide type, and polyethylene oxide/polypropylene oxide copolymers thereof, polytetramethylene oxides and perfluoropolyethers; polythioethers;

polyesters, and especially polyesters based on adipic acid or terephthalic acid; polycaprolactone; poly(2-methyl-1,3-propylene adipate), poly(2-methyl-1,3-propylene) glutarate; sulfonic polyesters;

polylactides;

polyamides;

polyoxazolines such as poly(2-methyloxazoline) or poly(2-ethyloxazoline);

siloxane copolymers, for instance polysiloxanes consisting of units —Si($R^4$)($R^5$)O— in which ($R^4$) and ($R^5$), which may be identical or different, represent H or a linear or branched, cyclic or non-cyclic, saturated or unsaturated, or aromatic, carbon-based radical, preferably a $C_1$-$C_{12}$ alkyl which may possibly comprise one or more and preferably 1 to 5 identical or different heteroatoms, chosen from: O, N, S, P, F and Si, preferably O, N and S, and especially polydimethylsiloxanes (PDMS), and poly(methylphenylsiloxanes);

copolymers of these various types of polymer, for instance polysiloxane/polyethylene oxide copolymers, polyacetals;

perfluoro or non-perfluoro polycarbonates;

and mixtures thereof.

When $R^a$ is a polymeric radical, it preferably has a weight-average molar mass (Mw) of between 500 and 30 000, more particularly between 700 and 25 000 and better still from 800 to 15 000.

Preferably, $R^a$ may be chosen from functional polymers of the following type:
- polyesters, more particularly based on adipic acid and/or terephthalic acid; poly(2-methyl-1,3-propylene adipate) and poly(2-methyl-1,3-propylene)glutarate;
- polyethers and especially polytetramethylene oxides, siloxane copolymers; and
- poly(ethylene-butylenes) and polybutadienes.

When $R^a$ corresponds to a mixture of different polymers, the percentage of said different polymers may be chosen by a person skilled in the art as a function of the desired properties.

Preferably, the monomers (a) are of the type (a1), alone or as a mixture with each other. However, it is also possible to have a mixture of monomers (a1), alone or as a mixture, and of monomers (a2), alone or as a mixture.

When the monomer (a) comprises at least one junction group, it may be of formula:

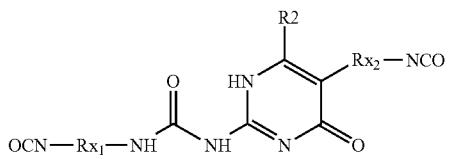

in which $Rx_1$ and $Rx_2$, which may be identical or different, represent a divalent carbon-based radical chosen from a linear or branched $C_1$-$C_{30}$ alkyl group or a $C_4$-$C_{12}$ cycloalkyl group or a $C_4$-$C_{12}$ aryl group; optionally comprising 1 to 8 heteroatoms chosen from O, N, S, F, Si and P; optionally substituted with an ester or amide function, or with a $C_1$-$C_{12}$ alkyl radical; or a mixture of these groups; R2 being as defined previously for the junction group (A).

Preferably, the monomer (a) may be of formula:

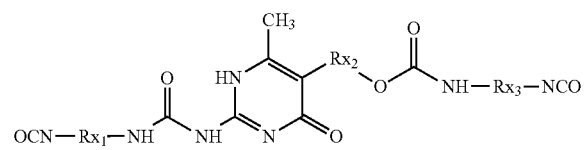

in which $Rx_1$, $Rx_2$ and $Rx_3$, which may be identical or different, represent a divalent carbon-based radical chosen from a linear or branched $C_1$-$C_{30}$ alkyl group, a $C_4$-$C_{12}$ cycloalkyl group and a $C_4$-$C_{12}$ aryl group; or a mixture thereof.

The radicals Rx1, Rx2 and Rx3, independently of each other, may preferentially be chosen from the following radicals: methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-biphenylenemethylene; 1,2-tolylene, 1,4-tolylene, 2,4-tolylene, 2,6-tolylene; 1,5-naphthylene; 4,4'-methylenebis(phenyl); tetramethylxylylene; the divalent radical derived from isophorone.

In a particularly preferred manner, $Rx_1$, $Rx_2$ and $Rx_3$ represent, independently of each other, —$(CH_2)_2$—, —$(CH_2)_6$—, —$CH_2CH(CH_3)CH_2C(CH_3)(CH_3)CH_2CH_2$—, or an -isophorone- radical; and better still $Rx_1$ and $Rx_3$ represent an -isophorone- radical and $Rx_2$ represents —$(CH_2)_2$—, which gives the monomer (a) below:

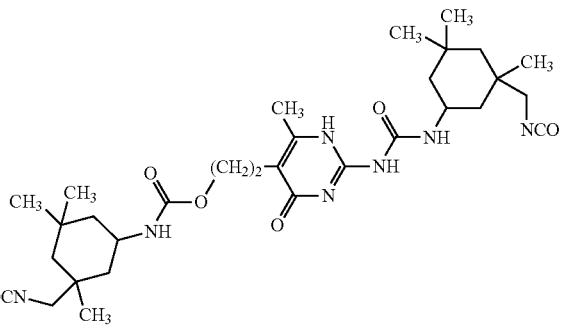

The polymer according to the invention also comprises at least one monomer (b) chosen from the monomers (b1) and (b2) defined below; it may obviously comprise a mixture of monomers (b1) and (b2); these monomers both comprise at least two identical or different polymerizable groups, chosen from OH, SH, $NH_2$ and NHR with R=C1-C6 alkyl.

The monomer (b1) may be of formula HX—$R^{b1}$—X'H, with X and X', which may be identical or different, chosen from O, S, NH and NR, R representing a $C_1$-$C_6$ alkyl group. Preferably, in (b1), X and/or X'=O and preferentially X=X'=O.

The divalent radical preferably represents a divalent polymeric radical, especially of homopolymer or copolymer type, chosen, for example, from dithiol, diamine, diol and amino alcohol functional copolymers, the alcohol, amine and/or thiol functions being borne at the ends of the chain or along the backbone; polymeric radicals that may especially be mentioned include radicals of the type such as:
- perfluoro or non-perfluoro polyethers, of polyethylene oxide or polypropylene oxide type, and polyethylene oxide/polypropylene oxide copolymers thereof, polytetramethylene oxides; perfluoropolyethers and polythioethers;
- polylactides;
- polyesters, especially based on adipic acid or terephthalic acid; in particular polycaprolactone; poly(2-methyl-1,3-propylene adipate), poly(2-methyl-1,3-propylene) glutarate; sulfonic polyesters;
- polyamides;
- polyoxazolines such as poly(2-methyloxazoline) or poly (2-ethyloxazoline);
- siloxane copolymers, for instance polysiloxanes consisting of units —Si($R^4$)($R^5$)O— in which ($R^4$) and ($R^5$), which may be identical or different, represent H or a linear or branched, cyclic or non-cyclic, saturated or unsaturated, or aromatic, carbon-based radical, preferably a $C_1$-$C_{12}$ alkyl which may optionally comprise one or more and preferably 1 to 5 identical or different heteroatoms, chosen from: O, N, S, P, F and Si, preferably O, N and S, and especially polydimethylsiloxanes (PDMS), and poly(methylphenylsiloxanes);
- polyacetals;
- ethylenic copolymers and especially (meth)acrylic copolymers, (meth)acrylamide copolymers, vinyl copolymers and allylic copolymers; thus, vinyl/(meth)acrylate, vinyl/(meth)acrylamide, vinyl/(meth)acrylate/methacrylamide, olefinic/vinyl and (meth)acrylate/(meth) acrylamide copolymers are suitable for use in the invention;

polyolefins comprising units chosen from 1,2-butadiene; 1,4-butadiene; isoprene; ethylene; propylene; 1,2-butylene, 1,4-butylene; isobutylene;

perfluoro or non-perfluoro polycarbonates;

copolymers of these various types of polymer, for instance polysiloxane/polyethylene oxide copolymers, and mixtures thereof.

The monomer (b1) preferably has a weight-average molar mass (Mw) of between 500 and 30 000, more particularly between 700 and 25 000 and better still from 800 to 15 000.

When $R^{b1}$ corresponds to a mixture of different polymers, the percentage of said different polymers may be chosen by a person skilled in the art as a function of the desired properties.

Preferably, $R^{b1}$ may be chosen from functional polymers of the type such as:

polyesters, more particularly based on adipic acid and/or terephthalic acid; and especially poly(2-methyl-1,3-propylene adipate) and poly(2-methyl-1,3-propylene) glutarate;

polyethers and especially polytetramethylene oxides, siloxane copolymers; and poly(ethylene-butylenes) and polybutadienes.

The monomer (b2) may thus be of formula HX—$R^{b2}$—X'H, with X and X', which may be identical or different, chosen from O, S, NH and NR, R representing a $C_1$-$C_6$ alkyl group. Preferably, in (b2), X and/or X'=O and preferentially X=X'=O. The divalent radical $R^{b2}$ preferably represents a branched or non-branched, cyclic or non-cyclic, saturated or unsaturated, aromatic or non-aromatic divalent carbon-based radical containing from 1 to 40 carbon atoms, optionally comprising one or more heteroatoms chosen from O, S, P and N, and/or optionally substituted with one or more fluorine and/or silicon atoms.

When they are present, the heteroatom(s) may be intercalated in the chain of said radical, or alternatively said radical may be substituted with one or more groups comprising them such as hydroxyl or amino groups ($NH_2$, NHR' or NR'R" with R' and R", which may be identical or different, representing a linear or branched $C_1$-$C_{22}$ alkyl, optionally comprising 1 to 12 heteroatoms chosen from O, N, S, F, Si and P, especially methyl or ethyl).

Thus, $R^{b2}$ may comprise:

an alkylene radical containing 1 to 40 carbon atoms or a cycloalkylene radical containing 3 to 16 carbon atoms, which is optionally substituted, with a $C_1$-$C_{12}$ alkyl radical optionally comprising 1 to 8 heteroatoms chosen from O, N, S, F, Si and P, such as methylene, ethylene, propylene, n-butylene, isobutylene, tert-butylene, n-hexylene, n-octylene, n-dodecylene, n-octadecylene, n-tetradecylene, n-docosanylene; ethyl-2-hexylene, cyclohexylene, cyclohexylmethylene, isophorone;

a $C_1$ to $C_{30}$ arylene radical such as an (ortho, meta or para)-$C_6H_4$-phenylene radical, optionally substituted with a $C_1$-$C_{12}$ alkyl radical optionally comprising 1 to 25 heteroatoms chosen from O, N, S, F, Si and P;

a benzylene radical —$C_6H_4$—$CH_2$— optionally substituted with a $C_1$-$C_{12}$ alkyl radical optionally comprising 1 to 8 heteroatoms chosen from O, N, S, F, Si and P;

a C1 to C30 and preferably $C_2$ to $C_{12}$ alkylarylene or arylalkylene radical, a radical of formula: —O—CO—O—, —CO—O—, —OCO—, —O—CO—NH—, anhydride, —NH—CO—NH—, NHCO;

a radical —Si($R^4$)($R^5$)O— in which $R^4$ and $R^5$, which may be identical or different, represent H or a linear or branched, cyclic or non-cyclic, saturated or unsaturated, or aromatic, hydrocarbon-based radical, preferably a $C_1$-$C_{12}$ alkyl which may optionally comprise one or more and preferably 1 to 5 identical or different heteroatoms chosen from O, N, S, P, F and Si, and preferably O, N and S;

an oxyalkylene or aminoalkylene radical, especially an alkylene oxide radical of formula —($R'''O$)$_y R^{iv}$ with R''' representing a linear or branched $C_2$-$C_4$ alkyl, $R^{iv}$ is hydrogen or a linear or branched $C_1$ to $C_{30}$ alkyl radical and y is between 1 and 500 inclusive and preferably from 1 to 250;

a mixture of these radicals.

In particular, $R^{b2}$ may be:

an alkylene radical containing 1 to 40 carbon atoms or a cycloalkylene radical containing 3 to 16 carbon atoms, which is optionally substituted, with a $C_1$-$C_{12}$ alkyl radical optionally comprising 1 to 8 heteroatoms chosen from O, N, S, F, Si and P, such as methylene, ethylene, propylene, n-butylene, n-pentylene, isobutylene, tert-butylene, n-hexylene, n-octylene, n-dodecylene, n-octadecylene, n-tetradecylene, n-docosanylene; ethyl-2-hexylene, cyclohexylene, cyclohexylmethylene, isophorone;

a $C_1$-$C_{30}$ arylene radical such as an (ortho, meta or para)-$C_6H_4$-phenylene radical, optionally substituted with a $C_1$-$C_{12}$ alkyl radical optionally comprising 1 to 25 heteroatoms chosen from O, N, S, F, Si and P;

a $C_1$ to $C_{30}$ and preferably $C_2$ to $C_{12}$ alkylarylene or arylalkylene radical, and especially a benzylene radical —$C_6H_4$—$CH_2$— optionally substituted with a $C_1$-$C_{12}$ alkyl radical optionally comprising 1 to 8 heteroatoms chosen from O, N, S, F, Si and P;

an oxyalkylene or aminoalkylene radical, especially an alkylene oxide radical of formula —($R'''O$)$_y R^{iv}$ with R''' representing a linear or branched $C_2$-$C_4$ alkyl, $R^{iv}$ is hydrogen or a linear or branched $C_1$ to $C_{30}$ alkyl radical and y is between 1 and 500 inclusive and preferably from 1 to 250;

a mixture of these radicals.

Preferably, $R^{b2}$ may be:

an alkylene radical containing 1 to 12 carbon atoms or a cycloalkylene radical containing 3 to 6 carbon atoms, which is optionally substituted, with a $C_1$-$C_{12}$ alkyl radical such as methylene, ethylene, propylene, n-butylene, isobutylene, tert-butylene, n-pentylene, n-hexylene, n-octylene, n-dodecylene, n-octadecylene, cyclohexylene, cyclohexylmethylene, isophorone;

a $C_1$ to $C_{30}$ and preferably $C_2$ to $C_{12}$ alkylarylene or arylalkylene radical, optionally substituted with a $C_1$-$C_{12}$ alkyl radical, for instance a benzylene —$C_6H_4$—$CH_2$— or benzylenedimethylene radical.

The monomer (b2) preferably has a weight-average molar mass (Mw) of between 60 and 1000, more particularly between 70 and 700 and better still from 80 to 500.

Among the monomers (b2) that are particularly preferred, mention may be made of:

aminoethanol, aminopropanol; 4-aminobutanol; 1-ethylaminobutan-2-ol; amino-2-methyl-2-propanol; methyl-4-amino-4-pentan-2-ol;

1,2-ethylenediamine; 1,2-propylenediamine; 1,3-propylenediamine; 1,4-diaminobutane; 1,5-diaminopentane; 1,6-diaminohexane; 2,6-toluenediamine;

1,4-butanediol; 1,6-hexanediol; 1,2-ethanediol; 1,2-propanediol; 1,3-propanediol;

neopentyl glycol; di(ethylene glycol) of formula HO—($CH_2CH_2O$)$_2$H; dihydroxylated poly(ethylene oxides); dihydroxylated poly(propylene oxides); dihydroxylated poly(ethylene oxide/propylene oxide) copolymers;

1,2-benzenedimethanol, 1,4-benzenedimethanol; 1,4-dimethylolcyclohexane;
1,2-benzenethiol;
mixtures thereof.

When the monomer (b2) comprises at least one junction group, it may be of formula:

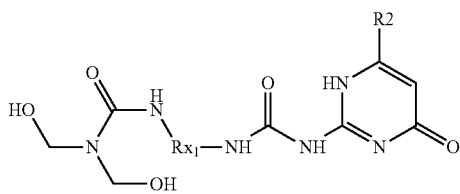

in which $R^2$ and Rx1 are as defined previously.

In one particular embodiment, the monomer (b2) may bear an ionizable group. Among the anionizable monomers (b2), mention may be made of monomers comprising carboxylic (—COOH) and/or sulfonic (—SO$_3$H) functions, especially those of formula:

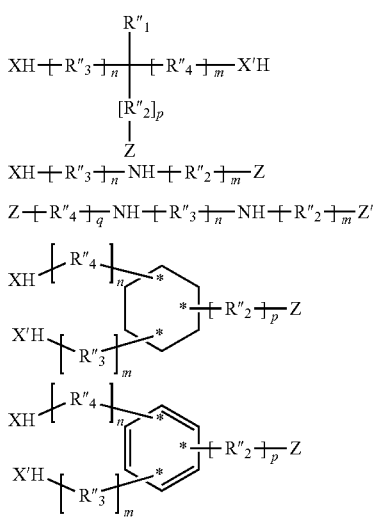

in which:
R"$_1$ represents H or a branched or unbranched, cyclic or non-cyclic, saturated or unsaturated, aromatic or non-aromatic alkyl group containing from 1 to 40 carbon atoms, and/or optionally comprising one or more heteroatoms chosen from O, S, P and N, and/or optionally substituted with one or more fluorine or silicon atoms; the heteroatom(s), when they are present, may be intercalated in the chain of said group, or alternatively said group may be substituted with one or more groups comprising them, such as hydroxyl or amino groups (NH$_2$, NHR' or NR'R" with R' and R", which may be identical or different, representing a linear or branched C$_1$-C$_{22}$ alkyl, especially methyl or ethyl);

R"$_2$, R"$_3$ and R"$_4$, which may be identical or different, represent a branched or unbranched, cyclic or non-cyclic, saturated or unsaturated, aromatic or non-aromatic alkylene group (divalent alkyl) containing from 1 to 40 carbon atoms, and/or optionally comprising one or more heteroatoms chosen from O, S, P and N, and/or optionally substituted with one or more fluorine or silicon atoms; the heteroatom(s), when they are present, may be intercalated in the chain of said group, or alternatively said group may be substituted with one or more groups comprising them, such as ester, amide, hydroxyl or amino groups (NH$_2$, NHR' or NR'R" with R' and R", which may be identical or different, representing a linear or branched C$_1$-C$_{22}$ alkyl, especially methyl or ethyl);

X and X', which may be identical or different, represent O, S, NH or NR in which R is a linear or branched C$_1$-C$_6$ alkyl radical; preferably X and X' represent O;

Z and Z', which may be identical or different, represent a carboxylic acid (—COOH) or sulfonic acid (—SO$_3$H) function.

n, p, m and q are, independently of each other, equal to 0 or 1.

Preferably, the anionizable monomers (b2) are chosen from the compounds of formula:

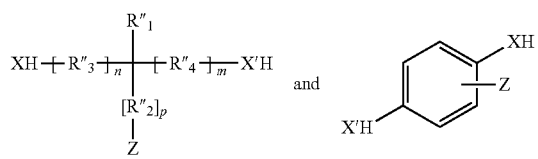

in which X, X', R"1, R"2, R"3, R"4, m, n, p and Z are as defined above, and more particularly the compounds of formula:

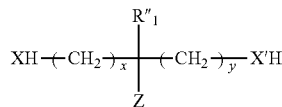

for which R"1 represents an alkyl group containing from 1 to 22 carbon atoms, and preferably CH$_3$, and x and y, which may be identical or different, are between 1 and 5 inclusive.

Among the preferred anionizable monomers (b2), mention may be made of dimethylolpropionic acid, dimethylaminopropionic acid, N-ethylsulfonicdimethanolamine, N-ethylsulfonicdiethanolamine and diolbenzenesulfonic acid. It is clear that these anionic groups may be neutralized.

Among the cationizable or amphoteric monomers (b2), mention may be made most particularly of the monomers bearing tertiary amine functions of formula:

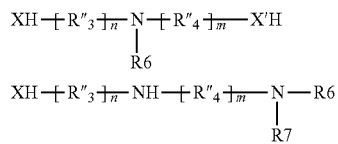

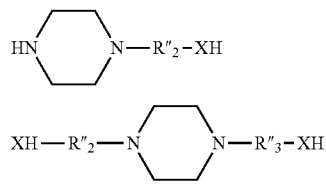

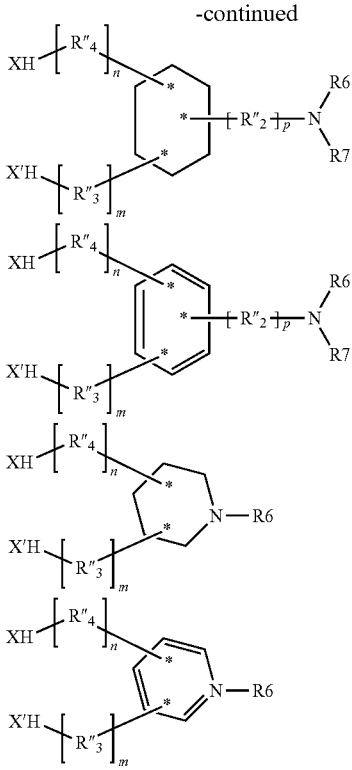

in which:
- R″$_2$, R″$_3$ and R″$_4$, which may be identical or different, represent a branched or unbranched, cyclic or non-cyclic, saturated or unsaturated, aromatic or non-aromatic alkylene group (divalent alkyl) containing from 1 to 40 carbon atoms, and/or optionally comprising one or more heteroatoms chosen from O, S, P and N, and/or optionally substituted with one or more fluorine or silicon atoms; the heteroatom(s), when they are present, may be intercalated in the chain of said group, or alternatively said group may be substituted with one or more groups comprising them, such as ester, amide, hydroxyl or amino groups (NH$_2$, NHR' or NR'R″ with R' and R″, which may be identical or different, representing a linear or branched C$_1$-C$_{22}$ alkyl, especially methyl or ethyl);
- X and X', which may be identical or different, represent O, S, NH or NR in which R is a linear or branched C$_1$-C$_6$ alkyl radical; preferably X and X' represent O;
- n, p and m are, independently of each other, equal to 0 or 1;
- R$_6$ and R$_7$ represent a linear or branched C$_1$ to C$_{22}$ alkyl group, preferably methyl, ethyl, lauryl or behenyl.

Mention may be made especially of the monomers of formula:

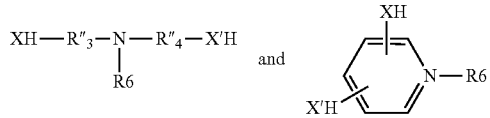

in which X, X', R″3, R″4 and R6 are as defined previously.

Mention may be made especially of N-methyldiethanolamine, N-tert-butyldiethanolamine, N-ethyldiethanolamine and diaminopyridine. It is clear that these cationic groups may be neutralized.

As cationic or amphoteric monomers (b2), mention may also be made of those in which the amine function is in a quaternary form, of formula:

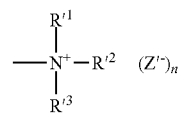

as defined above.

The quaternization of the tertiary amine groups may be performed with compounds bearing labile halogen, especially alkyl halides such as C$_1$-C$_{12}$ alkyl chlorides or bromides, for example methyl bromide or ethyl chloride. These groups may also be quaternized with compounds bearing labile halogen comprising carboxylic or sulfonic acid functions, especially sodium chloroacetate; or with cyclic sulfones, for example propane sulfone. Amphoteric monomers (or betaines, containing at least one (+) charge and at least one (−) charge borne by the same monomer) are thus obtained. The quaternization may be performed on the already-synthesized polymer or on the starting monomers, before polymerization.

The polymer according to the invention may optionally comprise monomers (c) of structure YCN—R$_{10}$ with Y representing O or S; preferably O; and R$_{10}$ representing a linear or branched, cyclic or non-cyclic, saturated or unsaturated, aromatic or non-aromatic carbon-based and especially alkyl radical, containing from 1 to 40 carbon atoms, optionally comprising one or more heteroatoms chosen from O, S, P and N, and/or optionally substituted with one or more fluorine or silicon atoms; the heteroatom(s), when they are present, may be intercalated in the chain of said radical, or alternatively said radical may be substituted with one or more groups comprising them such as ester and/or amide groups.

In one particular embodiment, R$_{10}$ may also bear at least one junction group. In particular, YCN—R$_{10}$ may correspond to the formula:

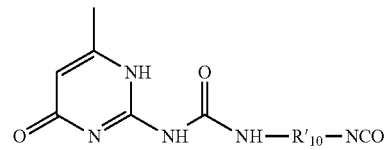

in which R'10 may represent a divalent carbon-based radical chosen from a linear or branched C$_1$-C$_{30}$ alkyl group, a C$_4$-C$_{12}$ cycloalkyl group or a C$_4$-C$_{12}$ aryl group; optionally but not preferentially comprising 1 to 8 heteroatoms chosen from O, N, S, F, Si and P; and also the mixtures of these meanings.

The polymer according to the invention may also optionally comprise monomers (d) of structure HX—R$_{11}$ with:
- X representing O, S, NH or NR, R representing a C$_1$-C$_6$ alkyl group; preferably, X=O; and
- R$_{11}$ representing a linear or branched, cyclic or non-cyclic, saturated or unsaturated, aromatic or non-aromatic carbon-based and especially alkyl radical, containing from 1 to 40 carbon atoms, optionally comprising one or more heteroatoms chosen from O, S, P and N, and/or optionally substituted with one or more fluorine or silicon atoms; the heteroatom(s), when they are present, may be intercalated in the chain of said radical, or alternatively said radical may be substituted with one or more groups comprising them such as ester and/or amide groups.

These polymers are characterized by the presence of polyurethane and/or polyurea and/or polythiourethane and/or polythiourea blocks preferably corresponding to the following general formula: $—[X—R^b—X'—C(Y)NH—R^a—NHC(Y')—]_x—$ in which X and X' are derived from the monomers (b), Y and Y' are derived from the monomers (a), the radicals $R^b$ are derived from the monomers (b), i.e. they represent, statistically, Rb1 and Rb2 as defined above; the radicals $R^a$ are derived from the monomers (a), and are as defined above; in particular, they may represent, statistically, monomers $R^a$ of divalent aliphatic radical type (a1)) and monomers $R^a$ of polymeric type (a2); it being understood that at least one of the radicals Ra and/or Rb comprises at least one junction group A capable of forming at least 3H bonds; x is an integer ≥2.

Preferably, the monomers of the type $HX—R^{b1}—X'H$ (polymer) represent 10% to 95% by weight, especially 12% to 85% by weight and preferentially 15% to 80% by weight relative to the total weight of the final polymer.

Preferably, the monomers of the type $HX—R^{b2}—X'H$ (small diol) represent 1% to 30% by weight, especially 2% to 25% by weight and preferentially 3% to 20% by weight relative to the total weight of the final polymer.

These (thio)urethane/(thio)urea polymers may be prepared according to standard polycondensation methods known to those skilled in the art. These methods are especially described in the following publications:

60 Years of PUR—J. E. Kresta, E. W. Eldred Ed. Technomic Publishing, 1998,

Waterborne and Solvent Based Surface Coating Resins and Their Application, Surface Coating Technology series, Vol. 3, Polyurethanes, Paul Thomas, John Wiley and Sons, 1998.

These polymers are especially described in patent application EP 1 797 868.

III/

The polymer that may be used in the context of the invention may also be a polyalkene-based polymer. This means a polymer derived from the reaction, especially the condensation, of at least one polyalkene polymer functionalized with at least one reactive group, with at least one junction group functionalized with at least one reactive group capable of reacting with the reactive group(s) of the functionalized polyalkene polymer, said junction group being capable of forming at least 3H (hydrogen) bonds and preferably at least 4H bonds, preferentially 4H bonds. Preferably, the functionalized polyalkene polymer, capable of forming all or part of the polymer backbone of the polymer according to the invention, is of formula $HX—P—X'H$ in which:

XH and X'H are reactive groups, with X and X', which may be identical or different, chosen from O, SH, NH and $NR_a$, $R_a$ representing a $C_1$-$C_6$ alkyl group; preferably, X and/or X' denote O; preferentially X and X' denote O;

P represents a homopolymer or a copolymer that may be obtained by polymerization of one or more linear, cyclic and/or branched, monounsaturated or polyunsaturated $C_2$-$C_{10}$ and preferably $C_2$-$C_4$ alkenes; P preferably representing a polyethylene, a polybutylene, a polybutadiene, a polyisoprene, a poly(1,3-pentadiene) or a polyisobutylene, and copolymers thereof, and especially a poly(ethylene/butylene).

Poly(ethylene/butylenes) are copolymers of 1-butene and of ethylene. They may be represented schematically by the following sequence of units:

$[—CH_2—CH_2—]$ and $[—CH_2CH(CH_2—CH_3)—]$

The polybutadienes may be 1,4-polybutadienes or 1,2-polybutadienes, which may be represented schematically, respectively, by the following sequences of units:

$[—CH_2—CH\!=\!CH—CH_2—]$ (1,4-polybutadienes)

$[—CH_2—CH(CH\!=\!CH_2)—]$ (1,2-polybutadienes)

Preferably, they are 1,2-polybutadienes.

Polyisoprenes may be represented schematically by the following sequences of units:

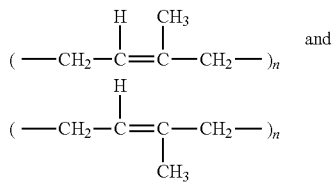

A mixture of above units may obviously also be used, so as to form copolymers. Preferably, the functionalized polyalkene polymers have a number-average molecular mass (Mn) of greater than or equal to 1000, especially between 1000 and 5000, or even between 1500 and 3500.

The functionalized polyalkene polymers may be totally hydrogenated to avoid the risks of crosslinking.

The supramolecular polymers may also comprise in their structure other units derived from other monomers. Comonomers that may be mentioned in particular include styrene and epoxy. In one preferred embodiment, they do not comprise any, and are thus formed only from polyalkene polymers (100%) to form the polymer backbone.

The polyalkene polymers are functionalized with at least one reactive group and preferably with at least two reactive groups. The functionalization preferably occurs at the chain ends. They are then referred to as telechelic polymers. The functionalization groups, or reactive groups, may be attached to the polyalkene polymer via linkers, preferably linear or branched $C_1$-$C_4$ alkylene groups, or directly via a single bond. Reactive groups that may be mentioned include OH, $NH_2$, NHR, SH and NCO functions.

Among the preferred functionalized polyalkene polymers, mention may be made of polydienes, which are preferably hydrogenated, containing hydroxyl functions, preferably hydroxyl end groups, and polyolefins containing hydroxyl end groups. The polydienes containing hydroxyl end groups are especially defined, for example, in FR 2 782 723. They may be chosen from polybutadiene, polyisoprene and poly(1,3-pentadiene) homopolymers and copolymers. They preferably have a number-average molecular mass (Mn) of less than 7000 and preferably between 1000 and 5000, and have a hydroxyl end-group functionality of from 1.8 to 3 and preferably in the region of 2. Mention will be made in particular of the hydroxylated polybutadienes sold by the company Elf Atochem under the brand names Poly BD R-45HT and Poly BD R-20 LM, which will preferably be used hydrogenated; and also hydrogenated dihydroxylated (1,2-polybutadienes), such as GI3000 of Mn=3100, GI2000 (Mn=2100) and GI1000 (Mn=1500) sold by the company Nisso. Among the polyolefins with hydroxyl end groups, mention may be made preferentially of polyolefins, homopolymers or copolymers with α,ω-hydroxyl end groups, such as polyisobutylenes with α,ω-hydroxyl end groups; and the copolymers of formula:

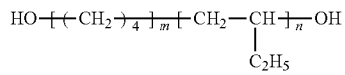

especially those sold by Mitsubishi under the brand name Polytail.

The supramolecular polymers according to the invention also have in their structure at least one residue of a junction group capable of forming at least three H bonds and preferably at least four H bonds, said junction group being initially functionalized with at least one reactive group.

The reactive groups may be attached to the junction group via linkers, preferably linear or branched $C_1$-$C_4$ alkylene groups, or directly via a single bond.

Said reactive groups must be capable of reacting with the reactive group(s) borne by the functionalized polyalkene. Reactive groups that may be mentioned include carboxyl, hydroxyl, amino and isocyanate groups. Preferably, it is a group —N═C═O or —N═C═S, and even more preferentially a group —N═C═O (isocyanate).

Preferably, the linker is a group chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebis(cyclohexylene); tolylene; 2-methyl-1,3-phenylene; 4-methyl-1,3-phenylene; 4,4-biphenylenemethylene;
and preferably: -isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebis(cyclohexylene); 2-methyl-1,3-phenylene.

The term "isophorone" means the following group:

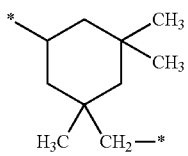

Better still, as junction groups capable of forming at least 3H bonds, mention may be made of groups derived from ureidopyrimidones, and in particular from 2-ureidopyrimidone or 6-methyl-2-ureidopyrimidone.

Unless otherwise mentioned, the term "junction group" means in the present description the group without its reactive function.

The functionalized junction groups capable of reacting with the functionalized polyalkene polymer are preferably of formula:

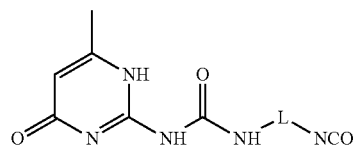

in which L is a single bond or a saturated or unsaturated, or even aromatic, C1-C20, linear, cyclic and/or branched divalent (alkylene) carbon-based group, optionally comprising 1 to 4 heteroatoms N and/or O, especially in the form of a substituent NO$_2$, and especially a group chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebis(cyclohexylene); tolylene; 2-methyl-1,3-phenylene; 4-methyl-1,3-phenylene; 4,4-biphenylenemethylene; and preferably: -isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebis(cyclohexylene); 2-methyl-1,3-phenylene.

In a preferred embodiment, the polymer according to the invention corresponds to the formula:

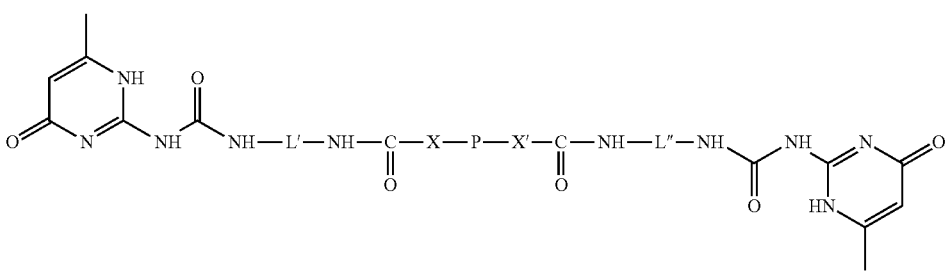

in which:
L' and L" have, independently of each other, the meaning given above for L;
X, X' and P have the meanings given above for the functionalized polyalkene polymer.

Preferably, X═X'═O.

Preferably, L' and L" represent a saturated or unsaturated, C1-C20, linear, cyclic and/or branched divalent (alkylene) carbon-based group; and especially an isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebis(cyclohexylene); 2-methyl-1,3-phenylene group.

Preferably, P represents a polyethylene, a polybutylene, a polybutadiene, a polyisoprene, a poly(1,3-pentadiene), a polyisobutylene, or a copolymer thereof, especially a poly(ethylene-butylene).

This polymer may be prepared via the processes usually used by a person skilled in the art, especially for forming a urethane bond between the free OH functions of a polyalkene, and the isocyanate functions borne by the junction group.

By way of illustration, a first general preparation process consists in:
  optionally ensuring that the polymer to be functionalized does not comprise any residual water,
  heating said polymer comprising at least one reactive function and especially 2 reactive functions, in particular OH, to a temperature that may be between 60° C. and 140° C.; the hydroxyl number of the polymer possibly serving as a reference in order to measure the degree of progress of the reaction;
  adding, preferably directly, the junction group bearing the reactive functions, especially isocyanate;
  optionally stirring the mixture, under a controlled atmosphere, at a temperature of about 90° C.-130° C.; for 1 to 24 hours;
  optionally monitoring by infrared spectroscopy the disappearance of the characteristic isocyanate band (between 2500 and 2800 cm$^{-1}$) so as to stop the reaction on total disappearance of the peak, and then allowing the final product to cool to room temperature.

The reaction may also be monitored by assaying the hydroxyl functions; it is also possible to add ethanol in order to ensure the total disappearance of the residual isocyanate functions.

The reaction may be performed in the presence of a solvent, especially methyltetrahydrofuran, tetrahydrofuran, toluene, propylene carbonate or butyl acetate. It is also possible to add a conventional catalyst for forming a urethane bond. An example that may be mentioned is dibutyltin dilaurate. The polymer may finally be washed and dried, or even purified, according to the general knowledge of a person skilled in the art.

According to the second mode of preparation, the reaction may comprise the following steps:
(i) functionalization of the polymer, which has preferably been dried beforehand, with a diisocyanate according to the reaction scheme:

OH-polymer-OH (1 eq.)+NCO—X—NCO (1 eq.)→
OCN—X—NH—(O)CO-polymer-OC(O)—
NH—X—NCO

The diisocyanate may optionally be in excess relative to the polymer. This first step may be performed in the presence of solvent, at a temperature of between 20° C. and 100° C. This first step may be followed by a period of stirring under a controlled atmosphere for 1 to 24 hours. The mixture may optionally be heated. The degree of progress of this first step may be monitored by assaying the hydroxyl functions.
and then
(ii) reaction of the prepolymer obtained above with 6-methylisocytosine of formula:

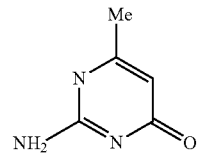

this second step may optionally be performed in the presence of a cosolvent such as toluene, butyl acetate or propylene carbonate. The reaction mixture may be heated to between 80° C. and 140° C. for a time ranging between 1 and 24 hours.

The presence of a catalyst, especially dibutyltin dilaurate, may promote the production of the desired final product.

The reaction may be monitored by infrared spectroscopy, by monitoring the disappearance of the characteristic peak of isocyanate between 2200 and 2300 cm$^{-1}$. At the end of the reaction, ethanol may be added to the reaction medium in order to neutralize any residual isocyanate functions. The reaction mixture may be optionally filtered. The polymer may also be stripped directly in a cosmetic solvent. Such polymers are described in particular in patent application EP 2 189 151.

Definition of the Junction Groups

According to the present invention, a junction group is a chemical group, especially a carbon-based group, which is capable of forming at least three H bonds, preferably at least 4H bonds, and comprising at least one unit of formula (Ia):

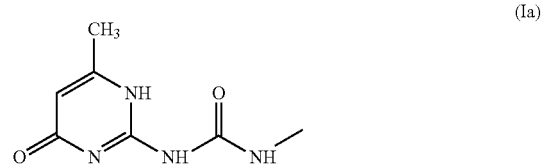

The unit (Ia) is linked to the junction group via a linker (bonding agent) which may be a single covalent bond or a linear, branched or cyclic, saturated or unsaturated, optionally aromatic, C1-C60 divalent carbon-based (especially alkyl) radical, which may contain one or more heteroatoms.

In particular, the linker may be a C$_4$-C$_{12}$ cycloalkyl group; a linear or branched C$_1$-C$_{30}$ alkyl group or a C$_4$-C$_{12}$ aryl group; optionally substituted with an amino, ester and/or hydroxyl function.

Preferably, the linker is a group chosen from: —C$_4$H$_9$-phenyl; 1,4-nitrophenyl, 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebis(cyclohexylene); tolylene; 2-methyl-1,3-phenylene; 4-methyl-1,3-phenylene; 4,4-biphenylenemethylene; and preferably: -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebis(cyclohexylene), 2-methyl-1,3-phenylene.

Preferably, the polymer bearing at least one unit of formula (Ia), or the mixture of such polymers, may be present in the composition (topcoat) in an amount of from 0.1% to 10% by weight and especially 1% to 5% by weight relative to the total weight of the composition. It may also be absent (0%).

Preferably, the cosmetic active agent bearing at least one unit of formula (Ia), or the mixture of such active agents, may be present in the composition in an amount of from 0.01% to 50% by weight and especially 0.01% to 10% by weight relative to the total weight of the composition.

The compositions may moreover comprise a cosmetically acceptable medium, i.e. a medium that is compatible with keratin materials, such as facial or bodily skin, the eyelashes, the eyebrows, the lips and the nails.

They may advantageously comprise a liquid fatty phase, which may constitute a solvent medium for the polymers according to the invention, and which may comprise at least one compound chosen from volatile or nonvolatile carbon-based, hydrocarbon-based, fluoro and/or silicone oils and/or solvents of mineral, animal, plant or synthetic origin, alone or as a mixture, provided that they form a stable, homogeneous mixture and are compatible with the intended use.

For the purposes of the invention, the term 'volatile' means any compound that is capable of evaporating on contact with keratin materials, or the lips, in less than one hour, at room temperature (25° C.) and atmospheric pressure (1 atm). This volatile compound especially has a non-zero vapor pressure, at room temperature and atmospheric pressure, especially ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

In contrast, the term "non-volatile" refers to a compound that remains on keratin materials or the lips at room temperature and atmospheric pressure, for at least one hour, and which especially has a vapor pressure of less than $10^{-3}$ mmHg (0.13 Pa).

Preferably, the cosmetically acceptable medium may comprise, in a liquid fatty phase, at least one oil and/or solvent that may be chosen, alone or as a mixture, from:

1/ esters of monocarboxylic acids with monoalcohols and polyalcohols; advantageously, said ester is a C12-C15 alkyl benzoate or corresponds to the following formula: $R'_1$—COO—$R'_2$ in which:

$R'_1$ represents a linear or branched alkyl radical of 1 to 40 carbon atoms and preferably of 7 to 19 carbon atoms, optionally comprising one or more ethylenic double bonds, optionally substituted, and the hydrocarbon-based chain of which may be interrupted with one or more heteroatoms chosen from N and O and/or one or more carbonyl functions, and $R'_2$ represents a linear or branched alkyl radical of 1 to 40 carbon atoms, preferably of 3 to 30 carbon atoms and better still of 3 to 20 carbon atoms, optionally comprising one or more ethylenic double bonds, optionally substituted, and the hydrocarbon-based chain of which may be interrupted with one or more heteroatoms chosen from N and O and/or one or more carbonyl functions.

The term "optionally substituted" means that $R'_1$ and/or $R'_2$ may bear one or more substituents chosen, for example, from groups comprising one or more heteroatoms chosen from O and/or N, such as amino, amine, alkoxy or hydroxyl.

Examples of groups $R'_1$ are those derived from fatty acids, preferably higher fatty acids chosen from the group formed from acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, oleostearic acid, arachidonic acid and erucic acid, and mixtures thereof.

Preferably $R'_1$ is an unsubstituted branched alkyl group of 4 to 14 carbon atoms and preferably of 8 to 10 carbon atoms and $R_2$ is an unsubstituted branched alkyl group of 5 to 15 carbon atoms and preferably of 9 to 11 carbon atoms.

Mention may be made in particular, preferably, of $C_8$-$C_{48}$ esters, optionally incorporating in their hydrocarbon-based chain one or more heteroatoms from among N and O and/or one or more carbonyl functions; and more particularly purcellin oil (cetostearyl octanoate), isononyl isononanoate, isopropyl myristate, isopropyl palmitate, 2-ethylhexyl palmitate, 2-octyldodecyl stearate, 2-octyldodecyl erucate, isostearyl isostearate, $C_{12}$ to $C_{15}$ alkyl benzoate, hexyl laurate, diisopropyl adipate; and heptanoates, octanoates, decanoates or ricinoleates of alcohols or of polyalcohols, for example of fatty alcohols, for instance propylene glycol dioctanoate, and also isopropyl N-lauroyl sarcosinate (especially Eldew-205SL from Ajinomoto); hydroxylated esters, for instance isostearyl lactate, diisostearyl malate; and pentaerythritol esters; branched C8-C16 esters, especially isohexyl neopentanoate.

2/ hydrocarbon-based plant oils with a high triglyceride content formed from fatty acid esters of glycerol, the fatty acids of which may have varied chain lengths from $C_4$ to $C_{24}$, these chains possibly being linear or branched, and saturated or unsaturated; these oils are especially wheat germ oil, corn oil, sunflower oil, shea oil, castor oil, sweet almond oil, macadamia oil, apricot oil, soybean oil, rapeseed oil, cottonseed oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passionflower oil, musk rose oil, jojoba oil, palm oil or beauty-leaf oil; or alternatively caprylic/capric acid triglycerides, such as those sold by the company Stearinerie Dubois or those sold under the names Miglyol 810®, 812® and 818® by the company Dynamit Nobel.

3/ C6-C32 and in particular $C_{12}$-$C_{26}$ alcohols, and in particular monoalcohols, for instance oleyl alcohol, linoleyl alcohol, linolenyl alcohol, isostearyl alcohol, 2-hexyldecanol, 2-butyloctanol, 2-undecylpentadecanol and octyldodecanol.

4/ linear or branched, volatile or non-volatile hydrocarbon-based oils, of synthetic or mineral origin, which may be chosen from hydrocarbon-based oils containing from 5 to 100 carbon atoms, and in particular petroleum jelly, polydecenes, hydrogenated polyisobutenes such as Parleam, squalane and perhydrosqualene, and mixtures thereof.

Mention may be made more particularly of linear, branched and/or cyclic C5-C48 alkanes, and preferentially branched C8-C16 alkanes, for instance C8-C16 isoalkanes of petroleum origin (also known as isoparaffins); in particular decane, heptane, dodecane and cyclohexane; and also isododecane, isodecane and isohexadecane.

5/ volatile or non-volatile silicone oils.

Volatile silicone oils that may be mentioned include volatile linear or cyclic silicone oils, in particular those with a viscosity of less than 8 centistokes, and in particular containing from 2 to 10 silicon atoms, these silicones optionally comprising alkyl or alkoxy groups containing from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and methylhexyldimethylsiloxane, and mixtures thereof.

The non-volatile silicone oils that may be used according to the invention may be polydimethylsiloxanes (PDMSs), polydimethylsiloxanes comprising alkyl or alkoxy groups, which are pendant and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and 2-phenylethyl trimethylsiloxysilicates.

The liquid fatty phase may also comprise additional oils and/or solvents, which may be chosen, alone or as a mixture, from:
fluoro oils such as perfluoropolyethers, perfluoroalkanes such as perfluorodecalin, perfluoroadamantanes, perfluoroalkyl phosphate monoesters, diesters and triesters, and fluoro ester oils;
oils of animal origin;
$C_6$ to $C_{40}$ and especially C10-C40 ethers; propylene glycol ethers that are liquid at room temperature, such as propylene glycol monomethyl ether, propylene glycol monomethyl ether acetate and dipropylene glycol mono-n-butyl ether;
$C_8$-$C_{32}$ fatty acids, for instance oleic acid, linoleic acid and linolenic acid, and mixtures thereof;
difunctional oils, comprising two functions chosen from ester and/or amide and comprising from 6 to 30 carbon atoms, in particular 8 to 28 carbon atoms and better still 10 to 24 carbon atoms, and 4 heteroatoms chosen from O and N; preferably, the amide and ester functions being in the chain;
ketones that are liquid at room temperature (25° C.), such as methyl ethyl ketone, methyl isobutyl ketone, diisobutyl ketone, isophorone, cyclohexanone and acetone;
aldehydes that are liquid at room temperature, such as benzaldehyde and acetaldehyde.

The liquid fatty phase may represent 1% to 90% by weight of the composition, especially from 5% to 75% by weight, in particular from 10% to 60% by weight, or even from 25% to 55% by weight, relative to the total weight of the composition.

The composition according to the invention may advantageously comprise a thickener which can in particular be chosen from:
silicas, in particular hydrophobic silicas, such as those described in document EP-A-898960, and for example sold under the references Aerosil R812® by the company Degussa, Cab-O-Sil TS-530®, Cab-O-SIL TS-610® and Cab-O-Sil TS-720® by the company Cabot, and Aerosil R972® and Aerosil R974® by the company Degussa;
clays, such as montmorillonite, modified clays such as bentones for example, stearalkonium hectorite, stearalkonium bentonite;
polysaccharide alkyl ethers (in particular of which the alkyl group comprises from 1 to 24 carbon atoms, preferably from 1 to 10, better still from 1 to 6, more especially from 1 to 3), such as those described in document EP-A-898958.

The amount of thickener in the composition according to the invention can range from 0.05% to 40% by weight, relative to the total weight of the composition, preferably from 0.5% to 20% and better still from 1% to 15% by weight.

The composition according to the invention may also comprise at least one wax of plant, animal, mineral or synthetic origin, or even a silicone wax.

Mention may be made in particular, alone or as a mixture, of hydrocarbon-based waxes such as beeswax; carnauba wax, candelilla wax, ouricury wax, Japan wax, cork fiber wax or sugar cane wax; paraffin wax, lignite wax; microcrystalline waxes; lanolin wax; Montan wax; ozokerites; polyethylene waxes; waxes obtained by Fischer-Tropsch synthesis; hydrogenated oils, fatty esters and glycerides that are solid at 25° C. It is also possible to use silicone waxes, among which mention may be made of alkyl or alkoxy polymethylsiloxanes and/or polymethylsiloxane esters.

The amount of wax in the composition according to the invention can range from 0.1% to 70% by weight, relative to the total weight of the composition, preferably from 1% to 40% by weight and better still from 5% to 30% by weight.

The composition according to the invention may also comprise one or more dye-stuffs chosen from pulverulent compounds, for instance pigments, fillers, nacres and glitter flakes, and/or liposoluble or water-soluble dyes.

The dyestuffs, in particular pulverulent dyestuffs, may be present in the composition in a content of from 0.01% to 50% by weight, relative to the weight of the composition, preferably from 0.1% to 40% by weight or even from 1% to 30% by weight.

The term "pigments" should be understood as meaning white or colored, mineral or organic particles of any shape, which are insoluble in the physiological medium, and which are intended to color the composition.

The term "nacres" should be understood as meaning iridescent particles of any shape, in particular produced by certain molluscs in their shell, or else synthesized.

The pigments may be white or colored, mineral and/or organic, and interference or non-interference pigments. Among the mineral pigments that may be mentioned are titanium dioxide, optionally surface-treated, zirconium oxides or cerium oxides, and also iron oxides or chromium oxides, manganese violet, ultramarine blue, chromium hydrate and ferric blue. Among the organic pigments that may be mentioned are carbon black, pigments of D&C type and lakes based on cochineal carmine or on barium, strontium, calcium or aluminum.

The nacreous pigments may be chosen from white nacreous pigments such as mica coated with titanium or with bismuth oxychloride, colored nacreous pigments such as titanium mica with iron oxides, titanium mica in particular with ferric blue or with chromium oxide, titanium mica with an organic pigment of the abovementioned type, and also nacreous pigments based on bismuth oxychloride.

The fillers may be mineral or organic, and lamellar or spherical. Mention may be made of talc, mica, silica, kaolin, Nylon powder and polyethylene powder, poly-β-alanine powder and polyethylene powder, Teflon, lauroyllysine, starch, boron nitride, powders of tetrafluoroethylene polymers, hollow microspheres such as Expancel (Nobel Industrie), Polytrap (Dow Corning), precipitated calcium carbonate, magnesium carbonate, magnesium hydrocarbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The lipsoluble dyes are, for example, Sudan red, DC Red 17, DC Green 6, β-carotene, soybean oil, Sudan brown, DC Yellow 11, DC Violet 2, DC Orange 5 and quinoline yellow. They may represent 0.01% to 20% and better still from 0.1% to 6% of the weight of the composition.

The water-soluble dyes are, for example, beetroot juice or methylene blue, and may represent 0.01% to 6% of the total weight of the composition.

The composition may also comprise other ingredients commonly used in cosmetic compositions. Such ingredients may be chosen from antioxidants, fragrances, essential oils, preserving agents, cosmetic active agents, moisturizers, vitamins, ceramides, sunscreens, surfactants, gelling agents, spreading agents, wetting agents, dispersants, antifoams, neutralizers, stabilizers, polymers and in particular liposoluble film-forming polymers, and mixtures thereof.

Needless to say, those skilled in the art will take care to select this or these optional additional compound(s) and/or the amounts thereof so that the advantageous properties of the composition for the use according to the invention are not, or not substantially, adversely affected by the envisaged addition.

The compositions according to the invention may be in any common acceptable form for a cosmetic composition. They may thus be in the form of a suspension or a dispersion, in particular of oil in water by means of vesicles; an optionally thickened or even gelled organic or oily solution; an oil-in-water, water-in-oil or multiple emulsion; a gel or a mousse; an oily or emulsified gel; a dispersion of vesicles, in particular lipid vesicles; a two-phase or multiphase lotion; a spray; a lotion, a cream, a salve, a soft paste, an ointment, a solid that has been cast or molded in particular as a stick or in a dish, or alternatively a compacted solid.

A person skilled in the art can choose the appropriate pharmaceutical form, and also its method of preparation, on the basis of his general knowledge, taking into account first the nature of the constituents used, in particular their solubility in the support, and secondly the application envisaged for the composition.

The cosmetic compositions according to the invention may be used for caring for and/or making up keratin materials such as the skin, the eyelashes, the eyebrows, the hair, the nails or the lips.

They may thus be in the form of a care and/or makeup product for bodily or facial skin, the lips, the eyelashes, the eyebrows, the hair or the nails; an antisun or self-tanning product; a hair product such as a product for shaping, cleansing, dyeing, protecting, repairing or styling the hair.

The keratin materials are especially bodily or facial skin, the lips, the nails, the hair, the eyebrows and/or the eyelashes.

It is thus possible, according to the invention,
to graft onto the keratin materials, especially the hair, in a first stage, a graftable species bearing a unit (Ia), which may be, for example, a molecule bearing a unit (Ia) linked via a linker (bonding agent) to an isothiouronium function,
and then to deposit, in a second stage, onto said keratin materials an (aqueous-) alcoholic solution comprising a dyeing active agent covalently bonded to a ureidopyrimidone unit (Ia).

This may make it possible to dye the hair. This coloration may advantageously be water-resistant.

It may then be envisaged to move the dyeing active agent, by replacing it with a non-dyeing active agent bearing a unit (Ia) for example, by applying an aqueous solution of said non-dyeing active agent (Ia), by thermal stimulation (60° C.), which would have the effect of making the color disappear; it then being possible for re-coloring using another dyeing active agent bearing a unit (Ia) to be envisaged.

It is also possible to increase the deposition of the active agent, for example to increase the intensity of the color, by depositing onto the keratin materials, for example the hair, a polymer bearing at least two ureidopyrimidone functions (Ia); the polymer may be conveyed in an aqueous-alcoholic solution; the deposition may be performed after the step of grafting with the basecoat, or alternatively the polymer may be in the topcoat, as a mixture with the active agent, for example the dye, bearing a ureidopyrimidone unit (Ia).

The invention thus preferably consists of a cosmetic treatment process which consists in applying to natural or treated hair:
in a first stage, a molecule comprising a unit that can be grafted onto the hair chemically linked to one or more chemical units capable of associating via at least 3 hydrogen bonds with another identical or different unit; i.e. the composition of basecoat type comprising the graftable species bearing a unit (Ia);
in a second stage, one or more cosmetic hair active agents (dye, fatty chain, hydrophilic unit, silicone or UV-screening agent) covalently bonded to a unit capable of associating via at least 3 hydrogen bonds with the units present on the molecule grafted in the preceding step; i.e. the topcoat composition comprising the cosmetic active agent bearing a unit (Ia).

This second step may be repeated as many times as desired, the topcoats possibly being moved and/or exchanged with topcoats comprising other cosmetic active agents, under the action of one or more stimuli that are capable of breaking the hydrogen bonds (thermal, action of a solvent, etc.).

An additional step may be added, either between these two steps, or after the second step, by depositing a solution containing a polymer comprising at least two chemical units capable of associating via at least 3 hydrogen bonds with another identical or different unit (unit Ia).

Another variant consists in applying the cosmetic active agent covalently bonded to a unit (Ia) as a mixture with a polymer bearing a unit (Ia) as defined above; the polymer may thus especially be present in the composition comprising the cosmetic active agent.

The invention also consists of a cosmetic treatment process which consists in applying to keratin materials, especially natural hair or hair treated via a cosmetic treatment, a cosmetic composition comprising as a mixture at least one graftable species comprising at least one unit of formula (Ia), and at least one cosmetic active agent bearing at least one unit of formula (Ia).

In one particular embodiment, the composition also comprises at least one polymer bearing a unit (Ia) as defined above.

The topcoat composition may be moved and replaced as many times as desired, with one or more topcoats bearing other cosmetic active agents, under the action of one or more stimuli that are capable of breaking the hydrogen bonds (thermal, action of a solvent, etc.).

In order to move the cosmetic active agent and to cancel its effect, a topcoat with no cosmetic effect may be used. It will preferably consist of a unit with no cosmetic effect covalently bonded to at least one unit (Ia) capable of associating via at least 3 hydrogen bonds with the unit of the basecoat.

The invention also relates to a kit comprising, firstly, a cosmetic composition comprising at least one graftable species, comprising at least one unit of formula (Ia), and, secondly, a second cosmetic composition comprising at least one cosmetic active agent bearing at least one unit of formula (Ia) as defined previously, optionally as a mixture with a polymer bearing at least one unit (Ia) as defined previously, each composition being packaged in a packaging assembly.

The invention is illustrated in more detail in the following examples.

EXAMPLE 1

Graftable Species A

Preparation of 4-[(4-{[(6-methyl-4-oxo-1,4-dihydro-pyrimidin-2-yl)carbamoyl]amino}butyl)amino]-4-oxobutyl imidothiocarbamate hydrochloride

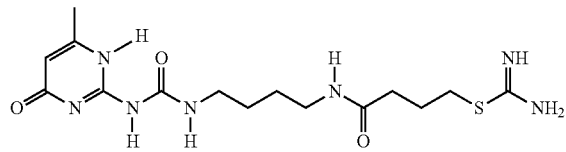 [SMILES: Cc1cc(=O)nc(NC(=O)NCCCCNC(=O)CCCSC(=N)N)[nH]1]

1/ Preparation of tert-butyl [4-({[(6-methyl-4-oxo-1,4-dihydropyrimidin-2-yl)amino]carbonyl}amino)butyl]carbamate (compound 2) from N-(6-methyl-4-oxo-1,4-dihydropyrimidin-2-yl)-1H-imidazole-1-carboxamide (compound 1)

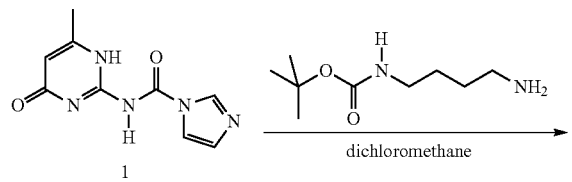

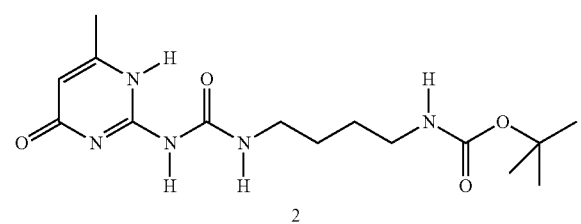

To a solution of 1.72 g of tert-butyl (4-aminobutyl)carbamate (9.1 mmol) in 50 ml of dichloromethane were added 2 g of N-(6-methyl-4-oxo-1,4-dihydropyrimidin-2-yl)-1H-imidazole-1-carboxamide (compound 1) (9.1 mmol) prepared according to the procedure described by E. W. Meijer et al., *J. Am. Chem. Soc.*, 2003, 125, p. 6860. The solution was stirred at reflux for 4 hours. The final product was obtained by precipitation from acetone. After filtering off and washing with acetone, the final product was dried under reduced pressure to give 4.02 g (11.8 mmol) of pure hygroscopic product in the form of a white powder, in a yield of greater than 99% (compound 2).

1H and 13C NMR spectra compliant (DMSO)

2/ Preparation of N-(4-aminobutyl)-N'-(6-methyl-4-oxo-1,4-dihydropyrimidin-2-yl)urea hydrochloride (compound 3) from tert-butyl [4-({[(6-methyl-4-oxo-1,4-dihydropyrimidin-2-yl)amino]carbonyl}amino)butyl]carbamate

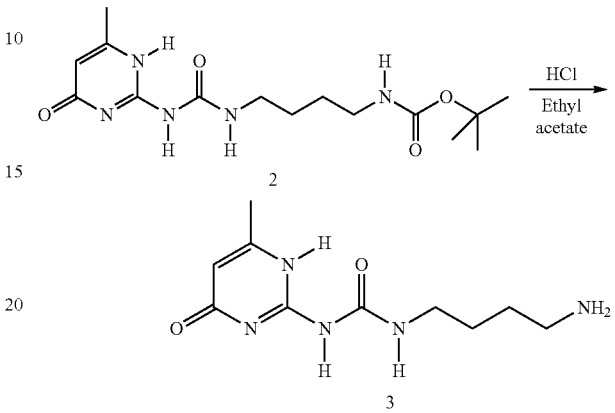

To a solution of 3.02 g of tert-butyl [4-({[(6-methyl-4-oxo-1,4-dihydropyrimidin-2-yl)amino]carbonyl}amino)butyl]carbamate (8.9 mmol) in 10 ml of ethyl acetate were added 9.28 g of 35% hydrochloric acid (89.5 mmol). The solution was stirred at 5° C. for 1 hour. The final product was obtained by precipitation from acetone. After filtering off and washing with acetone, the final product was dried under reduced pressure to give 2.28 g (9.5 mmol) of pure product (compound 3) in the form of a white powder, in a yield of greater than 99% (hygroscopic product). 1H and 13C NMR spectra compliant (DMSO)

3/ Preparation of 4-chloro-N-(4-{[(6-methyl-4-oxo-1,4-dihydropyrimidin-2-yl)carbamoyl]amino}butyl)butanamide (compound 4) from N-(4-aminobutyl)-N'-(6-methyl-4-oxo-1,4-dihydropyrimidin-2-yl)urea hydrochloride

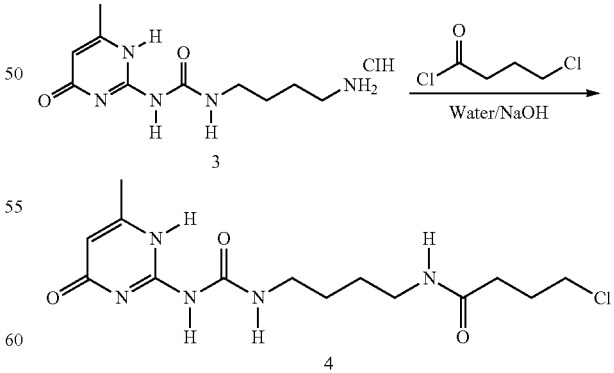

To a solution of 20 g of N-(4-aminobutyl)-N'-(6-methyl-4-oxo-1,4-dihydropyrimidin-2-yl)urea hydrochloride (70 mmol) in 200 ml of water cooled to 0° C. were added alternately 11.6 g of sodium hydroxide (0.29 mol) and 24.4 ml of chlorobutyl chloride (0.22 mol). The solution was stirred for 18 hours at room temperature. The product was obtained by filtration. The final product was dried under reduced pressure to give 14.2 g (41.4 mmol) of pure product (compound 4) in the form of a white powder, in a yield of 54%.

1H and 13C NMR spectra compliant (DMSO)

4/ Preparation of 4-[(4-{[(6-methyl-4-oxo-1,4-dihydropyrimidin-2-yl)carbamoyl]amino}butyl)amino]-4-oxobutyl imidothiocarbamate hydrochloride from 4-chloro-N-(4-{[(6-methyl-4-oxo-1,4-dihydropyrimidin-2-yl)carbamoyl]amino}butyl)butanamide

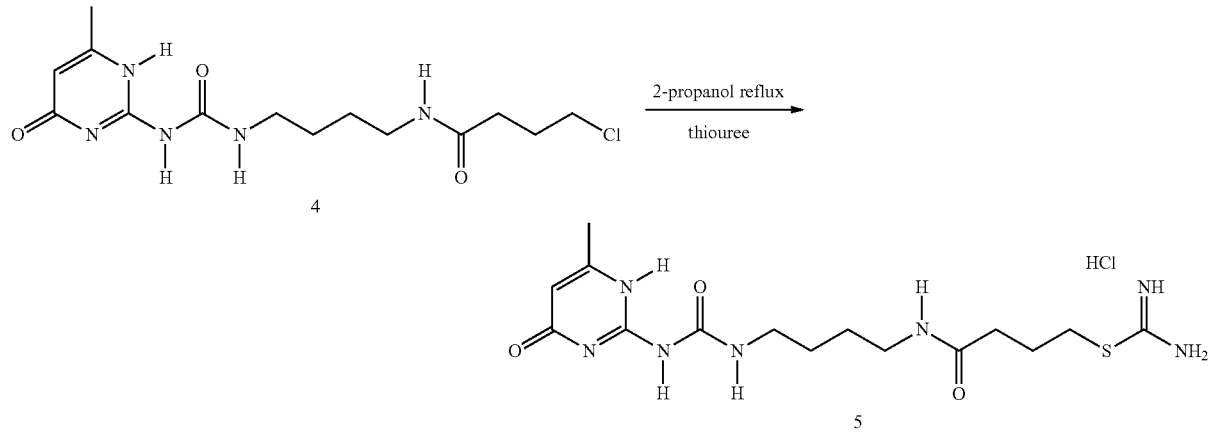

To a solution of 10.7 g of 4-chloro-N-(4-{[(6-methyl-4-oxo-1,4-dihydropyrimidin-2-yl)carbamoyl]amino}butyl)butanamide (3 mmol) in 100 ml of 2-propanol were added 2.84 g of thiourea (4 mmol). The solution was stirred for 17 hours at reflux. The product was obtained by filtration. The final product was dried under reduced pressure to give 10.7 g (25.5 mmol) of pure desired product in the form of a yellow powder, in a yield of 82%.

1H and 13C NMR spectra compliant (DMSO)

EXAMPLE 2

Dye A

The functionalized ureidopyrimidone dye used is a mixture consisting essentially of 2-({4-[bis(2-hydroxyethyl)amino]-2-nitrophenyl}amino)ethyl [6-({[(6-isopropyl-4-oxo-1,4-dihydropyrimidin-2-yl)amino]carbonyl}amino)hexyl]carbamate.

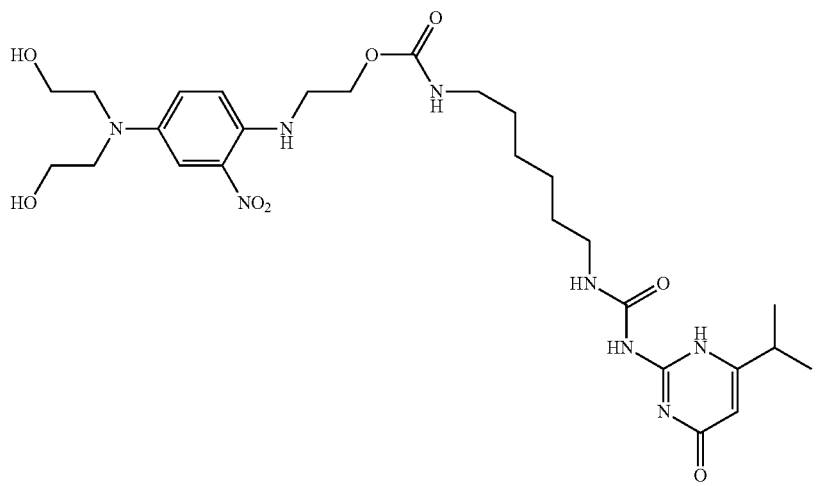 [SMILES: CC(C)c1cc(=O)nc(NC(=O)NCCCCCCNC(=O)OCCNc2ccc(N(CCO)CCO)cc2[N+](=O)[O-])[nH]1]

4 g of 2,2'-[4-(2-hydroxyethylamino)-3-nitrophenylimino] diethanol were dissolved in 75 ml of anhydrous tetrahydrofuran. 4.51 g of N-(5-isocyanatopentyl)-N'-(6-isopropyl-4-oxo-1,4-dihydropyrimidin-2-yl)urea were added portionwise, under an argon atmosphere and with stirring, followed by addition of 3 drops of dibutyltin dilaurate (DBTDL). The reaction medium was then stirred at this temperature for 3 hours; the disappearance of the isocyanate function was monitored by infrared. After total disappearance of the isocyanate function, the reaction medium was filtered through Celite and then concentrated to half its volume. The reaction medium was then poured into 800 ml of ethyl ether with vigorous stirring and the precipitate obtained was filtered off on a sinter funnel. The product was then dried under vacuum to give 7 g of a violet powder, in a yield of about 80%.

Analysis by HPLC coupled to a mass spectrometer shows the predominant formation of the desired product [M+H]+= 607 and also a remaining amount of starting material and of double-reaction product of mass M=928.

15 mg of dye thus prepared are placed in a 25 ml flask, and 100 μl of benzyl alcohol and 400 μl of ethyl alcohol are added. The mixture is heated slightly to 40° C. in order to dissolve the dye (ultrasonication if necessary). Finally, 1000 μl of water are added. An opaque violet solution is obtained.

EXAMPLE 3

Dye B

Preparation of the Dye of Formula:

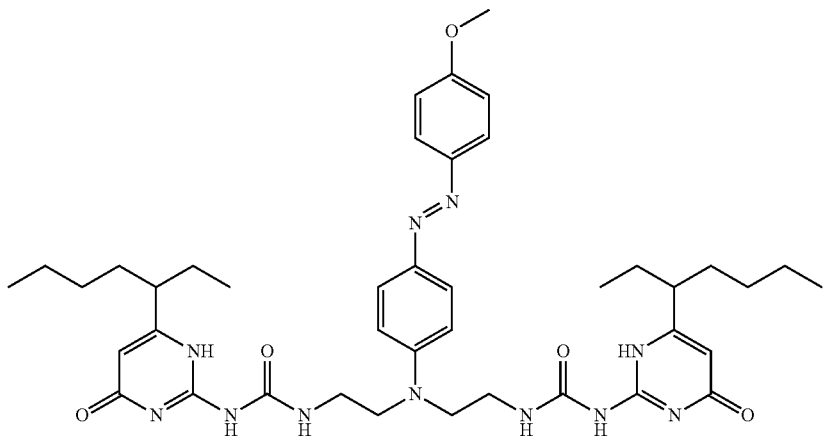 [SMILES: CCCCC(CC)c1cc(=O)nc(NC(=O)NCCN(CCNC(=O)Nc2nc(=O)cc(C(CC)CCCC)[nH]2)c2ccc(/N=N/c3ccc(OC)cc3)cc2)[nH]1]

This dye is prepared according to the procedure described in EP 1 310 533 B1, example 22 (dye 21).

15 mg of this dye were placed in a 25 ml flask, and 100 μl of benzyl alcohol and 500 μl of ethyl alcohol were added. The mixture was then heated slightly to 40° C. in order to dissolve the dye, with ultrasonication to complete the dissolution. 900 μl of water were then added to obtain an opaque orange solution.

EXAMPLE 4

150 mg locks of hair were first moistened with water and then shampooed with 0.2 g of shampoo containing 15% of sodium lauryl sulfate in water, and then rinsed with water.

The test solution was applied to the entire lock placed on a suitable drip tray, for 30 minutes at 60° C. After wringing dry and rinsing with water, the treated lock was observed to see whether or not there was coloration.

The control was a lock of hair which did not undergo the grafting treatment (no treatment with a graftable species).

Test 1 (Control)

1.5 ml of dye solution A at 0.8% (0.025 mol/l) were applied to the locks, for 30 minutes at 60° C.

Observation: very very pale coloration

Test 2 (Control)

1.5 ml of dye solution B at 1% (0.025 mol/l) were applied to the locks, for 30 minutes at 60° C.

Observation: no coloration

Test 3 (Invention)

1.5 ml of a 1% solution of graftable species A (solution of pH 9, adjusted with 32% aqueous ammonia) were applied to a 150 mg lock of hair, for 15 minutes at room temperature (25° C.). The lock was then wrung dry, and 1.5 ml of solution of dye A at 0.8%, as prepared in example 2, were then applied for 15 minutes at 60° C. The lock was then rinsed with tap water for 10 seconds between the fingers, and was then dried between two absorbent towels.

Observation: a slight coloration was thus obtained.

Test 4 (Invention)

1.5 ml of a 1% solution of graftable species A (solution of pH 9, adjusted with 32% aqueous ammonia) were applied to a 150 mg lock of hair, for 15 minutes at 60° C. The lock was then wrung dry, and 1.5 ml of solution of dye A at 0.8%, as prepared in example 2, were then applied for 15 minutes at 60° C. The lock was then wrung dry, washed with water and dried.

Observation: a slight coloration was thus obtained.

Test 5 (Invention)

1.5 ml of a 1% solution of graftable species A (solution of spontaneous pH) were applied to a 150 mg lock of hair, for 15 minutes at 25° C. The lock was then wrung dry, and 1.5 ml of solution of dye A at 0.8%, as prepared in example 2, were then applied for 15 minutes at 60° C. The lock was then wrung dry, washed with water and dried.

Observation: a moderate coloration was thus obtained.

Test 6 (Invention)

1.5 ml of a 5% solution of graftable species A (solution of pH 9, adjusted with 32% aqueous ammonia) were applied to a 150 mg lock of hair, for 15 minutes at 25° C. The lock was then wrung dry, and 1.5 ml of solution of dye A at 0.8%, as prepared in example 2, were then applied for 15 minutes at 60° C. The lock was then wrung dry, washed with water and dried.

Observation: a strong coloration was thus obtained.

Increasing the concentration of graftable species makes it possible to increase the coloration.

EXAMPLE 5

Screening Agent C

Dibutyl 4,4'-[(6-{[4-({[(6-methyl-4-oxo-1,4-dihydro-pyrimidin-2-yl)amino]carbonyl}amino)butyl]amino}-1,3,5-triazine-2,4-diyl)diimino]dibenzoate Preparation of dibutyl 4,4'-[(6-{[4-({[(6-methyl-4-oxo-1,4-dihydropyrimidin-2-yl)amino]carbonyl}amino)butyl]amino}-1,3,5-triazine-2,4-diyl)diimino]dibenzoate 9 from N-(4-aminobutyl)-N'-(6-methyl-4-oxo-1,4-dihydropyrimidin-2-yl)urea hydrochloride 1

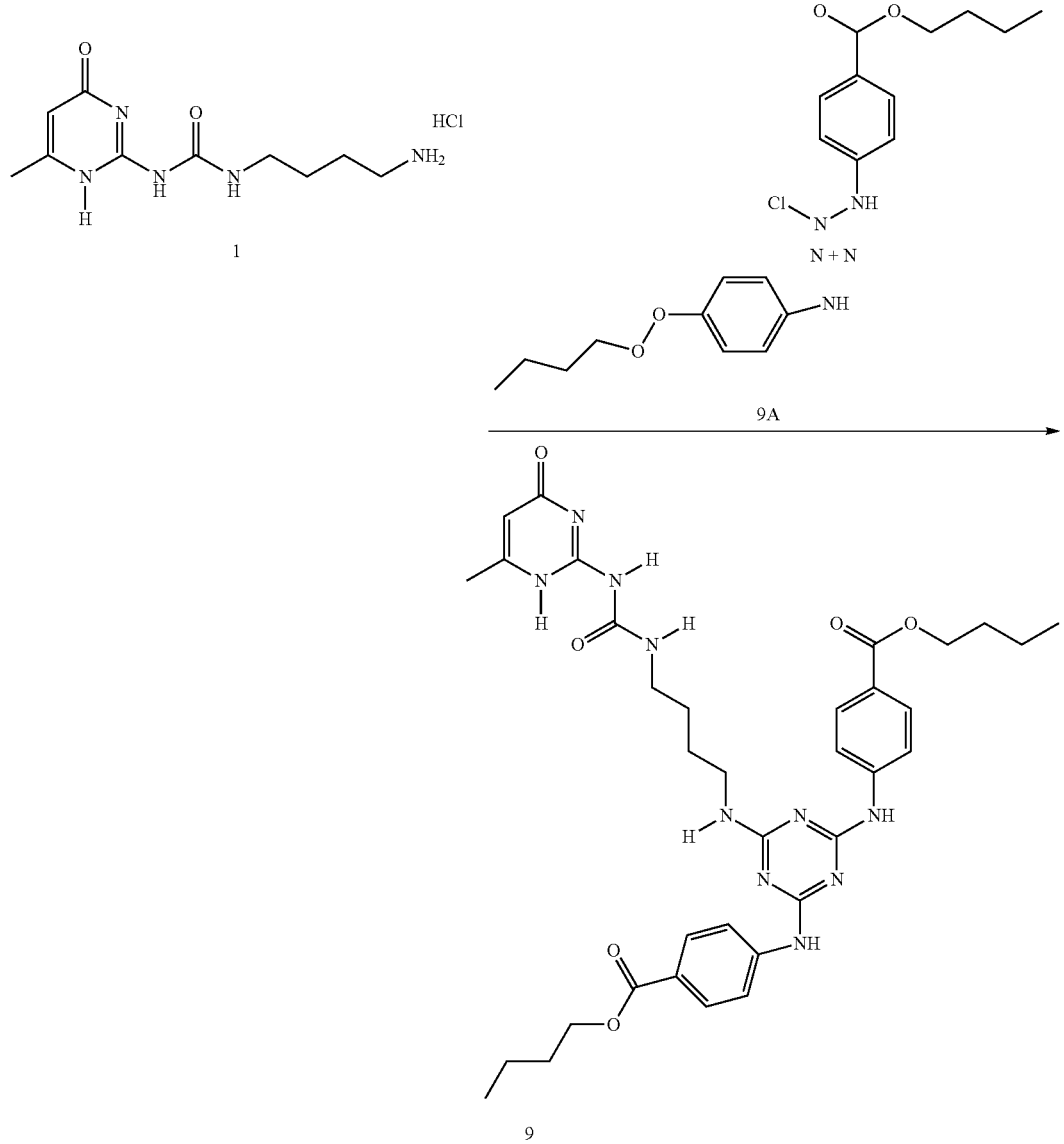

To a suspension of 100 mg of butyl 4-[(4-{[4-(butoxycarbonyl)phenyl]amino}-6-chloro-1,3,5-triazin-2-yl)amino]benzoate 9A (0.2 mmol) in 4 ml of acetonitrile were added 4.8 mg of N-(4-aminobutyl)-N'-(6-methyl-4-oxo-1,4-dihydropyrimidin-2-yl)urea hydrochloride 1 (0.2 mmol) and 66 µl of diisopropylethylamine (0.4 mmol). The solution was stirred for 6 hours at reflux. The final product was obtained by precipitation from water and then dried under reduced pressure to give 0.06 g (0.09 mmol) of pure product 9 in the form of a white powder, in a yield of 40%. $^1$H NMR (DMSO): δ 0.9-0.94 ppm (t, 6H); 1.43-1.72 ppm (m, 12H); 2.38 ppm (s, 3H); 3.17 ppm (t, 2H); 3.40 ppm (t, 2H); 4.38-4.4 ppm (t, 4H); 5.66 ppm (s, 1H); 7.74-7.76 ppm (d, 4H); 7.99-8.01 ppm (d, 4H)

UV (CHCl$_3$) lambda max: 310 nm – ϵ max: 79940, E1%=1140

EXAMPLE 6

An antisun cream having the following composition is prepared:

| Phase A: | |
|---|---|
| Screening agent C of Example 5: | 3% |
| butylmethoxydibenzoylmethane (Parsol 1789) | 2% |
| Bis(ethylhexyloxyphenol)methoxyphenyltriazine (Tinosorb S) | 3% |
| C12-15 Alkyl benzoate | 15% |
| Cetyl alcohol | 0.5% |
| Stearic acid | 1.5% |
| Mixture of cetylstearyl glucoside and of cetyl and stearyl alcohols | 2% |
| Dimethicone | 0.5% |
| Triethanolamine | 0.45% |
| Preserving agent | 1% |

| Phase B: | |
|---|---|
| Glycerol | 5% |
| Complexing agent | 0.1% |
| Monocetyl phosphate | 1% |

| Phase C: | |
|---|---|
| Xanthan gum | 0.2% |
| Acrylic acid/stearyl methacrylate copolymer | 0.2% |
| Isohexadecane | 1% |

| Phase D: |
|---|
| Triethanolamine qs pH 7 |

The fatty phase (A) is heated to 70° C. The aqueous phase (B) is heated in the final container. Phase (C) is prepared: dispersion of the powders in the oil with rotor-stator stirring, and the fatty phase is then emulsified in the aqueous phase. Phase (C) is then introduced with faster stirring, and the mixture is then stirred slowly until it has cooled to room temperature. The mixture is neutralized (D).

1.5 ml of a 1% solution of graftable species A (solution of pH 9, adjusted with 32% aqueous ammonia) are applied to a 150 mg lock of hair, for 15 minutes at room temperature (25° C.). The lock is then wrung dry, and the antisun cream is then applied.

The hair thus treated has good protection against sunlight.

EXAMPLE 7

Haircare Active Agent D 1-(6-Methyl-4-oxo-1,4-dihydropyrimidin-2-yl)-3-octadec-9-enylurea (6)

Preparation of 1-(6-methyl-4-oxo-1,4-dihydropyrimidin-2-yl)-3-octadec-9-enylurea 6 from isocytosine bearing a carbamic function activated with carbonyldiimidazole 1A

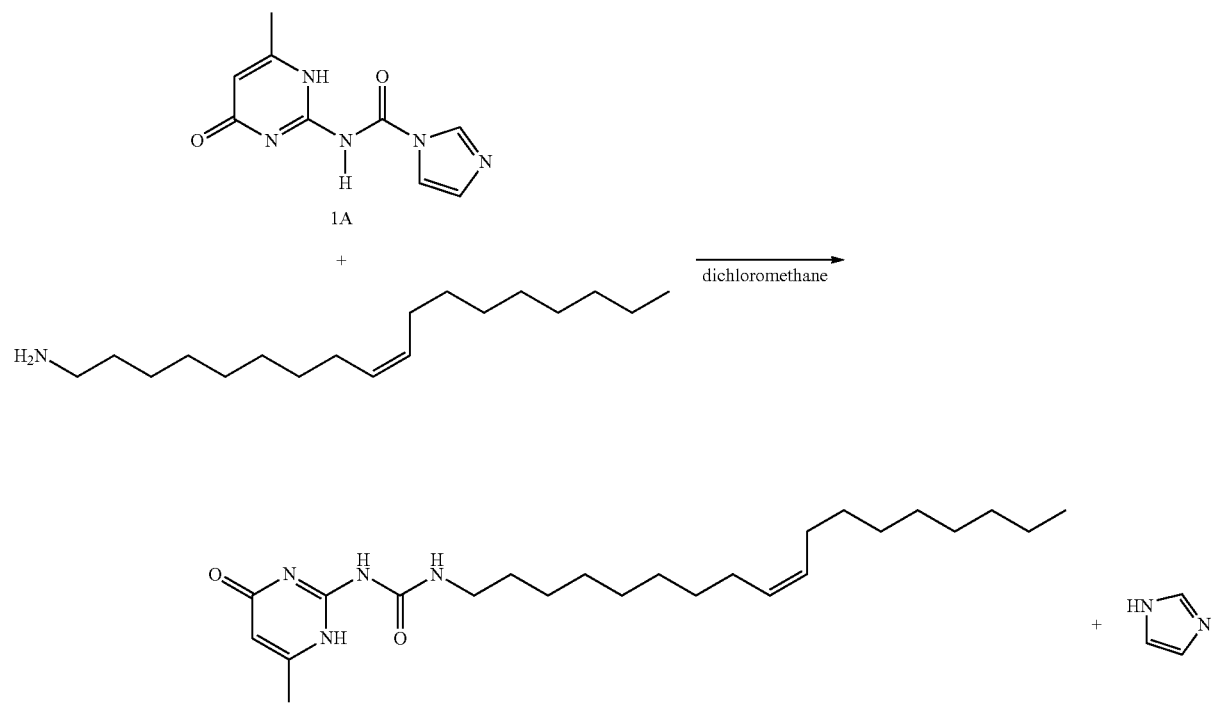

To a solution of 6.43 ml of 70% technical-grade oleylamine (0.027 mol) in 100 ml of dichloromethane were added 6 g of 2-(1-imidazolylcarbonylamino)-6-methyl-4[1H]-pyrimidinone 1A (0.027 mol). The reaction mixture was refluxed for 6 hours, and then evaporated under reduced pressure to give a white paste. This paste was then taken up in 200 ml of acetone, and the precipitate obtained was filtered off on a sinter funnel. The product was dried under vacuum and then recrystallized from a minimum amount of hot ethanol. 10.3 g of a white powder were thus obtained in a yield of 90%.

1H and 13C NMR spectra compliant.

EXAMPLE 8

The following hair composition is prepared:
Compound D of example 7: 0.5%
Cetylstearyl alcohol (50/50 C16-C18): 15%
Cetyl esters: 2%
Water qs 100%

1.5 ml of a 1% solution of graftable species A (solution of pH 9, adjusted with 32% aqueous ammonia) were applied to a 150 mg lock of hair, for 15 minutes at room temperature (25° C.). The lock was then wrung dry, and the hair composition was then applied.

The hair thus treated shows good disentangling in wet medium and also has a soft, silky feel after drying.

EXAMPLE 9

Compound Bearing a Hydrophilic Chain E 1-(2,5,8,11,14,17,20-heptaoxadocosan-22-yl)-3-(6-methyl-4-oxo-1,4-dihydropyrimidin-2-yl)urea

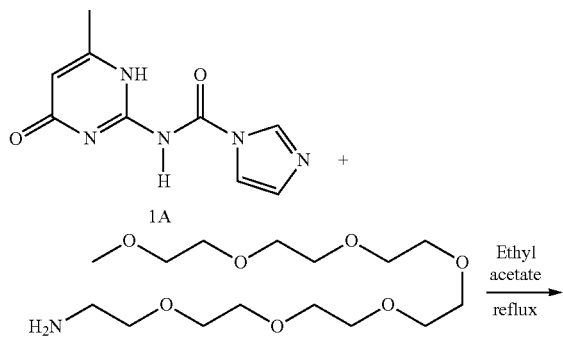

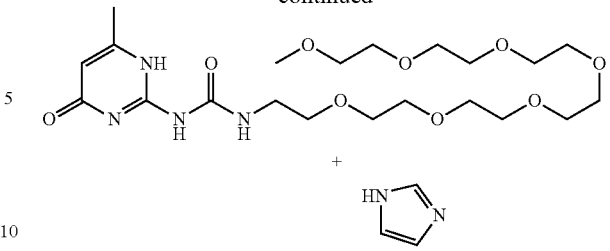

To a suspension of 4.38 g of 2-(1-imidazolylcarbonylamino)-6-methyl-4[1H]-pyrimidinone 1A (0.02 mol) in 200 ml of ethyl acetate were added 7.4 g of 2,5,8,11,14,17,20 heptaoxadocosan-22-amine (0.0218 mol). The reaction mixture was refluxed for 12 hours. The mixture was then allowed to return to room temperature, and was evaporated under reduced pressure. The residue was taken up in acetone (50 ml) and then filtered to remove the imidazole. The filtrate was evaporated under reduced pressure and then taken up again in 50 ml of acetone and filtered. The filtrate was evaporated under reduced pressure. 5.9 g of the expected product were thus obtained in the form of a pasty oil, in a yield of 60%. 1H and 13C NMR spectra compliant.

EXAMPLE 10

The following hair composition is prepared:
Compound E of example 9 1%
Cetylstearyl alcohol (50/50 C16-C18): 3%
behenyltrimethylammonium chloride cationic surfactant: 1.5%
Water qs 100%

1.5 ml of a 1% solution of graftable species A (solution of pH 9, adjusted with 32% aqueous ammonia) were applied to a 150 mg lock of hair, for 15 minutes at room temperature (25° C.). The lock was then wrung dry, and the hair composition was then applied.

The hair thus treated shows good disentangling properties in wet and dry medium and also has a soft, silky feel in a humid atmosphere.

EXAMPLE 11

Silicone Compound F

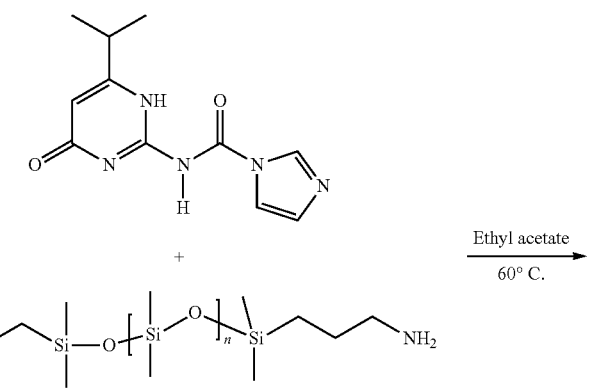

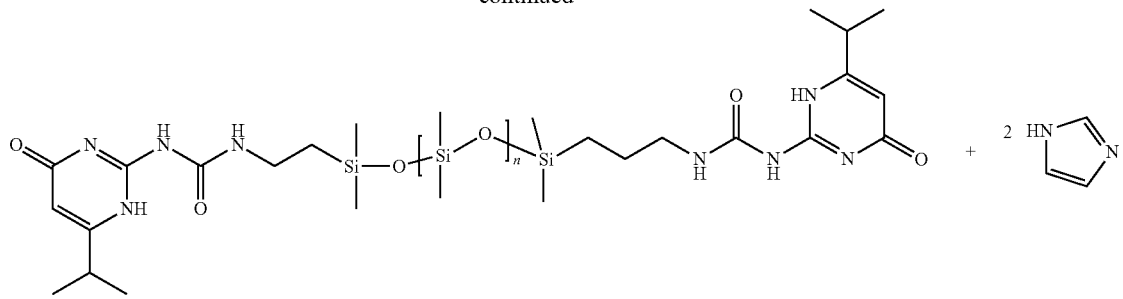

To a suspension of 5 g of aminopropyl polydimethylsiloxane (n being 8-8.5) (DMS-A11 sold by the company Gelest) (0.0056 mol) in 20 ml of ethyl acetate were added 3.12 g of 2-(1-imidazolylcarbonylamino)-6-isopropyl-4[1H]-pyrimidinone (0.0126 mol). The reaction mixture was then maintained at 60° C. for 3 hours and then allowed to return to room temperature. It was then evaporated under reduced pressure, and the residue was taken up in 100 ml of ethyl ether. The organic phase was washed with 1N hydrochloric acid solution and then washed with saturated ammonium chloride solution, dried over sodium sulfate, filtered and then evaporated under reduced pressure. 7.8 g of a white powder were thus obtained, in a yield of 90%.

1H and 13C NMR spectra compliant.

EXAMPLE 12

The following hair composition is prepared:

| | |
|---|---|
| Silicone compound F of example 11 | 4.2 g |
| Dimethoxyethane | 47.66 g |
| -continued | |
| Ethanol | 42.90 g |
| Isododecane | 4.76 g |
| Solution of 2M HCl/water | qs 100 g |

The silicone compound F is dissolved in the dimethoxyethane and the solution is then diluted by addition of ethanol and isododecane. The HCl solution is then added to neutralize the final solution, and water is added to make up to 100 g.

1.5 ml of a 1% solution of graftable species A (solution of pH 9, adjusted with 32% aqueous ammonia) were applied to a 150 mg lock of hair, for 15 minutes at room temperature (25° C.). The lock was then wrung dry, and the hair composition was applied.

The hair thus treated shows good hairstyle hold and good hair sheen.

EXAMPLE 13

Dye G

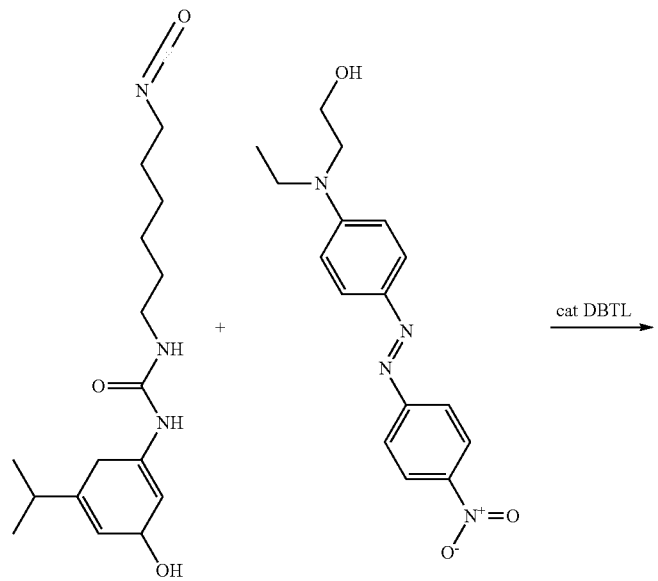

-continued

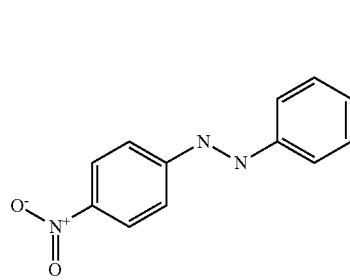

5 g of Disperse Red 1 (n=0.0159; 1 eq.) were placed in 94 ml of tetrahydrofuran in a 250 ml three-necked flask. 5.62 g of SPM2A ureidopyrimidine isocyanate derivative (n=0.0175 mol; 1.1 eq.) dissolved in 20 ml of tetrahydrofuran were then added dropwise via an addition funnel. 20 μL of DBTL (cat.) were then added, and the reaction mixture was maintained overnight at room temperature under argon. A red precipitate gradually formed. It was then filtered off on a sinter funnel, washed with ethyl acetate and dried under vacuum to give 8.674 g (n=0.014 mol) of a red powder, in a yield of 86%.

EXAMPLE 14

Reversibility Study: Violet to Red Coloration

Preparation of the Violet Dye a Solution ($1.25 \times 10^{-2}$ mol/l)

38 mg of dye A of Example 2 were placed in a 25 ml flask, and 200 μl of benzyl alcohol and 800 μl of ethyl alcohol were added. The mixture was heated slightly to 40° C. with a hairdryer in order to dissolve the dye (ultrasonication if necessary). Finally, 4000 μl of water were added. An opaque violet solution was thus obtained.

Preparation of the Red Dye G Solution ($1.25 \times 10^{-2}$ mol/l)

70 mg of dye G of Example 13 were placed in a 25 ml flask, and 500 μl of benzyl alcohol and 500 μl of ethyl alcohol were added. The mixture was heated slightly to 40° C. with a hairdryer in order to dissolve the dye (ultrasonication if necessary). 2 ml of ethyl alcohol and 2 ml of water were then added. A red solution was thus obtained.

Change of dye: in 4 steps
1) Fixing of the Graftable Species A
   5 mL of aqueous solution of the graftable species A of example 1 at 6% by weight and of spontaneous pH were applied for 15 minutes with heating to 60° C. to a 500 mg lock of hair SA20. The lock was then wrung dry, followed by application of
2) Fixing of the Violet Dye A
   5 mL of solution of violet dye A were applied with heating at 60° C. for 15 minutes. A lock dyed a dark violet color was thus obtained.
3) Shampooing
   The lock was then shampooed with 0.2 mL of a sodium lauryl sulfate solution at 2% by weight (strong decrease in coloration) and was wrung dry.
4) Fixing of the Red Dye G
   5 mL of the solution of red dye G were applied with heating at 60° C. for 15 minutes. The lock was wrung dry and then dried to obtain a lock dyed red.

The invention claimed is:
1. A cosmetic process for treating keratin materials, comprising the application to said materials:

in a first stage, of a cosmetic composition comprising at least one compound comprising at least one unit of formula (Ia):

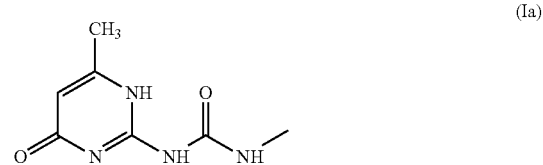

(Ia)

and in a second stage, of a cosmetic composition comprising at least one cosmetic active agent bearing at least one unit of formula (Ia):

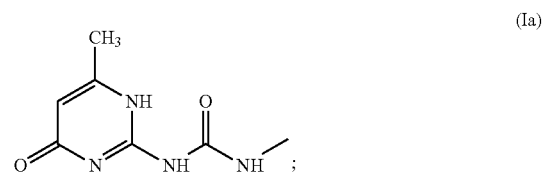

(Ia)

wherein the compound bearing the unit (Ia) in the first stage is chosen from the compounds of formula (II), and salts and hydrates and tautomeric forms thereof:

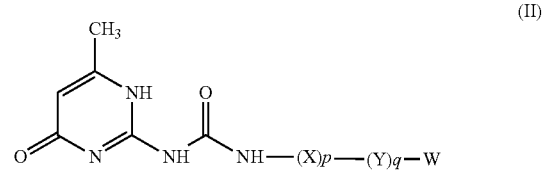

(II)

in which:
X represents a linear or branched, saturated or unsaturated, divalent C1-C30 hydrocarbon-based chain, optionally interrupted with and/or bearing, at one or both of its ends, one or more divalent groups chosen from —N(R)—, —N$^+$(R)(R')-, —O—, —S—, —C(O)—, —SO$_2$—, and an aromatic or non-aromatic, saturated or unsaturated, fused or non-fused divalent C3-C7 (hetero) cyclic radical, optionally comprising one or more identical or different heteroatoms chosen from N, S and O, optionally substituted with OH or NR"R'";
with R and R', which may be identical or different, chosen from a hydrogen, a linear or branched, saturated or unsaturated C1-C4 alkyl radical, optionally substituted with OH and/or NR"R'", with R" and R''', which may be identical or different, chosen from H or a linear or branched, saturated or unsaturated C1-C4 alkyl radical;
p is equal to 0 or 1;
q is equal to 0 or 1;
Y represents a linear, branched and/or cyclic, saturated or unsaturated divalent C1-C18 hydrocarbon-based chain, optionally substituted with OH and/or NR"R''',
W represents a unit for grafting onto keratin materials and is selected from the group consisting of
(i) a thiol,
(ii) a protected thiol of formula —S-Pr with Pr representing a member selected form the group consisting of:
  a) a saturated or unsaturated, fused or non-fused, aromatic or non-aromatic C5-C6 heterocycle protecting group, optionally comprising N, O, S and/or P heteroatoms;
  b) a sp² carbon protecting group;
  c) a sp$^a$ carbon protecting group;
  d) a metal protecting group;
  e) a substituted sulfur atom protecting group; and
  f) a photosensitive protecting group;
(iii) a nucleofugal group; and
(v) a group containing one or more siloxanes;
and wherein the cosmetic active agent is selected from the group consisting of keratin fiber caring agents, dyeing active agents, compounds containing hydrophilic active chains, compounds containing silicon chains, fatty substances, UV-screening agents, hyaluronic acid and derivatives of hyaluronic acid.

2. The process as claimed in claim 1, in which the compound bearing the unit (Ia) is chosen from the following compounds:

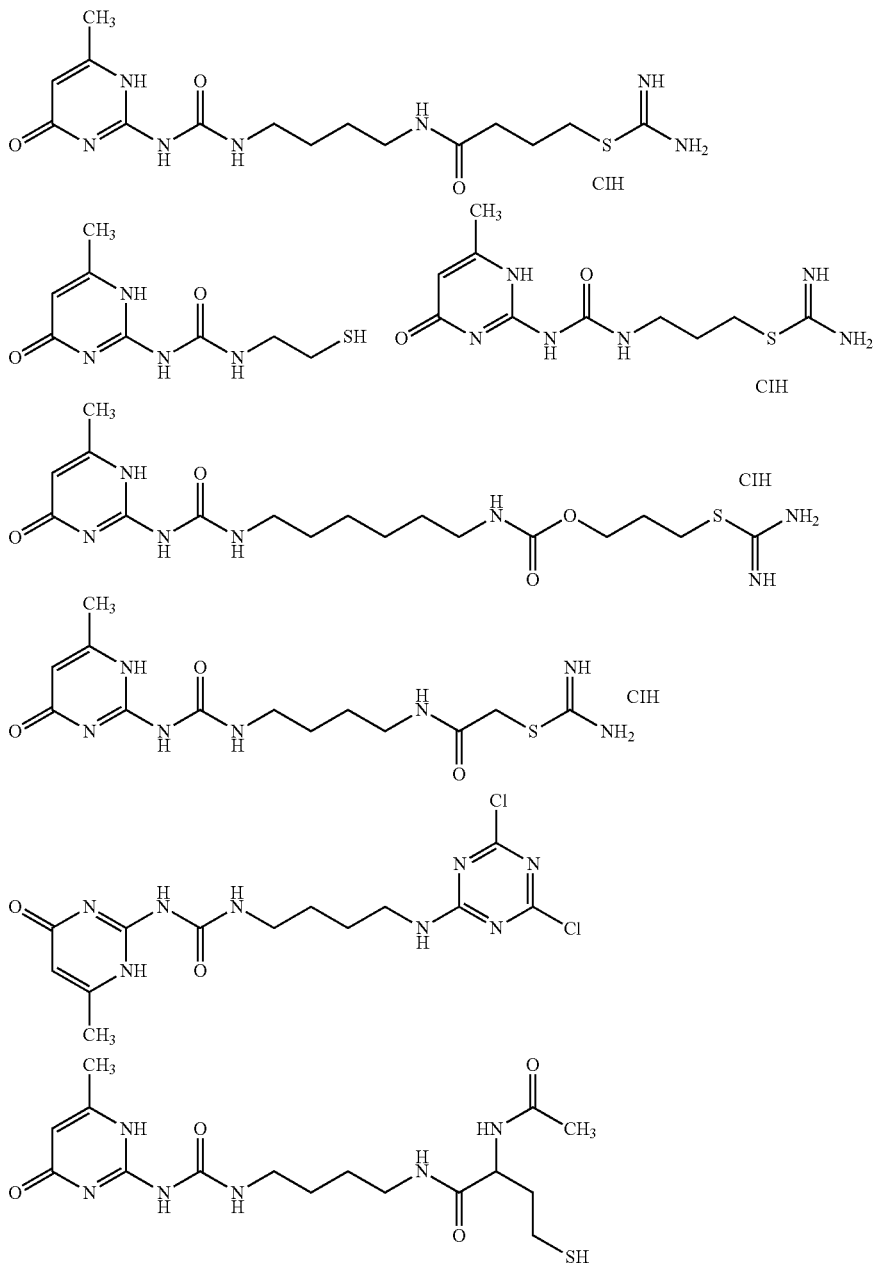

-continued

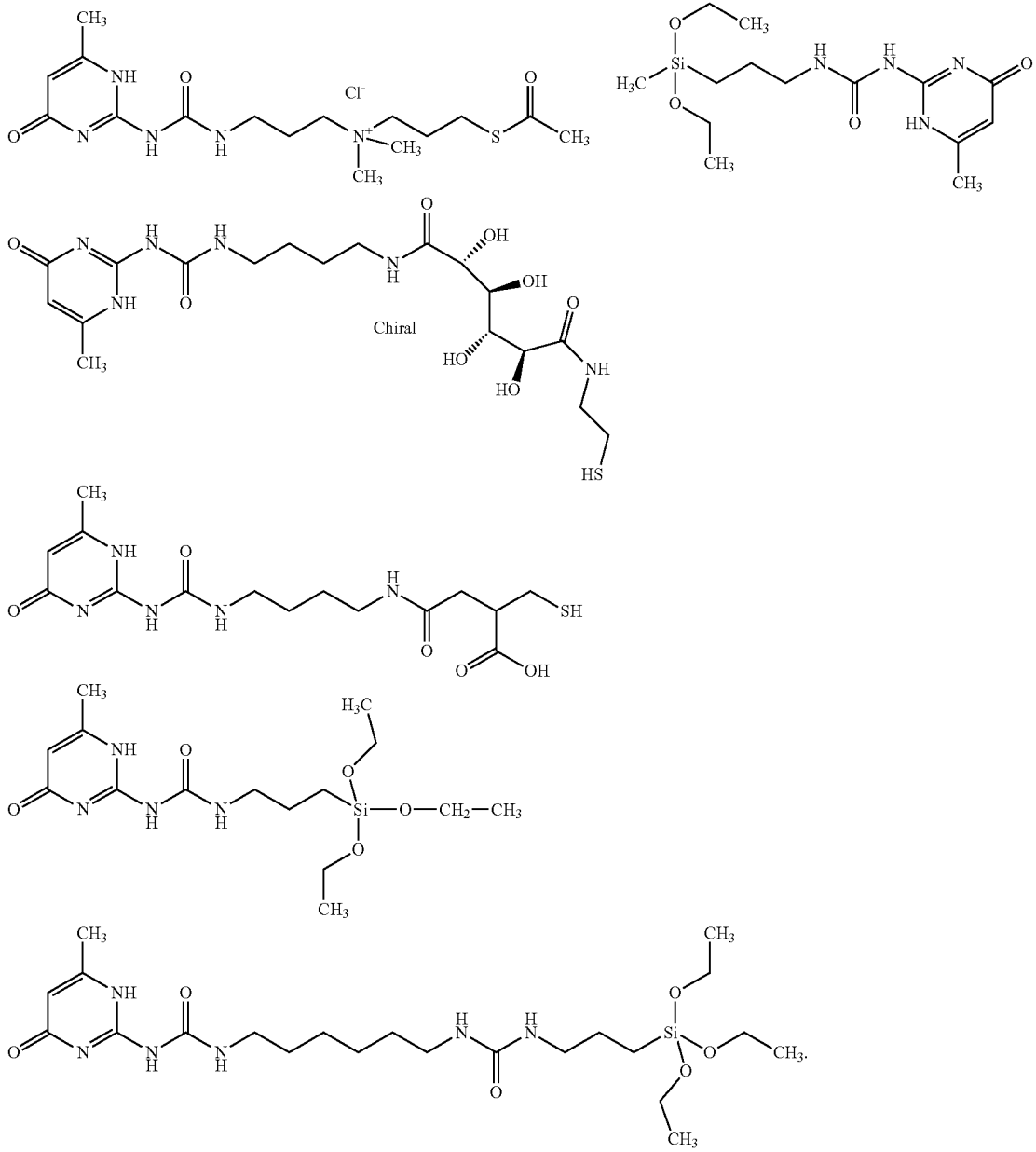

3. The process as claimed in claim 1, in which the compound bearing the unit (Ia) is in an amount of from 0.1% to 10% by weight in the composition comprising it.

4. The process as claimed in claim 1, in which the cosmetic active agent is a cosmetic active agent for caring for keratin fibers of formula (III), and also the salts, addition salts, isomers, hydrates, and tautomeric forms thereof:

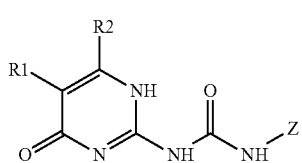

(III)

in which:

R1=H and R2=methyl; and

Z represents a monovalent radical chosen from:
(i) a linear or branched C9 to C32 (saturated) alkyl radical;
(ii) a linear or branched C9 to C32 (unsaturated) alkene radical;
said radicals optionally being substituted with 1 to 8 groups chosen from —OH, —OR, —SO₃H, —SO₃R, —SO₂NRR', —COOH, —NRR' and —N⁺RR'R", with R, R' and R"=H or C1-C6 alkyl; and/or said radicals optionally comprising 1 to 8 divalent groups chosen, alone or as a mixture, from —NH— (or =NH), —O—, —C(O)—, —C(=NH)—, —N⁺(CH₃)₂-An⁻ (An⁻: anion); or alternatively —N=(trivalent).

5. The process as claimed in claim 1, in which the cosmetic active agent is a supramolecular oil, which is obtainable by reaction between:

on the one hand, at least one oil bearing at least one nucleophilic and/or electrophilic reactive function, and
on the other hand, at least one junction group capable of establishing hydrogen bonds with one or more partner junction groups, each junction group pairing involving at least 3 hydrogen bonds, said junction group bearing at least one reactive function capable of reacting with the reactive function borne by the oil, said junction group comprising at least one unit of formula (I') or (II'):

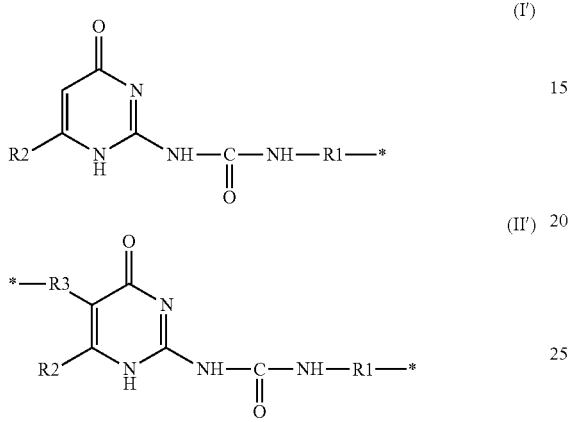

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents $CH_3$.

6. The process as claimed in claim 1, in which the cosmetic active agent is a supramolecular wax, which is obtainable by reaction between:
at least one wax bearing at least one reactive function chosen from OH and COOH, or even anhydride, and
at least one junction group capable of establishing hydrogen bonds with one or more partner junction groups, each junction group pairing involving at least 4 hydrogen bonds, said junction group bearing at least one "complementary" reactive function capable of reacting with the reactive function borne by the wax, said junction group comprising at least one unit of formula (I') or (II'):

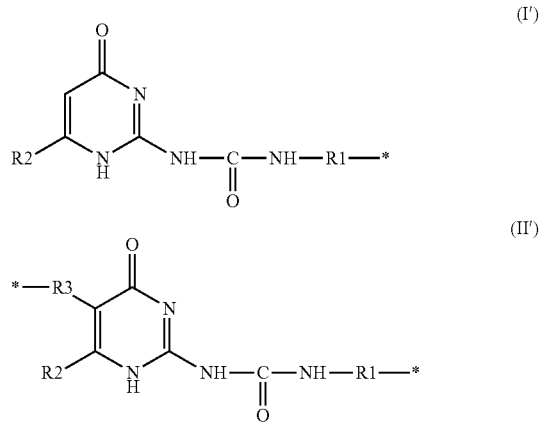

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents $CH_3$.

7. The process as claimed in claim 1, in which the cosmetic active agent bearing at least one unit of formula (Ia), or the mixture of such active agents, is present in the composition in an amount of from 0.01% to 50% by weight relative to the total weight of the composition.

8. The process as claimed in claim 1, in which the compound bearing the unit (Ia) is chosen from the following compounds:

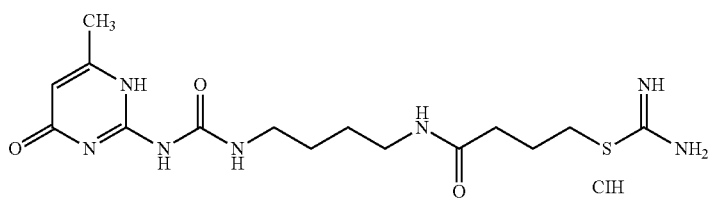

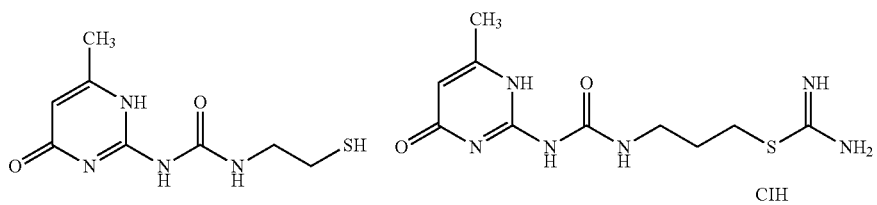

-continued
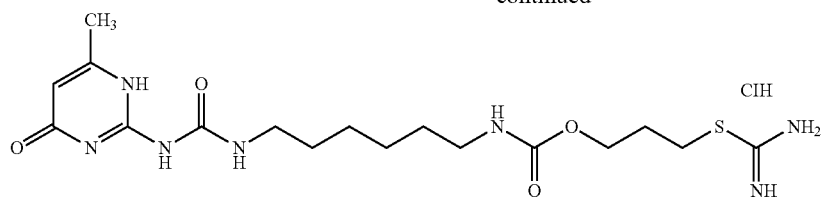
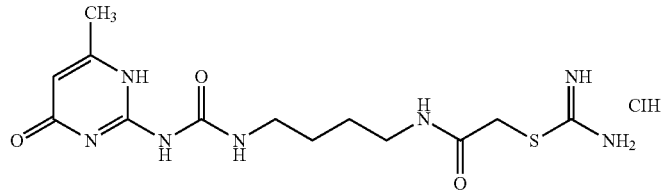
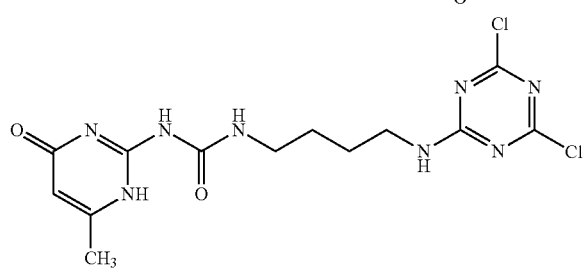
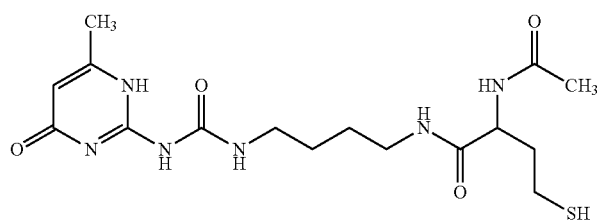
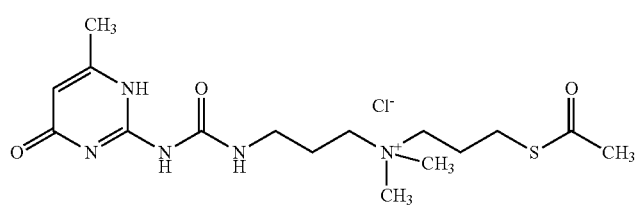
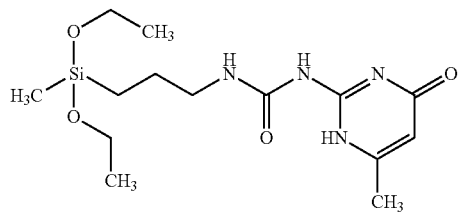
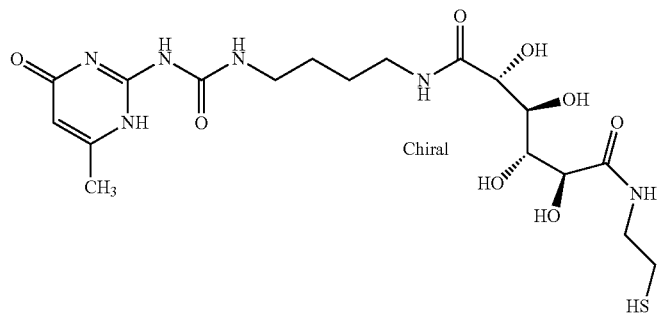
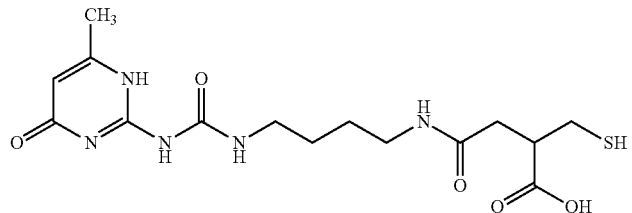

-continued
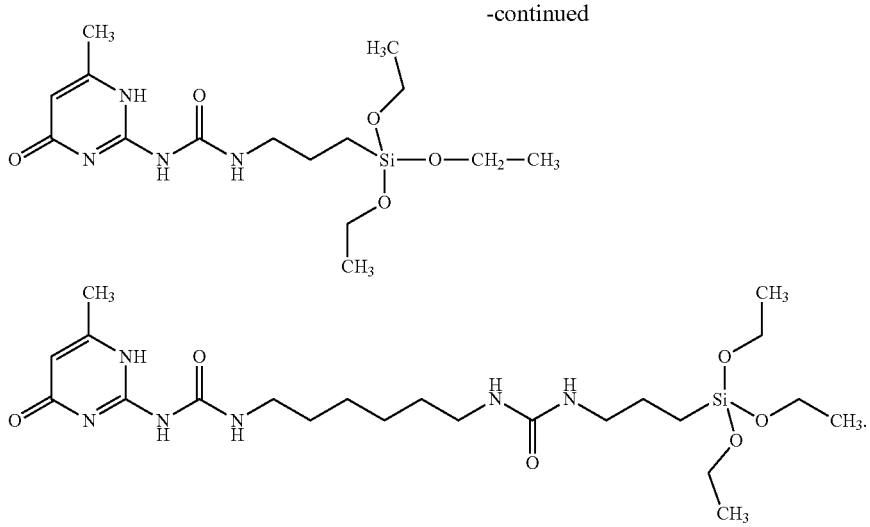
9. The process as claimed in claim 1, in which the compound bearing the unit (Ia) is chosen from the following compounds:
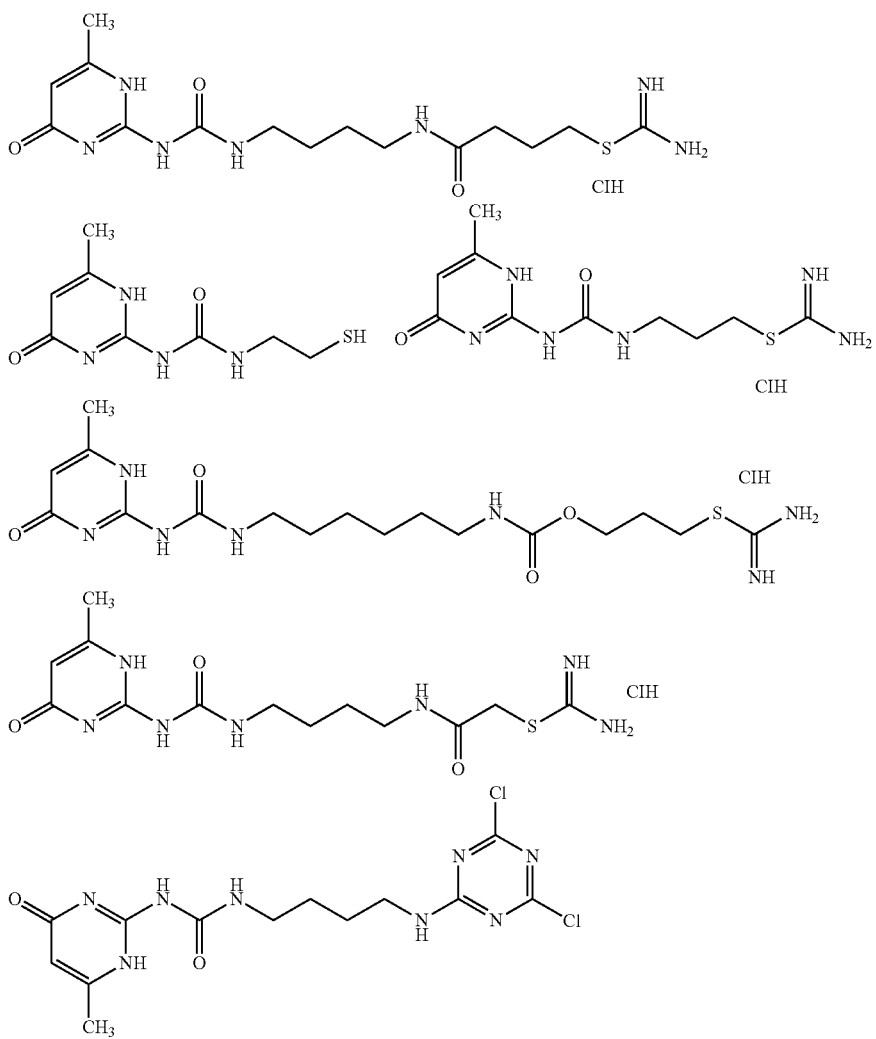

-continued
155
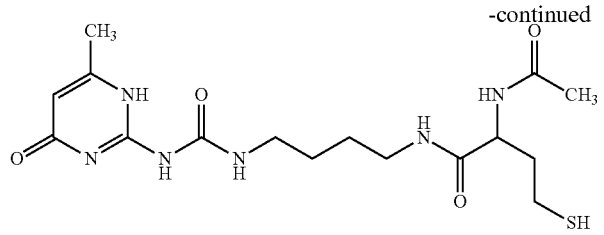
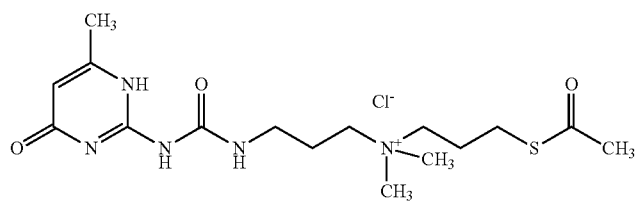
156
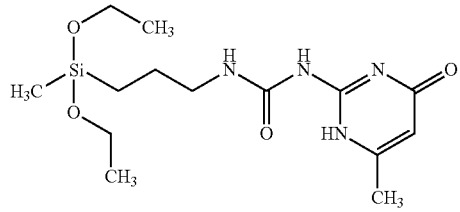
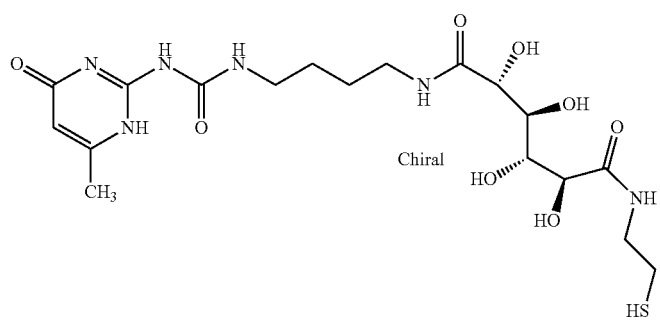
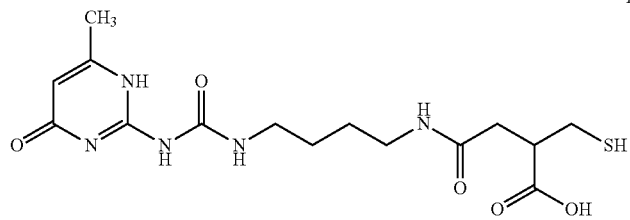
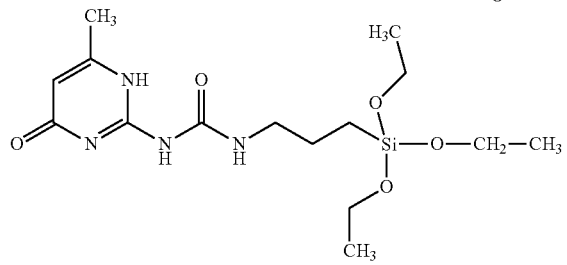
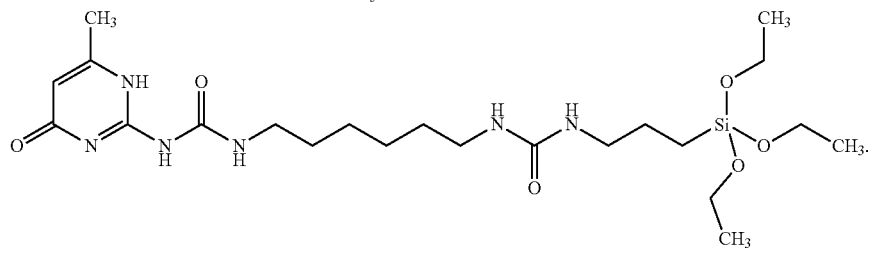
* * * * *